United States Patent
Fayad

(10) Patent No.: US 9,757,346 B2
(45) Date of Patent: Sep. 12, 2017

(54) COMPOSITIONS AND METHODS FOR TREATING INSULIN RESISTANCE AND NON-INSULIN DEPENDENT DIABETES MELLITUS (TYPE II DIABETES)

(75) Inventor: Joseph M. Fayad, Las Vegas, NV (US)

(73) Assignee: VOLANT HOLDINGS GMBH, Feusisberg (CH)

( * ) Notice: Subject to any disclaimer, the term of this patent is extended or adjusted under 35 U.S.C. 154(b) by 0 days.

(21) Appl. No.: 12/932,633

(22) Filed: Mar. 2, 2011

(65) Prior Publication Data

US 2011/0268795 A1 Nov. 3, 2011

Related U.S. Application Data

(63) Continuation-in-part of application No. PCT/US2009/005016, filed on Sep. 2, 2009.

(60) Provisional application No. 61/190,818, filed on Sep. 3, 2008, provisional application No. 61/309,991, filed on Mar. 3, 2010.

(51) Int. Cl.

| | |
|---|---|
| *G01N 33/66* | (2006.01) |
| *G01N 33/74* | (2006.01) |
| *A61K 31/7004* | (2006.01) |
| *A61K 9/28* | (2006.01) |
| *A61K 36/05* | (2006.01) |
| *A61K 45/06* | (2006.01) |
| *A61K 31/195* | (2006.01) |
| *A61K 31/20* | (2006.01) |
| *A61K 31/30* | (2006.01) |
| *A61K 36/48* | (2006.01) |
| *A61K 36/899* | (2006.01) |
| *A61K 38/02* | (2006.01) |

(52) U.S. Cl.
CPC ............ *A61K 31/195* (2013.01); *A61K 31/20* (2013.01); *A61K 31/30* (2013.01); *A61K 31/7004* (2013.01); *A61K 36/05* (2013.01); *A61K 36/48* (2013.01); *A61K 36/899* (2013.01); *A61K 38/02* (2013.01); *G01N 33/66* (2013.01); *G01N 2800/04* (2013.01); *G01N 2800/06* (2013.01)

(58) Field of Classification Search
CPC ............ A61K 2300/00; A61K 31/7004; A61K 36/05; A61K 36/48; A61K 38/212; A61K 36/8998; A61K 45/06; A61K 31/00; A61K 31/20; A61K 31/70; A61K 31/7072; A61K 9/0053; A61K 9/2013; A61K 9/2054; A61K 9/2846; A61K 9/28; A61K 9/4891; A61K 36/899; A61K 9/5005; A61K 9/5047; A61K 9/5073; G01N 2800/04; G01N 2800/06; G01N 2800/52; G01N 33/66; G01N 33/74
See application file for complete search history.

(56) References Cited

U.S. PATENT DOCUMENTS

| | | | |
|---|---|---|---|
| 4,544,550 A * | 10/1985 | Rodolfo | ............ 424/600 |
| 5,194,464 A * | 3/1993 | Itoh et al. | ............ 524/42 |
| 5,322,697 A | 6/1994 | Meyer | |
| 5,753,253 A * | 5/1998 | Meyer | ............ 424/439 |
| 6,248,527 B1 | 6/2001 | Chen et al. | |
| 6,267,988 B1 | 7/2001 | Meyer | |
| 6,270,774 B1 * | 8/2001 | Hsia et al. | ............ 424/195.11 |
| 7,329,419 B2 * | 2/2008 | Yatcilla et al. | ............ 424/725 |
| 8,026,281 B2 | 9/2011 | Doyle, Jr. et al. | |
| 8,173,178 B1 | 5/2012 | Ghaedian et al. | |
| 2005/0244518 A1 | 11/2005 | Huang et al. | |
| 2007/0014756 A1 * | 1/2007 | Touchot | ............ A61K 47/48092 424/78.27 |
| 2010/0159079 A1 | 6/2010 | Qvyjt | |
| 2010/0267643 A1 | 10/2010 | Baron et al. | |

FOREIGN PATENT DOCUMENTS

| | | |
|---|---|---|
| WO | 8703198 A1 | 6/1987 |
| WO | 0018377 A1 | 4/2000 |
| WO | 2010102041 A2 | 9/2010 |

OTHER PUBLICATIONS

Scott Grundy, et al, Definition of Metabolic Syndrome, 109 Circulation 433 (2004).*
Gregory Morton, et al, Leptin Action in the Forebrain Regulates the Hindbrain Response to Satiety Signals, 115 J Clin. Invest. 703 (2005).*
Jong-Yuh Cherng & Mei-Fen Shih, Improving Glycogenesis in Streptozocin (STZ) Diabetic Mice After Administration of Green Algae Chlorella, 78 Life Sci. 1181 (2006).*

(Continued)

*Primary Examiner* — Ernst V Arnold
(74) *Attorney, Agent, or Firm* — Henry D. Coleman; R. Neil Sudol

(57) ABSTRACT

The invention provides methods of treatment that induce satiety in a subject for a period of at least around twenty-four hours by once-daily administration to the subject of a controlled release dosage form, wherein the dosage form is administered while the subject is in the fasted state and at a time of around six to around nine hours prior to the subject's next intended meal, and wherein the dosage form comprises a controlled release composition, which comprises an enterically-coated, ileum hormone-stimulating amount of a nutritional substance and releases the majority of the nutritional substance in vivo upon reaching the subject's ileum. The invention also provides a diagnostic tool for probing the health and disease state of the ileal hormones, excess or deficiencies. The invention provides a safe vehicle for targeted deliveries of chemical, pharmaceuticals, natural substances and nutrition to the ileum. The present invention also provides a method for treating noninsulin dependent diabetes mellitus, pre-diabetic symptoms, and insulin resistance, as well as a number of disease states and conditions including gastrointestinal disorders as otherwise described herein.

101 Claims, 56 Drawing Sheets

(56) References Cited

OTHER PUBLICATIONS

Zhaoping Li, et al, Meta-Analysis: Pharmacologic Treatment of Obesity, 142 Ann. Intern. Med. 532 (2005).*
Donald Hensrud, Dietary Treatment and Long-Term Weight Loss and Maintenance in Type 2 Diabetes, 9 Obesity Res. 348S (Nov. 4, 2001).*
Robert Ross, et al, Reduction in Obesity and Related Comorbid Conditions after Diet-Induced Weight Loss or Exercise-Induced Weight Loss in Men, 133 Ann. Intern. Med. 92 (Jul. 18, 2000).*
April Strader, et al, Weight Loss through Ileal Transposition is Accompanied by Increased Ileal Hormone Secretion and Synthesis in Rats, 288 Am. J Physiol. Endocrinol. Metab. E447 (2005).*
April D. Strader, et al, Weight Loss Through Ileal Transposition is Accompanied by Increased Ileal Hormone Secretion and Synthesis in Rats, 288 Am. J Physiol. Endocrinol. Metab. E447 (2004).*
Lotte Knudsen, Glucagon-like Peptide-1: The Basis of a New Class of Treatment for Type 2 Diabetes, 47 J Med. Chem. 4128 (2004).*
H.E. Magee & E. Reid, The Absorption of Glucose from the Alimentary Canal, 73 J Physiol. 163 (1931).*
Cani, et al, Improvement of Glucose Tolerance and Hepatic Insulin Sensitivity by Oligofructose Requires a Functional Glucagon-Like Peptide 1 Receptor, 55 Diabetes 1484 (May 2005).*
Josephine Egan, et al, GLP-1 Receptor Agonists are Growth and Differentiation Factors for Pancreatic Islet Beta Cells, 19 Diabetes. Metab. Res. Rev. 115 (2003).*
Steven Kahn, et al, Mechanisms Linking Obesity to Insulin Resistance and Type 2 Diabetes, 444 Nature 840 (2006).*
Michael Perley & David Kipnis, Plasma Insulin Reposnes to Oral and Intravenous Glucose: Studies in Normal and Diabetic Subjects, 46 J Clin. Invest. 1954 (1967).*
Kelly (Am J Clin Nutr 2003;78(suppl):858S-64S).*
Kahn et al. (The Journal of Clinical Investigation 2000;106(4):473-481).*
Holst (Diabetes/Metabolism Research and Reviews 2002:18:430-441).*
Dumoulin et al. (Endocrinology 1998; 139(9):3780-3786).*
Cefalu (Medical Management of Diabetes Mellitus 2000, CRC Press pp. 169 and 304) 2 pages.*
Zhao et al. (Proc. Natl. Acad. Sci. USA 1997; 94:3223-3228).*
Kahn et al. (Nature 2006;444:840-846; hereinafter Kahn 2006).*
Gross (Br. J Clin Pharmacol. 1998;46:95-99).*
Iqbal et al. (J. Gastrointest Surg. 2008;12(11)1854-1865).*
Reaven (Diabetes Vasc Dis Res. 2005;2:105-12).*
Hardy et al. (Curr Opin Endocrinol Diabetes Obes. 2012;19(2):81-87).*
Grundy SM, Brewer HB Jr, Cleeman JI, Smith SC Jr, Lenfant C. Definition of metabolic syndrome: report of the National Heart, Lung, and Blood Institute/American Heart Association conference on scientific issues related to definition. Arteriscler Thromb Vack Biol. 2004;24(2):e13-18.
Grundy SM. Metabolic syndrome: part II. Endocrinol Metab Clin North Am 2004:33(3):xi-xiii.
Grundy SM. Cholesterol gallstones: a fellow traveler with metabolic syndrome? Am J Clin Nutr. 2004:80(1):1-2.
Grundy SM. Obesity, metabolic syndrome, and cardiovascular disease. J Clin Endocrinol Metab. 2004:89 (6):2595-2600.
Grundy SM. Metabolic syndrome part I. Endocrinol Metab Clin North Am.
Grundy SM. What is the contribution of obesity to the metabolic syndrome? Endocrinol Metab Clin North Am. 2004;33(2):267-282, table of contents.
Grundy SM, Brewer HB Hr, Cleeman JI, Smith SC Jr, Lenfant C. Definition of metabolic syndrome: report of the National Heart, Lung, and Blood Institute/American Heart Association conference on scientific issues related to definition. Circulation. 2004;109(3):433-438.
Grundy SM, Hansen B, Smith SC Jr, Cleeman JI, Kahn RA. Clinical management of metabolic syndrome: report of the American Heart Association/National Heart, Lung, and Blood Institute/American Diabetes Association conference on scientific issues related to management. Arterioscler Thromb Vasc Biol. 2004;24(2):e19-24.
Grundy SM, Hansen B, Smith SC Jr, Cleeman JI, Kahn RA. Clinical management of metabolic syndrome: report of the American Heart Association/National Heart, Lung, and Blood Institute/American Diabetes Association conference on scientific issues related to management. Circulation. 2004;109(4):551-556.
Ridker PM, Wilson PW, Grundy SM. Should C-reactive protein be added to metabolic syndrome and to assessment of global cardiovascular risk? Circulation. 2004;109(23):2818-2825.
Grundy SM. Pre-diabetes, metabolic syndrome, and cardiovascular risk. J Am Coll Cardiol. 2012;59(7):635-643.
Li Z, Maglione M, Tu W, Mojica W, Arterburn D, Shugarman LR, et al. Meta-analysis: pharmacologic treatment of obesity. Ann Intern Med. 2005;142(7):532-546.
Meyer JH, Tabrizi Y, Dimaso N, Hlinka M, Raybould HE. Length of intestinal contact on nutrient-driven satiety. Am J Physiol. 1008;275(4 pt 2):R1308-1319.
Meyer JH, Hlinka M, Tabrizi Y, Dimaso N, Raybould HE. Chemical specificities and intestinal distributions of nutrient-driven satiety. Am J Physiol. 1998;275(4 Pt 2):R1293-1307.
O'Donovan DG, Doran S, Feinle-Bisset C, Jones KL, Meyer JH, Wishart JM, et al. Effect of variations in small intestinal glucose delivery on plasma glucose, insulin, and incretin hormones in healthy subjects and type 2 diabetes. J Clin Endocrinol Metab. 2004;89(7):3431-3435.
Morton GJ, Blevins JE, Williams DL, Niswender KD, Gelling RW, Rhodes CJ, et al. Leptin action in the forebrain regulates the hindbrain response to satiety signals. J Clin Invest. 2005;115(3):703-710.
Nichols, GA. Medical Utilization and Annual Health Care Costs in Patients With Type 2 Diabetes Mellitus Before and After Bariatric Surgery. www.medscape.com, Oct. 12, 2010.
Al-Attas OS, Al-Daghri NM, Al-Rubeaan K, Da Silva NF, Sabico SL, Kumar S, McTernan PG, Harte AL. Changes in ednotoxin levels in T2DM subjects on anti-diabetic therapies. Cardiovascular Diabetology, 2009;8(20).
Breen DM, Rasmussen BA, Kokorovic A, Mang R, Cheung G, Lam T. Jejunal nutrient sensing is required for duodenal-jejunal bypass surgery to rapidly lower glucose concentrations in uncontrolled diabetes. Nature Medicine, 2012.
Chaudhry MZ, Wang JH, Blankson S, Redmond HP. Statin (Cerivastatin) Protects Mice Against Sepsis-Related Death via Reduced Proinflammatory Cytokines and Enhanced Bacterial Clearance. Surgical Infections 2009;9 (2):183-194.
Chaudhuri A, Ghanim H, Vora M, Korzeniewski K, Abuaysheh S, Makdissi A, Dandona P. Exenatide Exerts a Potent Anti-inflammatory Action. J Clin Endocrinol Metab. Jan. 2012;97(1):Abstract.
Dhindsa S, Furlanetto R, Vora M, Ghanim H, Dandona P. Low Estradiol Concentrations in Males with Hypogonadotrophic Hypogonadism and Type 2 Diabetes. Endocr Rev, 2011;32:Abstract.
Caruana J, Monte S, Ghanim H, Dhindsa S, Korzeniewski K, Schentag J, Dandona P. Reduction in Plasma Concentrations of Endotoxin (LPS) and the Expression of Toll like Receptor-4 (TLR-4) and TLR-2 Following Roux-en-Y Gastric Bypass Surgery (RYGB) and Weight Loss. Endocr Rev, 2011;32:Abstract.
Dandona P, Ghanim H, Monte S, Sia Cl, Schentag J, Dhindsa S, Caruana J. Reduction in the Expression of beta-amyloid Precursor Protein (APP) Following Roux-en-Y Gastric Bypass Surgery (RYGB) and Weight Loss. Endocr Rev, 2011;32:Abstract.
Dandona P, Makdissi A, Sia CL, Vora M, Korzeniewski K, Ghanim H. Sitagliptin Exerts an Anti-Inflammatory Effect. 2011;32:Abstract.
Dandona P, Mohamed I, Ghanim H, Sia CL, Dhindsa S, Makdissi A, Chaudhuri A. A Low Dose Insulin Infusion Suppresses the Expression of beta-amyloid Precursor Protein. 2011;32:Abstract.
Varanasi A, Bellini N, Rawal D, Vora M, Makdissi A, Dhindsa S, Chaudhuri A, Dandona P. Liraglutide as Additional Treatment in Type 1 Diabetes. 2011;32:Abstract.
Edelson E. Popular Diet Plans Can Unclog Arteries. www.healthday.com, Mar. 4, 2010.

(56) References Cited

OTHER PUBLICATIONS

Mela, D.J. Novel food technologies: enhancing appetite control in liquid meal replacers. Obesity 2006, 14:179S-181S.
Hood M. Study raises hope for guy disease cures. news.yahoo.com, Mar. 3, 2010.
Mohn A, Catino M, Capanna R, Giannini C, Marcovecchio M, Chiarelli F. Increased Oxidative Stress in Prepubertal Severely Obese Children: Effect of a Dietary Restriction-Weight Loss Program. J Clin Endocrinol Metab; 2005;90(5):2653-2658.
National Diabetes Education Program. Guiding Principles for Diabetes Care: for Health Care Professionals. http://www.ndep.nih.gov/media/guidprin_hc_eng.pdf, 2009.
Orrhage K, Sjostedt S. Nord CE. Effect of supplements with lactic acid bacteria and oligofructose on the intestinal microflora during administration of cefpodoxime proxetil.
Rao RS, Yanagisawa R, Kini S. Insulin resistance and bariatric surgery. Obesity Reviews, 2011.
Rhee NA, Vilsboll T, Knop FK. Current evidence for a role og GLP-1 in Roux-en-Y gastric bypass-induced remission of type 2 diabetes. Diabetes, Obesity and Metabolism, 2012;14:291-298.
Riedl M, Vila G, Maier C, et al. Plasma Osteopontin Increases After Bariatric Surgery and Correlates with Markers of Bone Turnover But Not with Insulin Resistance.
Vastag B. Stomach surgery more effective than medicine for diabetes, studies find. The Washington Post, Mar. 26 2012.
Waknine Y. Diabetes Risk Increased by 3 Independent Factors. www.medscape.com/viewarticle/760732_print.
Mackins H. Structure House Presents Data Correlating Weight Loss, Reduction of Diabetes Risk Factors and Lowering of PreDx(R) Diabetes Risk Score. http://www.clinicaspace.com/news_print.aspx?NewsEntityID=225397.
Thomas G, Sehgal AR, Kashyap SR, Sriviva TR, Kirwan JP. Navaneethan SD. Metabolic Syndrome and Kidney Disease: A Systematic Review and Meta-Analysis. Clin J Am Soc Nephrol, 2011;6(10):2364-2373.
Tiano JP, Mauvais-Jarvis F. Importance of oestrogen receptors to preserve functional beta-cell mass in diabetes Nature Reviews Endocrinology, 2012;8:342-351.
USDA Database for the Added Sugars Content of Selected Foods. U.S. Department of Agriculture, Agricultural Research Service, Beltsville Human Nutrition Research Center, Nutrient Data Laboratory, Feb. 2006. Beltsville, Maryland.
Gebhardt S, Thomas RG. Nutritive Value of Foods. United States Department of Agriculture, Agrucultural Research Service, Home and Garden Bulletin 72, Oct. 2002. Beltsville, Maryland.
Weight Loss Surgery May Help Diabetes. Health Day, Jan. 6, 2012. http://health.usnews.com/health-news/diet-fitness/diabetes/articles/2012/01/06/weight-loss-surgery-may-help-diabetes.
Lowes R. Weight-Management Web Site Helps Regular Users the Most. Medscape Medical News. Jul. 27, 2010. www.medscape.com/viewarticle/725889_print.
Schaur PR, et al. Bariatric Surgery versus Intensive Medical Therapy in Obese Patients with Diabetes. N Engl J Med, 2012.
Food and Nutrition Board. Dietary Reference Intakes for Energy, Carbohydrate, Fiber, Fat, Fatty Acids, Cholesterol, Protein, and Amino Acids. Institute of Medicine of the National Academies, 2005.
Ghanim H, et al. Increase in Plasma Endotoxin Concentration and the Expression of Toll-Like Receptors and Suppressor of Cytokine Signaling-3 in Mononuclear Cells After a High-Fat, High-Carbohydrate Meal. Diabetes Car, 2009;32(12):2281-2287.
Baumann K. Making Fat. Nature Reviews Molecular Cell Biology, 2012;13.
Schauer PR, Kashyap SR, Wolski K, Brethauer SA, Kirwan JP, Pothier CE, et al. Bariatric surgery versus intensive medical therapy in obese patients with diabetes. N Engl J Med. 2012;366(17):1567-76.
Ranganath LR, Beety JM, Morgan LM, Wright JW, Howland R, Marks V. Attenuated GLP-1 secretion in obesity: cause or consequence? Gut. 1996;38(6):916-9.

Baynes KC, Dhillo WS, Bloom Sr. Regulation of food intake by gastrointestinal hormones. Curr Opin Gastroenterol. 2006;22(6):626-31.
Drucker DJ. Glucagon-like peptide 2. J Clin Endocrinol Metab. 2001;86(4):1759-64.
Holst JJ. The physiology of glucagon-like peptide 1. Physiol Rev. 2007;87(4):1409-39.
Chaudhri O, Small C, Bloom S. Gastrointestinal hormones regulating appetite. Philos Trans R Soc Lond B Biol Sci. 2006;361(1471):1187-209.
Chaudhri OB, Field BC, Bloom SR. Editorial: from gut to mind—hormonal satiety signals and anorexia nervosa. J Clin Endocrinol Metab. 2006;91(3):797-8.
Chaudhri OB, Parkinson JR, Kuo YT, Druce MR, Herlihy AH, Bell JD, et al. Differential hypothalamic neuronal activation following peripheral injection of GLP-1 and oxyntomodulin in mice detected by manganese-enhanced magnetic resonance imaging. Biochem Biophys Res Commun. 2006;350(2):298-306.
Chaudhri OB, Wynne K, Bloom SR. Can gut hormones control appetite and prevent obesity? Diabetes Care. 2008;31 Suppl 2:S284-9.
Field BC, Chaudhri OB, Bloom SR. Bowels control brain: gut hormones and obesity. Nat Rev Endocrinol. 2010;6(8):444-53.
Field BC, Wren AM, Cooke D, Bloom SR. Gut hormones as potential new targets for appetite regulation and the treatment of obesity. Drugs. 2008;68(2):147-63.
Field BC, Wren AM, Peters V, Baynes KC, Martin NM, Patterson M, et al. PYY3-36 and oxyntomodulin can be additive in their effect on food intake in overweight and obese humans. Diabetes. 2010;59(7):1635-9.
Jayasena CN, Bloom SR. Role of gut hormones in obesity. Endocrinol Metab Clin North Am. 2008;37(3):769-87, xi.
Boushey RP, Abadir A, Flamez D, Baggio LL, Li Y, Berger V, et al. Hypoglycemia, defective islet glucagon secretion, but normal islet mass in mice with a disruption of the gastrin gene. Gastroenterology. 2003;125(4):1164-74.
Cao X, Flock G, Choi C, Irwin DM, Drucker DJ. Aberrant regulation of human intestinal proglucagon gene expression in the NCI-H716 cell line. Endocrinology. 2003;144(5):2025-33.
De Leon DD, Deng S, Madani R, Ahima RS, Drucker DJ, Stoffers DA. Role of endogenous glucagon-like peptide-1 in islet regeneration after partial pancreatectomy. Diabetes. 2003;52(2):365-71.
Drucker DJ. Glucagon-like peptide-1 and the islet beta-cell: augmentation of cell proliferation and inhibition of apoptosis. Endocrinology. 2003;144(12):5145-8.
Drucker DJ. Enhancing incretin action for the treatment of type 2 diabetes. Diabetes Care. 2003;26(10):2929-40.
Drucker DJ. Glucagon-like peptides: regulators of cell proliferation, differentiation, and apoptosis. Mol Endocrinol. 2003;17(2):161-71.
Drucker DJ. Therapeutic potential of dipeptidyl peptidase IV inhibitors for the treatment of type 2 diabetes. Expert Opin Investig Drugs. 2003;12(1):87-100.
During MJ, Cao L, Zuzga DS, Francis JS, Fitzsimons HL, Jiao X, et al. Glucagon-like peptide-1 receptor is involved in learning and neuroprotection. Nat Med. 2003;9(9):1173-9.
Estall JL, Drucker DJ. Dual regulation of cell proliferation and survival via activation of glucagon-like peptide-2 receptor signaling. J Nutr. 2003;133(11):3708-11.
Gros R, You X, Baggio LL, Kabir MG, Sadi AM, Mungrue IN, et al. Cardiac function in mice lacking the glucagon-like peptide-1 receptor. Endocrinology. 2003;144(6):2242-52.
Kim JG, Baggio LL, Bridon DP, Castaigne JP, Robitaille MF, Jette L, et al. Development and characterization of a glucagon-like peptide 1-albumin conjugate: the ability to activate the glucagon-like peptide 1 receptor in vivo. Diabetes. 2003;52(3):751-9.
Li Y, Hansotia T, Yusta B, Ris F, Halban PA, Drucker DJ. Glucagon-like peptide-1 receptor signaling modulates beta cell apoptosis. J Biol Chem. 2003;278(1):471-8.
Mayo KE, Miller LJ, Bataille D, Dalle S, Goke B, Thorens B, et al. International Union of PharmacologY XXXV. The glucagon receptor family. Pharmacol Rev. 2003;55(1):167-94.

(56) References Cited

OTHER PUBLICATIONS

Trinh DK, Zhang K, Hossain M, Brubaker PL, Drucker DJ. Pax-6 activates endogenous proglucagon gene expression in the rodent gastrointestinal epithelium. Diabetes. 2003;52(2):425-33.

Walsh NA, Yusta B, Dacambra MP, Anini Y, Drucker DJ, Brubaker PL. Glucagon-like peptide-2 receptor activation in the rat intestinal mucosa. Endocrinology. 2003;144(10):4385-92.

Yamamoto H, Kishi T, Lee CE, Choi BJ, Fang H, Hollenberg AN, et al. Glucagon-like peptide-1-responsive catecholamine neurons in the area postrema link peripheral glucagon-like peptide-1 with central autonomic control sites. J Neurosci. 2003;23(7):2939-46.

Pasquali L, Giannoukakis N, Trucco M. Induction of immune tolerance to facilitate beta cell regeneration in type 1 diabetes. Adv Drug Deliv Rev. 2008;60(2):106-13.

Ablamunits V, Sherry NA, Kushner JA, Herold KC. Autoimmunity and beta cell regeneration in mouse and human type 1 diabetes: the peace is not enough. Ann N Y Acad Sci. 2007;1103:19-32.

Gianani R. Beta cell regeneration in human pancreas. Semin Immunopathol. 2011;33(1):23-7.

Desgraz R, Bonal C, Herrera PL. beta-cell regeneration: the pancreatic intrinsic faculty. Trends Endocrinol Metab. 2011;22(1):34-43.

Nir T, Melton DA, Dor Y. Recovery from diabetes in mice by beta cell regeneration. J Clin Invest. 2007;117(9):2553-61.

Khalaileh A, Gonen-Gross T, Magenheim J, Nir T, Porat S, Salpeter S, et al. Determinants of pancreatic beta-cell regeneration. Diabetes Obes Metab. 2008;10 Suppl 4:128-35.

Cano DA, Rulifson IC, Heiser PW, Swigart LB, Pelengaris S, German M, et al. Regulated beta-cell regeneration in the adult mouse pancreas. Diabetes. 2008;57(4):958-66.

Suarez-Pinzon WL, Rabinovitch A. Combination therapy with a dipeptidyl peptidase-4 inhibitor and a proton pump inhibitor induces beta-cell neogenesis from adult human pancreatic duct cells implanted in immunodeficient mice. Cell Transplant. 2011;20(9):1343-9.

Eisenbarth SC, Williams A, Colegio OR, Meng H, Strowig T, Rongvaux A, et al. NLRP10 is a NOD-like receptor essential to initiate adaptive immunity by dendritic cells. Nature. 2012;484(7395):510-3.

Henao-Mejia J, Elinav E, Strowig T, Flavell RA. Inflammasomes: far beyond inflammation. Nat Immunol. 2012;13(4):321-4.

Henao-Mejia J, Elinav E, Jin C, Hao L, Mehal WZ, Strowig T, et al. Inflammasome-mediated dysbiosis regulates progression of NAFLD and obesity. Nature. 2012;482(7384):179-85.

Strowig T, Henao-Mejia J, Elinav E, Flavell R. Inflammasomes in health and disease. Nature. 2012;481 (7381):278-86.

Monte SV, Caruana JA, Ghanim H, Sia CL, Korzeniewski K, Schentag JJ, et al. Reduction in endotoxemia, oxidative and inflammatory stress, and insulin resistance after Roux-en-Y gastric bypass surgery in patients with morbid obesity and type 2 diabetes mellitus. Surgery. 2011.

Bahrami J, Longuet C, Baggio LL, Li K, Drucker DJ. Glucagon-like peptide-2 receptor modulates islet adaptation to metabolic stress in the ob/ob mouse. Gastroenterology. 2010;139(3):857-68.

Drucker DJ. Biologic actions and therapeutic potential of the proglucagon-derived peptides. Nat Clin Pract Endocrinol Metab. 2005;1(1):22-31.

Brubaker PL, Drucker DJ. Minireview: Glucagon-like peptides regulate cell proliferation and apoptosis in the pancreas, gut, and central nervous system. Endocrinology. 2004;145(6):2653-9.

Baggio LL, Huang Q, Brown TJ, Drucker DJ. Oxyntomodulin and glucagon-like peptide-1 differentially regulate murine food intake and energy expenditure. Gastroenterology. 2004;127(2):546-58.

Hsieh J, Longuet C, Maida A, Bahrami J, Xu E, Baker CL, et al. Glucagon-like peptide-2 increases intestinal lipid absorption and chylomicron production via CD36. Gastroenterology. 2009;137(3):997-1005, e1-4.

Hara T, Hirasawa A, Ichimura A, Kimura I, Tsujimoto G. Free fatty acid receptors FFAR1 and GPR120 as novel therapeutic targets for metabolic disorders. J Pharm Sci. 2011;100(9):3594-601.

Ichimura A, Hirasawa A, Poulain-Godefroy O, Bonneford A, Hara T, Yengo L, et al. Dysfunction of lipid sensor GPR120 leads to obesity in both mouse and human. Nature. 2012;483(7389):350-4.

Burcelim R, Da Costa A, Drucker D, Thorens B. Glucose competence of the hepatoportal vein sensor requires the presence of an activated glucagon-like peptide-1 receptor. Diabetes. 2001;50(8):1720-8.

Jeppesen PB, Sanguinetti EL, Buchman A, Howard L, Scolapio JS, Ziegler TR, et al. Teduglutide (ALX-0600), a dipeptidyl peptidase IV resistant glucagon-like peptide 2 analogue, improves intestinal function in short bowel syndrome patients. Gut. 2005;54(9):1224-31.

Wynne K, Park AJ, Small CJ, Patterson M, Ellis SM, Murphy KG, et al. Subcutaneous oxyntomodulin reduces body weight in overweight and obese subjects: a double-blind, randomized, controlled trial. Diabetes. 2005;54 (8):2390-5.

Crook MA, Tutt P, Pickup JC. Elevated serum sialic acid concentration in NIDDM and its relationship to blood pressure and retinopathy. Diabetes Care. Jan. 1993;16(1):57-60.

Dandona P, Aljada A, Bandyopadhyay A. Inflammation: the link between insulin resistance, obesity and diabetes. Trends Immunol. Jan. 2004;25(1):4-7.

Pickup JC, Mattock MB, Chusney GD, Burt D. NIDDM as a disease of the innate immune system: association of acute-phase reactants and interluken-6 with metabolic syndrome X. Diabetologia. Nov. 1997;40(11):1286-1292.

Wellen KE, Hotamisligil GS. Inflammation, stress, and diabetes. J Clin Invest. May 2005;115(5):1111-1119.

Ghanim H, Aljada A, Hofmeyer D, Syed T, Mohanty P, Dandona P. Circulating mononuclear cells in the obese are in a proinflammatory state. Circulation. Sep. 21, 2004;110(12):1564-1571.

Cani PD, Amar J, Iglesias MA, et al. Metabolic endotoxemia initiates obesity and insulin resistance. Diabetes. Jul. 2007;56(7):1761-1772.

Cummings DE, Overduin J, Foster-Schubert KE. Gastric bypass for obesity: mechanisms of weight loss and diabetes resolution. J Clin Endocrinol Metab. Jun. 2004;89(6):2608-2615.

Zhang H, Dibaise JK, Zuccolo A, et al. Human gut microbiota in obesity and after gastric bypass. Proc Natl Acad Sci U S A. Feb. 17, 2009;106(7):2365-2370.

Ghanim H, Abuaysheh S, Sia CL, et al. Increase in plasma endotoxin concentrations and the expression of Toll-like receptors and suppressor of cytokine signaling-3 in mononuclear cells after a high-fat, high-carbohydrate meal: implications for insulin resistance. Diabetes Care. Dec. 2009;32(12):2281-2287.

Deopurkar R, Ghanim H, Friedman J, et al. Differential effects of cream, glucose, and orange juice on inflammation, endotoxin, and the expression of Toll-like receptor-4 and suppressor of cytokine signaling-3. Diabetes Care. May 2010;33(5):991-997.

Chow JC, Young DW, Golenback DT, Christ WJ, Gusovsky F. Toll-like receptor-4 mediates lipopolysaccharide-induced signal transduction. J Biol Chem. Apr. 16, 1999;274(16):10689-10692.

Buchwald H, Avidor Y, Braunwald E, et al. Bariatric surgery: a systematic review and meta-analysis. JAMA. Oct. 13, 2004;292(14):1724-1737.

Pories WJ, Swanson MS, Macdonald KG, et al. Who would have thought it? An operation proves to be the most effective therapy for adult-onset diabetes mellitus. Ann Surg. Sep. 1995;222(3):339-350; discussion 350-332.

Schauer PR, Burguera B, Ikramuddin S, et al. Effect of laparoscopic Roux-en Y gastric bypass on type 2 diabetes mellitus. Ann Surg. Oct. 2003;238(4):467-484; discussion 484-465.

Sjostrom L, Lindroos AK, Peltonen M, et al. Lifestyle, diabetes, and cardiovascular risk factors 10 years after bariatric surgery. N Engl J Med. Dec. 23, 2004;351(26):2683-2693.

Caruana JA M, MN, Smith AD, Stawiasz KA, Kabakov E, Kabakov JM. Roux-en-Y gastric bypass by single incision mini-laparotomy: outcomes in 3300 consecutive patients. Obes Surg. 2011;21:820-824.

Andrews NC, Faller DV. A rapid micropreparation technique for extraction of DNA-binding proteins from limiting Numbers of mammalian cells. Nucleic Acids Res. 1991;19(9):2499.

(56) References Cited

OTHER PUBLICATIONS

Pournaras DJ, Osborne A, Hawkins SC, et al. Remission of type 2 diabetes after gastric bypass and banding: mechanisms and 2 year outcomes. Ann Surg. Dec. 2010;252(6):966-971.
Dandona P, Aljada A, Chaudhri A, Mohanty P, Garg R. Metabolic syndrome: a comprehensive perspective based on interactions between obesity, diabetes, and inflammation. Circulation. Mar. 22, 2005;111(11):1448-1454.
Iaconelli A, Panunzi S, De Gaetano A, et al. Effects of bilio-pancreatic diversion on diabetic complications: a 10-year follow-up. Diabetes Care. Mar. 2011;34(3):561-567.
Campos GM, Rabl C, Roll GR, et al. Better weight loss, resolution of diabetes, and quality of life for laparoscopic gastric bypass vs banding: results of a 2-cohort pair-matched study. Arch Surg. Feb. 2011;146(2):149-155.
Lee WJ, Chong K, Ser KH, et al. Gastric bypass vs sleeve gastrectomy for type 2 diabetes mellitus: a randomized controlled trial. Arch Surg. Feb. 2011;146(2):143-148.
Ochner CN, Gibson C, Shanik M, Goel V, Geliebter A. Changes in neurohormonal gut peptides following bariatric surgery. Int J Obes (Lond). Feb. 2011;35(2):153-166.
Orlando FA, Goncalves CG, George ZM, Halverson JD, Cunningham PR, Meguid MM. Neurohormonal pathways regulating food intake and changes after Roux-en-Y gastric bypass. Surg Obes Relat Dis. Sep.-Oct. 2005;1(5):486-495.
Batterham RL, Ffytche DH, Rosenthal JM, et al. PYY modulation of cortical and hypothalamic brain areas predicts feeding behaviour in humans. Nature. Nov. 1, 2007;450(7166):106-109.
Doucet E, Cameron J. Appetite control after weight loss: what is the role of bloodborne peptides? Appl Physiol Nutr Metab. Jun. 2007;32(3):523-532.
Falken Y, Hellstrom PM, Holst JJ, Naslund E. Changes in Glucose Homeostasis after Roux-en-Y Gastric Bypass Surgery for Obesity at Day Three, Two Months, and One Year after Surgery: Role of Gut Peptides. J Clin Endocrinol Metab. Jul. 2011;96(7):2227-2235.
Tripathy D, Mohanty P, Dhindsa S, et al. Elevation of free fatty acids induces inflammation and impairs vascular reactivity in healthy subjects. Diabetes. Dec. 2003;52(12):2882-2887.
Clark JM, Alkhuraishi AR, Solga SF, Alli P, Diehl AM, Magnuson TH. Roux-en-Y gastric bypass improves liver histology in patients with non-alcoholic fatty liver disease. Obes Res. Jul. 2005;13(7):1180-1186.
Wang RT, Koretz RL, Yee HF, Jr. Is weight reduction an effective therapy for nonalcoholic fatty liver? A systematic review. Am J Med. Nov. 2003;115(7):554-559.
Polak JM, Bloom S, Coulling I, Pearse AG. Immunofluorescent localization of enteroglucagon cells in the gastrointestinal tract of the dog. Gut. 1971;12(4):311-8.
Polak JM, Bloom S, Coulling I, Pearse AG. Immunofluorescent localization of secretin and enteroglucagon in human intestinal mucosa. Scand J Gastroenterol. 1971;6(8):739-44.
Maljaars PW, Peters HP, Mela DJ, Masclee AA. Ileal brake: a sensible food target for appetite control. A review. Physiol Behav. 2008;95(3):271-81.
Van Citters GW, Lin HC. Ileal brake: neuropeptidergic control of intestinal transit. Curr Gastroenterol Rep. 2006;8(5):367-73.
Schirra J, Goke B. The physiological role of GLP-1 in human: incretin, ileal brake or more? Regul Pept. 2005;128(2):109-15.
Dobson CL, Davis SS, Chauhan S, Sparrow RA, Wilding IR. The effect of ileal brake activators on the oral bioavailability of atenolol in man. Int J Pharm. 2002;248(1-2):61-70.
Van Citters GW, Lin HC. The ileal brake: a fifteen-year progress report. Curr Gastroenterol Rep. 1999;1(5):404-9.
Vu MK, Nouwens MA, Biemond I, Lamers CB, Masclee AA. The osmotic laxative magnesium sulphate activates the ileal brake. Aliment Pharmacol Ther. 2000;14(5):587-95.
Dobson CL, Davis SS, Chauhan S, Sparrow RA, Wilding IR. The effect of oleic acid on the human ileal brake and its implications for small intestinal transit of tablet formulations. Pharm Res. 1999;16(1):92-6.
Pironi L, Stanghellini V, Miglioli M, et al. Fat-induced ileal brake in humans: a dose-dependent phenomenon correlated to the plasma levels of peptide YY. Gastroenterology. 1993;105(3):733-9.
Soper NJ, Chapman NJ, Kelly KA, Brown ML, Phillips SF, Go VL. The 'ileal brake' after ileal pouch-anal anastomosis. Gastroenterology. 1990;98(1):111-6.
Spiller RC, Trotman IF, Adrian TE, Bloom SR, Misiewicz JJ, Silk DD. Further characterisation of the 'ileal brake' reflex in man—effect of ileal infusion of partial digests of fat, protein, and starch on jejunal motility and release of neurotensin, enteroglucagon, and peptide YY. Gut. 1988;29(8):1042-51.
Milk fat, diarrhoea, and the ilea brake. Lancet. 1986;1(8482):658.
Spiller RC, Trotman IF, Higgins BE, et al. The ileal brake—inhibition of jejunal motility after ileal fat perfusion in man. Gut. 1984;25(4):365-74.
Tamburrano G, Mauceri M, Lala A, Tonelli F, Leonetti F, Andreani D. Plasma levels of glucagon-like polypeptides in gastrectomized patients transformed from Billroth II into Billroth I. Horm Metab Res. 1982;14(12):642-5.
Holst JJ. Glucagonlike peptide 1: a newly discovered gastrointestinal hormone. Gastroenterology. 1994;107(6):1848-55.
Holst JJ, Bersani M, Johnsen AH, Kofod H, Hartmann B, Orskov C. Proglucagon processing in porcine and human pancreas. J Biol Chem. 1994;269(29):18827-33.
Williams DL. Minireview: finding the sweet spot: peripheral versus central glucagon-like peptide 1 action in feeding and glucose homeostasis. Endocrinology. 2009;150(7):2997-3001.
Fields AV, Patterson B, Karnik AA, Shannon RP. Glucagon-like peptide-1 and myocardial protection: more than glycemic control. Clin Cardiol. 2009;32(5):236-43.
Abu-Hamdah R, Rabiee A, Meneilly GS, Shannon RP, Andersen DK, Elahi D. Clinical review: The extrapancreatic effects of glucagon-like peptide-1 and related peptides. J Clin Endocrinol Metab. 2009;94(6):1843-52.
Damholt AB, Buchan AM, Kofod H. Glucagon-like-peptide-1 secretion from canine L-cells is increased by glucose-dependent-insulinotropic peptide but unaffected by glucose. Endocrinology. 1998;139(4):2085-91.
Gutzwiller JP, Drewe J, Goke B, et al. Glucagon-like peptide-1 promotes satiety and reduces food intake in patients with diabetes mellitus type 2. Am J Physiol. 1999;276(5 Pt 2):R1541-4.
Gutzwiller JP, Goke B, Drewe J, et al. Glucagon-like peptide-1: a potent regulator of food intake in humans. Gut. 1999;44(1):81-6.
Astrup A, Rossner S, Van Gaal L, et al. Effects of liraglutide in the treatment of obesity: a randomised, double-blind, placebo-controlled study. Lancet. 2009;374(9701):1606-16.
Peters CT, Choi YH, Brubaker PL, Anderson GH. A glucagon-like peptide-1 receptor agonist and an antagonist modify macronutrient selection by rats. J Nutr. 2001;131(8):2164-70.
Choi YH, Anderson GH. An interaction between hypothalamic glucagon-like peptide-1 and macronutrient composition determines food intake in rats. J Nutr. 2001;131(6):1819-25.
Burcelin R, Da Costa A, Drucker D, Thorens B. Glucose competence of the hepatoportal vein sensor requires the presence of an activated glucagon-like peptide-1 receptor. Diabetes. 2001;50(8):1720-8.
Drucker DJ. Development of glucagon-like peptide-1-based pharmaceuticals as therapeutic agents for the treatment of diabetes. Curr Pharm Des. 2001;7(14):1399-412.
Lovshin J, Estall J, Yusta B, Brown TJ, Drucker DJ. Glucagon-like peptide (GLP)-2 action in the murine central nervous system is enhanced by elimination of GLP-1 receptor signaling. J Biol Chem. 2001;276(24):21489-99.
Boushey RP, Yusta B, Drucker DJ. Glucagon-like peptide (GLP)-2 reduces chemotherapy-associated mortality and enhances cell survival in cells expressing a transfected GLP-2 receptor. Cancer Res. 2001;61(2):687-93.
Drucker DJ. Minireview: the glucagon-like peptides. Endocrinology. 2001;142(2):521-7.
Adrian TE, Savage AP, Fuessl HS, Wolfe K, Besterman HS, Bloom SR. Release of peptide YY (PYY) after resection of small bowel, colon, or pancreas in man. Surgery. 1987;101(6):715-9.

(56) References Cited

OTHER PUBLICATIONS

Savage AP, Adrian TE, Carolan G, Chatterjee VK, Bloom SR. Effects of peptide YY (PYY) on mouth to caecum intestinal transit time and on the rate of gastric emptying in healthy volunteers. Gut. 1987;28(2):166-70.

Balas B, Baig MR, Watson C, et al. The dipeptidyl peptidase IV inhibitor vildagliptin suppresses endogenous glucose production and enhances islet function after single-dose administration in type 2 diabetic patients. J Clin Endocrinol Metab. 2007;92(4):1249-55.

Qualmann C, Nauck MA, Holst JJ, Orskov C, Creutzfeldt W. Insulinotropic actions of intravenous glucagon-like peptide-1 (GLP-1) [7-36 amide] in the fasting state in healthy subjects. Acta Diabetol. 1995;32(1):13-6.

Holst JJ. Glucagon-like peptide-1, a gastrointestinal hormone with a pharmaceutical potential. Curr Med Chem. 1999;6(11):1005-17.

Meier JJ, Gallwitz B, Salmen S, et al. Normalization of glucose concentrations and deceleration of gastric emptying after solid meals during intravenous glucagon-like peptide 1 in patients with type 2 diabetes. J Clin Endocrinol Metab. 2003;88(6):2719-25.

Chaudri OB, Wynne K, Bloom SR. Can gut hormones control appetite and prevent obesity? Diabetes Care. 2008;31 Suppl 2:S284-9.

Nilsson AC, Ostman EM, Holst JJ, Bjorck IM. Including indigestible carbohydrates in the evening meal of healthy subjects improves glucose tolerance, lowers inflammatory markers, and increases satiety after a subsequent standardized breakfast. J Nutr. 2008;138(4):732-9.

McLean PS, Energy balance with weight loss and relapse Am.J. Physiology,2004.

Wadden TA, et al. One year weight losses in the look-ahead study: Factors associated with success. Obesity (2009) 17,713-722.

FDA Communication Aug. 24, 2009 Early Communication about an Ongoing Safety Review Orlistat (marketed as Alli and Xenical).

Venables WN, Smith DM, et al. An Introduction to R: A Programming Environment for Data Analysis and Graphics. Mar. 30, 2012, version 2.15.0. http://www.R-project.org. Vienna, Austria.

Mazmanian SK. The Microbial Health Factor. http://www.the-scientist.com/?articles.view/articleNo/27565/title/Microbial-Health-Factor/, 2009.

Halmi KA, Mason E, Falk JR, Stunkard A. Appetitive behavior after gastric bypass for obesity. International Journal of Obesity, 1981;5:457-464.

Hatoum IJ, Greenawalt DM, Cotsapas C, Reitman ML, Daly MJ, Kaplan LM. Heritability of the Weight Loss Response to Gastric Bypass Surgery. J Clin Endocrinol Metab, 2011;96(10):E1630-E1633.

Kenler HA, Brolin RE, Cody RP. Changes in eating behavior after horizontal gastroplasty and Roux-en-Y gastric bypass. Am J Clin Nutr, 1990;52:87-92.

Koch L. Genotype determines weight loss after bariatric surgery. Nature Reviews Endocrinology, 2011;7:630.

Laferrere B, Teixeira J, McGinty J, et al. Effect of Weight Loss by Gastric Bypass Surgery Versus Hypocaloric Diet on Glucose and Incretin levels in Patients with Type 2 Diabetes. J Clin Endocrinol Metab, 2008;93(7):2479-2485.

Lamia KA, Evans RM. Tick, tock, a beta-cell clock. Nature, 2010;466(29):571-572.

Le Roux CW, Aylwin S, Batterham RL, et al. Gut Hormone Profiles Following Bariatric Surgery Favor and Anorectic State, Facilitate Weight Loss, and Improve Metabolic Parameters. Ann Surg, 2006;243:108-114.

Maciejewski ML, Livingston EH, Smith VA, Kavee LC, Henderson WC, Arterburn DE. Survival Among High-Risk Patients After Bariatric Surgery. JAMA, 2011;305(23):2419-2426.

Martin MT, Azpiroz F, Malagelada JR. Ileal Brake Failure in Streptozotocin-Induced Diabetic Rat. Scand J Gastroenterol, 2004;5:423-427.

Blackburn GL. Medications That May Cause Weight Gain and Their Potential Alternatives. http://soundnutritionwv.com/yahoo_site_admin/assets/docs/medications_that_cause_weight_gain.68135518.pdf, 2003.

Meirelles K, Ahmed T, Culnan DM, Lynch CJ, Lang CH, Cooney RN. Mechanisms of Glucose Homeostasis After Roux-en-Y Gastric Bypass Surgery in the Obese, Insulin-Resistant Zucker Rat. Ann Surg, 2009;249:277-285.

McKillop AM, Flatt PR. Emerging Applications of Metabolomic and Genomic Profiling in Diabetic Clinical Medicine. Diabetes Care, 2011;34(12):2624-2630.

Brugere JF, Mihajlovski A, Missaoui M, Peyret P. Tools for Stools: The Challenge of Assessing Human Intestinal Microbiota Using Molecular Diagnostics. Expert Rev Mol Diagn. 2009;9(4):353-65.

Mohn A, Catino M, Capanna R, Giannini C, Marcovecchio M, Chiarelli F. Increased Oxidative Stress in Prepubertal Severely Obese Children: Effect of a Dietary Restriction-Weight Loss Program. J Clin Endocrinol Metab, 2005;90(5):2653-2658.

Ball WL, et al. Guiding Principles for Diabetes Care: For Health Care Professionals. National Diabetes Education Program, http://www.ndep.nih.gov/media/guidprin_hc_eng.pdf, Apr. 2009.

Flum DR, Belle SH, King WC, et al. Perioperative Safety in the Longitudinal Assessment of Bariatric Surgery. N Engl J Med, 2009;361(5):445-454.

Robinson MK. Surgical Treatment of OBesity—Weighing the Facts. N Engl J Med, 2009;361(5):520-521.

World Health Organization. Obesity and overweight. http://www.who.int/mediacentre/factsheets/fs311/en/print.html, 2006.

Stokowski LA. Weight Loss Drugs: What Works? http://www.medscape.com/viewarticle/733585, 2010.

Fox M. New gene test may help you pick your diet—report. Thomson Reuters, 2010. http://www.reuters.com/article/2010/03/03/us-diet-genes-idUSTRE6224UV20100303.

Olbers T, Bjorkman S, Lindroos A, Maleckas A, Lonn L, Sjostrom L, Lonroth H. Body Composition, Dietary Intake, and Energy Expenditure After Laparoscopic Roux-en-Y Gastric Bypass and Laparoscopic Vertical Banded Gastroplasty. Ann Surg, 2006;244(5):715-722.

Orrhage K, Sjostedt S. Nord CE. Effect of supplements with lactic acid bacteria and oligofructose on the intestinal microflora during administration of cefpodoxime proxetil. J Antimicrob Chemother, 2000;46(4):603-612.

Owan T, Avelar E, Morley K, et al. Favorable Changes in Cardiac Geometry and Function Following Gastric Bypass Surgery. Journal of the American College of Cardiology, 2011;57(6):732-739.

Pniewski T, Kapusta J, Bociagg P, et al. Plant expression, lyophilisation and storage of HBV medium and large surface antigens for a prototype oral vaccine formulation. Plant Cell Rep, 2012;31:585-595.

Polyzogopoulou EV, Kalfarentzos F, Vagenakis AG, Alexandrides TK. Restoration of Euglycemia and Normal Acute Insulin Response to Glucose in Obese Subjects With Type 2 Diabetes Following Bariatric Surgery. Diabetes, 2003;52:1098-1103.

Qin J, Li R, Raes J, et al. A human gut microbial gene catalogue established by metagenomic sequencing. Nature, 2010;464(5):59-67.

Rao RS, Yanagisawa R, Kini S. Insulin resistance and bariatric surgery. Obesity Reviews, 2011;13(4):316-328.

Reed MA, Poris WJ, Chapman W, et al. Roux-en-Y Gastric Bypass Corrects Hyperinsulinemia Implications for the Remission of Type 2 Diabetes. J Clin Endocrinol Metab, 2011;96(8):2525-2531.

Requarth JA, Burchard KW, Colacchio TA, et al. Long-term morbidity following jejunoileal bypass: The continuing need for surgical reversal. Arch Surg,1995;130:318-325.

Riedl M, Vila G, Maier C, et al. Plasma Osteopontin Increases After Bariatric Surgery and Correlates with Markers of Bone Turnover But Not with Insulin Resistance. Journal of Clinical Endocrinology & Metabolism, 2008;93 (6):2307-2312.

Rubino F, Forgione A, Cummings DE, et al. The Mechanism of Diabetes Control After Gastrointestinal Bypass Surgery Reveals a Role of the Proximal Small Intestine in the Pathophysiology of Type 2 Diabetes. Ann Surg, 2006;244:741-749.

(56) References Cited

OTHER PUBLICATIONS

Ingelfinger JR. Bariatric Surgery in Adolescents. N Engl J Med, 2011;365(15):1365-1367.
Scwarz PE, Greaves CJ, Lindstro J, Yates T, Davies MJ. Nonpharmacological interventions for the prevention of type 2 diabetes mellitus. Nature Reviews Endocrinology, 2012;8:363-373.
Moss L. Scots unlock secrets of diabetes drug—and hopes for future. The Scotsman, Dec. 28, 2010.
Scruggs DM, Buffington C, Cowan G. Taste Acuity of the Morbidly Obese before and after gastric Bypass Surgery. Obesity Surgery, 1994;4:24-28.
Vastag B. Stomach surgery more effective than medicine for diabetes, studies find. The Washington Post, Mar. 26, 2012.
Waknine Y. Diabetes Risk Increased by 3 Independent Factors. www.medscape.com/viewarticle/760732_print, 2012.
Mackins H. Data Show that a Decrease in PreDx(R) Diabetes Risk Score (DRS) is Correlated with Lowered Risk of Diabetes. Jun. 27, 2011 http://www.clinicaspace.com/news_print.aspx?NewsEntityID=225399.
Mackins H. Structure House Presents Data Correlating Weight Loss, Reduction of Diabetes Risk Factors and Lowering of PreDx(R) Diabetes Risk Score. http://www.clinicaspace.com/news_printaspx?NewsEntityID=225397, 2011.
Thomas JR, Marcus E. High and Low Fat Food Selection with Reported Frequency Intolerance Following Roux-en-Y Gastric Bypass. Obes Surg, 2008;18:282-287.
Thomas G, Sehgal AR, Kashyap SR, Sriviva TR, Kirwan JP, Navaneethan SD. Metabolic Syndrome and Kidney Disease: A Systematic Review and Meta-Analysis. Clin J Am Soc Nephrol, 2011;6(10):2364-2373.
Tiano JP, Mauvais-Jarvis F. Importance of oestrogen receptors to preserve functional beta-cell mass in diabetes. Nature Reviews Endocrinology, 2012;8:342-351.
Torquati A, Lutfi R, Abumrad N, Richards WO. Is Roux-en-Y Gastric Bypass Surgery the Most Effective Treatment for Type 2 Diabetes Mellitus in Morbidly Obese Patients? J Gastro Surg, 2005;9(8):1112-1118.
Tulipani S, Llorach R, Jauregui O, et al. Metabolomics Unveils Urinary Changes in Subjects with Metabolic Syndrome following 12-Week Nut Consumption. J Proteome Res, 2011;10:5047-5058.
USDA Database for the Added Sugars Content of Selected Foods. Nutrient Data Laboratory, Beltsville Human Nutrition Research Center, Agricultural Research Service, US Department of Agriculture. Beltsville, Maryland, Feb. 2006.
Gebhardt S, Thomas RG. Nutritive Value of Foods. Home and Garden Bulletin 72, Oct. 2002. Beltsville, Maryland.
Vaarala O, Yki-Jarvinen H. Should we treat infection or inflammation to prevent T2DM? Nature Reviews Endocrinology, 2012;8:323-325.
Duckworth W, Abraira C, Moritz T, et al. Glucose Control and Vascular Complications in Veterans with Type 2 Diabetes. N Engl J Med, 2009;360(2):129-139.
Fink RI, et al. Mechanisms of Insulin Resistance in Aging. The Journal of Clinical Invesitgation. 1983;71:1523-1535.
Warram JH, et al. Slow Glucose Removal Rate and Hyperinsulinemia Precede the Development of Type II Diabetes in the Offspring of Diabetic Parents. Annals of Internal Medicine, 1990;113:909-915.
Eriksson J, et al. Early Metabolic Defects in Persons At Increased Risk for Non-Insulin-Dependent Diabetes Mellitus. The New England Journal of Medicine, 1989;321(6):337-343.
Fabbrini E, et al. Metabolically normal obese people are protected from adverse effects following weight gain. J Clin Invest, 2014:1-9.
Madsbad S, Holst JJ. GLP-1 as a Mediator in the Remission of Type 2 Diabetes After Gastric Bypass and Sleeve Gastrectomy Surgery. Diabetes, 2014;63:3172-3174.
Vetter ML, Cardillo S, Rickels MR. Iqbal N. Narrative Review; Effect of Bariatric Surgery on Type 2 Diabetes Mellitus. Ann Intern Med, 2009;150:94-103.
Boyles S. Study Casts Doubt on Weight Loss Supplements; Researchers Say 9 Dietary Supplements Are Not Effective for Cutting Weight. www.webmd.com, Jul. 12, 2010.
Health Day. Weight Loss Surgery May Help Diabetes. Health Day, Jan. 6, 2012. http://health.usnews.com/health-news/diet-fitness/diabetes/articles/2012/01/06/weight-loss-surgery-may-help-diabetes.
Lowes R. Weight-Management Helps Regular Users the Most. J Med Internet Res. Jul. 27, 2010. http://www.medscape.com/viewarticle/725889.
Mitchell K. Which Weight Loss Products are Most effective? The Diet Advisors, Jan. 2011. www.thedietadvisors.com/WeightLossProducts.
Woodmansey EJ. Intestinal bacteria and ageing. Journal of Applied Microbiology, 2007;102:1178-1186.
Yang X, Ongusaha PP, Miles PD, et al. Phosphoinositide signalling links O0GlcNAc transferase to insulin resistance. Nature, 2008;451(21):964-970.
Schaur PR, et al. Bariatric Surgery versus Intensive Medical Therapy in Obese Patients with Diabetes. N Engl J Med, 2012;366(17):1567-1576.
Buchwald H, et al. Bariatric Surgery: A Systematic Review and Meta-analysis. JAMA, 2004;293(14):1724-1728.
Cani PD, et al. Metabolic Endotoxemia Initiates Obesity and Insulin Resistance. Diabetes, 2007;56:1761-1772.
Cummings DE, Overduin J, Foster-Schubert KE. Gastric Bypass for Obesity: Mechanisms of Weight Loss and Diabetes Resolution. J Clin Endocrinol Metab, 2004;89(6):2608-2615.
Drucker, DJ. Glucagon-Like Peptide-1 and the Islet beta-Cell: Augmentation of Cell Proliferation and Inhibition of Apoptosis. Endocrinology, 2003;144(12):5145-5148.
Food and Nutrition Board. Dietary Reference Intakes for Energy, Carbohydrate, Fiber, Fat, Fatty Acids, Cholesterd, Protein, and Amino Acids. Institute of Medicine of the National Academies, The National Academies Press. Washington D.C., 2005.
Ochner CN, et al. Changes in neurohormonal gut peptides following bariatric surgery. International Journal of Obesity, 2011;35:153-166.
Ghanim H, et al. Increase in Plasma Endotoxin Concentration and the Expression of Toll-Like Receptors and Suppressor of Cytokine Signaling-3 in Mononuclear Cells After a High-Fat, High-Carbohydrate Meal, Diabetes Car, 2009;32(12):2281-2287.
Henao-Mejia J, et al. Inflammasome-mediated dysbiosis regulates progression of NAFLD and obesity. Nature, 2012;482:179-186.
Jayasena CH, Bloom SR. Role of Gut Hormones in Obesity. Endocrinol Metab Clin N Am, 2008;37:769-787.
Morinigo R, et al. Glucagon-Like Peptide-1, Peptide YY, Hunger and Satiety after Gastric Bypass Surgery in Morbidly Obese Subjects. Journal of Clinical Endocrinology & Metabolism, 2006;91(5):1735-1740.
Pories WJ, et al. Who Would Have Thought It? An Operation Proves to Be the Most Effective Therapy for Adult-Onset Diabetes Mellitus. Annals of Surgery, 1995;222(3):339-352.
Baumann K. Stem cells: Making Fat. Nature Reviews Molecular Cell Biology, 2012;13:62-63.
Schauer PR, et al. Effect of Laparoscopic Roux-En Y Gastric Bypass on Type 2 Diabetes Mellitus. Ann Surg, 2003;238:467-485.
Sjostrom L, et al. Lifestyle, Diabetes, and Cardiovascular Risk Factors 10 Years after Bariatric Surgery. N Engl J Med, 2004;351:2683-2693.
Strowig T, et al. Inflammasomes in health and disease. Nature, 2012;481:278-286.
Wang SS. Childhood Obesity Linked to Heart Risk. The Wall Street Journal, Mar. 1, 2010.
Yang X, et al. Phosphoinositide signalling links O-GlcNAc transferase to insulin resistance. Nature, 2008;451:964-970.
Zhang H, et al. Human gut microbiota in obesity and after gastric bypass. PNAS, 2009;106(7):2365-2370.
Nainggolan L, Barclay L. Bariatric Surgery Beats Standard Therapy in Obese Diabetics. www.medscape.com, Mar. 26, 2012.
Nichols, GA. Bariatric Surgery to "Treat" Diabetes: Worth the Costs? www.medscape.com, Oct. 12, 2010.
Gerstein HC, Miller ME, Byington RP, et al. Effects of Intensive Glucose Lowering in Type 2 Diabetes. N Engl J Med, Jun. 12, 2008;358(24):2545-2559.

(56) References Cited

OTHER PUBLICATIONS

Stiles S, Added Sugars in Diet Linked to Higher Triglycerides, Lower HDL-C in NHANES Data. www.medscape.com, Apr. 21, 2010.
New drug zaps fat cells in monkeys. Nov. 10, 2011, http://sg.news.yahoo.com/drug-zaps-fat-cells-monkeys-134821391.html.
Barclay L. Bariatric Surgery in Severly Obese Adolescents Debated. www.medscape.com, May 7, 2010.
Patel A, MacMahon S, Chalmers J, et al. Intensive Blood Glucose Control and Vascular Outcomes in Patients with Type 2 Diabetes. N Engl J Med, Jun. 12, 2008;358(24):2560-2572.
Al-Attas OS, Al-Daghri NM, Al-Rubeaan K, Da Silva NF, Sabico SL, Kumar S, McTernan PG, Harte AL. Changes in endotoxin levels in T2DM subjects on anti-diabetic therapies. Cardiovascular Diabetology, 2009;8 (20):1-10.
Ashrafian H, Le Roux, CW, Darzi A, Athanasiou T. Effects of Bariatric Surgery on Cardiovascular Function. Circulation. 2008;118:2091-2102.
Mingrone G, Panunzi S, De Gaetano A, et al. Bariatric Surgery versus Conventional Medical Therapy for Type 2 Diabetes. N Engl J Med 2012; 366:1577-1585.
Nainggolan L. Bariatric Surgery Does Not Improve Survival. www.medscape.com, Jun. 13, 2011.
Czupryniak L, Strzelczyk J, Cypryk K, et al. Gastric Bypass Surgery in Severely Obese Type 1 Diabetic Patients. Diabetes Care, Oct. 2004;27(10):2561-2562.
O'Riordan M. Bariatric Surgery Fails to Reduce Risk of MI Long Term. www.medscape.com, Oct. 28, 2009.
Miras AD, Le Roux CW. Bariatric surgery and taste: novel mechanisms of weight loss. Current Opinion in Gastroenterology 2010;26:140-145.
Doheny K, Bariatric Surgery Helps People Who Are Less Obese. www.webmd.com, Jun. 16, 2011.
Gagnon L. ASMBS 2009: Preoperative Status Affects Long-Term Outcome of Gastric Bypass Surgery in Diabetics. www.medscape.com, Jun. 25, 2009.
Bikman BT, Zheng D, Pories W, et al. Mechanism for Improves Insulin Sensitivity after Gastric Bypass Surgery. J Clin Endocrinol Metab 2008;91(12):4656-4663.
Bloom SR, Kuhajda FP, Laher I, Pi-Sunyer X, Ronnett GV, Tan T, Weigle DS. The Obesity Epidemic, Pharmacological Challenges. molecular interventions 2008;8(2):82-98.
Breen DM, Rasmussen BA, Kokorovic A, Mang R, Cheung G, Lam T. Jejunal nutrient sensing is required for duodenal-jejunal bypass surgery to rapidly lower glucose concentrations in uncontrolled diabetes. Nature Medicine, 2012;18:950-955.
Brown EK, Settle EA, Van Rij AM. Food intake patterns of gastric bypass patients. Journal of the American Dietetic Association, May 1982;80:437-443.
Brun P, Castagliuolo I, Di Leo V, Buda A, Pinzani M, Palu G, Martines D. Increased intestinal permeability in obese mice: new evidence in the pathogenesis of nonalcoholic steatohepatitis. AJP Gastrointest Liver Physiol 2007;292:G518-G525.
Cani PD, Possemiers S, Van De Wiele T, et al. Changes in gut microbiota control inflammation in obese mice through a mechanism involving GLP-2-driven improvement of gut permeability. Gut 2009;58:1091-1103.
Cani PD, Bibiloni R, Knauf C, Waget A, Neyrinck AM, Delzenne NM, Burcelin R. Changes in Gut Microbiota Control Metabolic Endotoxemia-Induced Inflammation in High-Fat Diet-Induced Obesity and Diabetes in Mice. Diabetes, Jun. 2008;57:1470-1481.
Amar J, Burcelin R, Ruidavets JB, et al. Energy intake is associated with endotoxemia in apparently healthy men. Am J Clin Nutr 2008;87:1219-1223.
Cani PD, Neyrinck AM, Fava F, Knauf C, Burcelin RG, Tuohy KM, Gibson GR, Delzenne NM. Selective increases of bifidobacteria in gut microflora improve high-fat-diet-induced diabetes in mice through a mechanism associated with endotoxaemia. Biabetologia 2007;50:2374-2383.
Fernandez-Real JM, Perez Del Pulgar S, Luche E, et al. CD14 Modulates Inflammation-driven Insulin Resistance. Diabetes 2011;60(8):2179-2186.
Chaudhry MZ, Wang JH, Blankson S, Redmond HP. Statin (Cerivastatin) Protects Mice Against Sepsis-Related Death via Reduced Proinflammatory Cytokines and Enhanced Bacterial Clearance. Surgical Infections 2009;9 (2)183-194.
Xia X, Weng J. Targeting metabolic syndrome: Candidate natural agents. Journal of Diabetes 2010;2:243-249.
Creely SJ, McTernan PG, Kusminski CM, et al. Lipopolysaccharide activates an innate immune system response in human adipose tissue in obesity and type 2 diabetes. Am J Physiol Endocrinol Metab 2007;292:740-747.
D'Adamo E, Marcovecchio ML, Giannini C, Capanna R, Impicciatore M, Chiarelli F, Mohn A. The possible role of liver steatosis in defining metabolic syndrome in prepubertal children. Metab Clin & Exper 2010;59:671-676.
D'Adamo E, Giannini C, Chiavaroli V, De Giorgis T, Verrotti A, Chiarelli F, Mohn A. What Is the Significance of Soluble and Endogenous Secretory Receptor for Advanced Glycation End Products in Liver Steatosis in Obese Prepubertal Children. Antioxidants & Redox Signaling, 2011;14(6):1167-1172.
Chaudhuri A, Ghanim H, Vora M, Korzeniewski K, Abuaysheh S, Makdissi A, Dandona P. Exenatide Exerts a Potent Anti-inflammatory Action. J Clin Endoclinical Metab. Jan. 2010;97(1):Abstract.
Edelson E. Popular Diet Plans Can Unclog Arteries. www.healthday.com, May 4, 2010.
Melda, D.J. Novel food technologies: enhancing appetite control in liquid meal replacers. Obesity 2006, 14:179S-181S.
Zheng D, Ionu V, Mooradian V, Stefanovski, Bergman RN. Portal glucose infusion-glucose clamp measures hepatic influence on postprandial systemic glucose appearance as well as whole body glucose disposal. Am J Physiol Endocrinol Metab 2010;298:E346-E353.
Johnson K, Edgerton DS, Rodewalk T, Scott M, Farmer B, Neal D, Cherrington AD. Intraportally delivered GLP-1, in the presence of hyperglycemia induced via peripheral glucose infusion, does not change whole body glucose utilization. Am J physiol Endocrinol Metab 2008;294:E380-E384.
Field B, Wren AM, Cooke D, Bloom SR. Gut Hormones as Potential New Targets for Appetite Regulation and the Treatment of Obesity. Drugs 2008;68(2):147-163.
Naik G. Hungry? Your Stomach Really Does Have a Mind of Its Own. www.wsj.com, Jan. 25, 2011.
Giannini C, De Giogis T, Scarinci A, Cataldo I, Marcovecchio ML, Chiarelli F, Mohn A. Increased carotid intima-media thickness in prepubertal children with constitutional leanness and sever obesity: the speculative role of insulin sensitivity, oxidant status, and chronic inflammation. Euro J Endocrin 2009;161:73-80.
Giannini C, Santoro N, Caprio S, et al. The Triglyceride-to-HDL Cholesterol Ratio. Diabetes Care, 2011;34:1869-1874.
Giannini C, Weiss R, Cali A, Bonadonna R, Santoro N, Pierpont B, Shaw M, Caprio S. Evidence for early defects in insulin sensitivity and secretion before the onset of glucose dysregulation in obese youths; a longitudinal study. Diabetes, 2012;61(3):606-614.
Vilsboll et al. Incretin Secretion in Diabetes Mellitus. J Clin Endocrinol Metab, 2003;88(6):2706-2713.
Guidone C, Manco M, Valera-Mora E, et al. Mechanisms of Recovery From Type 2 Diabetes After Malabsorptive Bariatric Surgery. Diabetes, 2006;55:2025-2031.
Hood M. Study raises hope for gut disease cures. news.yahoo.com, Mar. 3, 2010.
Verdich C, et al. A Meta-Analysis of the Effect of Glucagon-Like Peptide-1 (7-36) Amide on Ad Libitum Energy Intake in Humans. The Journal of Clinical Endocrinology & Metabolism, 2001;86(9):4382-4389.
Naslund E, et al. Energy intake and appetite are suppressed by glucagon-like peptide-1 (GLP-1) in obese men. International Journal of Obesity, 1999;23:304-311.

(56) References Cited

OTHER PUBLICATIONS

Gutzwiller JP, et al. Glucagon-like peptide-1 promotes satiety and reduces food intake in patients with diabetes mellitus type 2. The American Physiological Society, 1999:R1541-R1544.

Bryant MG, Bloom SR. Distribution of the gut hormones in the primate intestinal tract. Gut, 1979;20:653-659.

Festa A, et al. Differences in Insulin Resistance in Nondiabetic Subjects with Isolated Impaired Glucose Tolerance or Isolated Impaired Fasting Glucose. Diabetes, 2004;53:1549-1555.

Docherty NG, Le Roux CW. Reconfiguration of the small intestine and diabetes remitting effects of Roux-en-Y gastric bypass surgery. Curr Opin Gastroenterol, 2016;32:61-66.

Ranganath LR, et al. Attenuated GLP-1 secretion in obesity: cause or consequence? Gut, 1996;38:916-919.

Andreani D, et al (editors). Current Views on Hypoglycemia and Glucagon. vol. 30, 1980.

Spiller RC, et al. Further characterisation of the 'ileal brake' reflex in man—effect of ileal infusion of partial digests of fat, protein, and starch on jejunal motility and release of neurotensin, enteroglucagon, and peptide YY. Gut, 1988, 1042-1051.

Vilsboll T, et al. Reduced Postprandial Concentrations of Intact Biologically Active Glucagon-Like Peptide 1 in Type 2 Diabetic Patients. Diabetes, 2001;50:609-613.

Unger RH, Grundy S. Hyperglycaemia as an inducer as well as a consequence of impaired islet cell function and insulin resistance: implications for the management of diabetes. Diabetologia, 1985;28:119-121.

Martin BC, et al. Role of glucose and insulin resistance in development of type 2 diabetes mellitus: results of a 25-year follow-up study. Lancet, 1992;340:925-929.

Rossetti L. Glucose toxicity: the implications of hyperglycemia in the pathophysiology of diabetes mellitus. Clinical and Investigative Medicine, 1995;18(4):255-260.

Guillausseau PJ, et al. Abnormalities in insulin secretion in type 2 diabetes mellitus. Diabetes & Metabolism, 2008;34:S43-S48.

Fabbrini E, et al. Metabolically normal obese people are protected from adverse effects following weight gain. The Journal of Clinical Investigation, 2015;125(2):787-795.

Wildman RP, et al. The Obese Without Cardiometabolic Risk Factor Clustering with the Normal Weight With Cardiometabolic Risk Factor Clustering. Arch Intern Med, 2008;168(15):1617-1624.

* cited by examiner

Weight Loss Over Time

| Date | | Total Weight Loss |
|---|---|---|
| 26-Jan | 10 lbs. | 10 lbs |
| 9-Feb | 2 lbs. | 12 lbs |
| 23-Feb | 2 lbs. | 14 lbs |
| 9-Mar | 3 lbs. | 17 lbs |
| 22-Mar | 2 lbs. | 19 lbs |
| 5-Apr | 1.5 lbs. | 20.5 lbs |
| 14-Apr | 1 lbs. | 21.5 lbs |
| 19-Apr | 0 lbs. | 21.5 lbs |
| 25-Apr | 2.25 lbs. | 23.75 lbs |

FIGURE 3A-B
3A
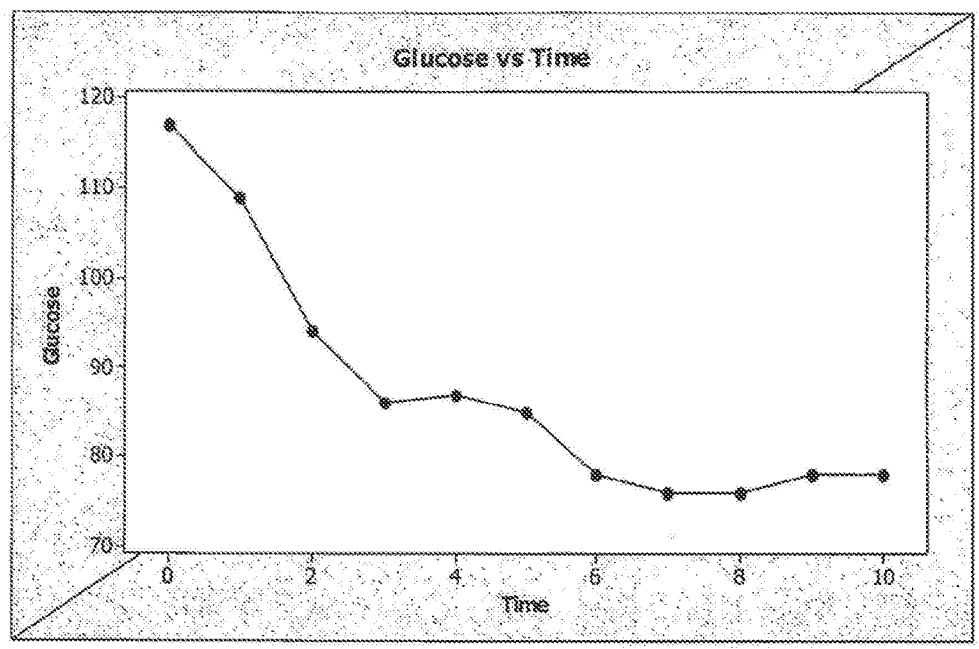
3B
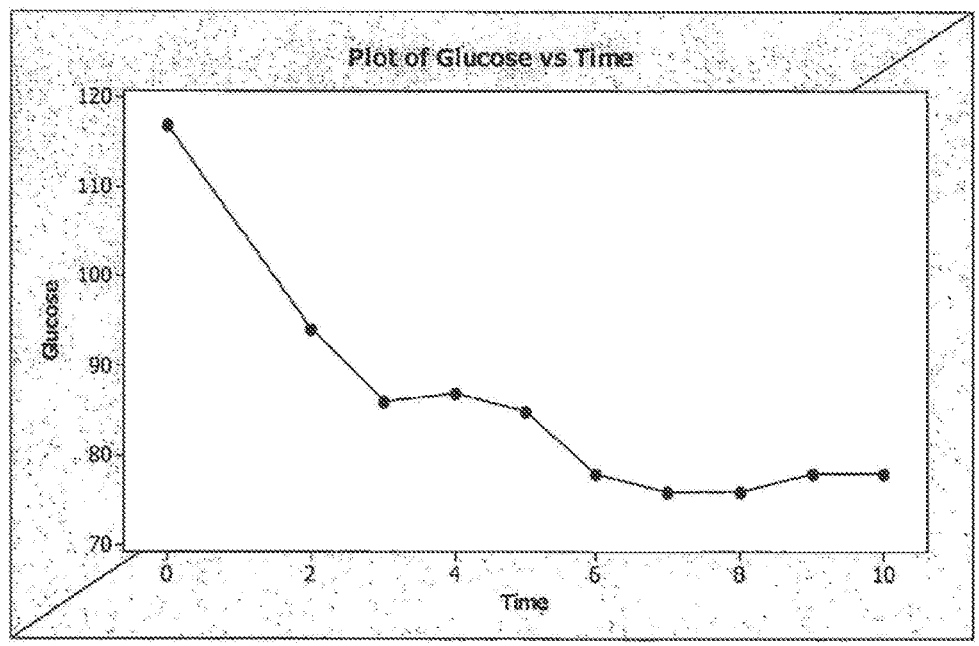

FIGURE 4

TABLE A

Descriptive Statistics of Total Stimulation above the Baseline

| Variable | Total Count | N | N* | Mean | StDev | Minimum | Q1 | Median | Q3 | Maximum |
|---|---|---|---|---|---|---|---|---|---|---|
| GLP1 (all 5 subjects) | 5 | 5 | 0 | 451 | 347 | 151 | 223 | 362 | 722 | 1048 |
| GLP1 (Subject 1 removed) | 5 | 4 | 1 | 301.1 | 108.2 | 151.4 | 187.3 | 328.6 | 387.3 | 395.7 |
| Glucose | 5 | 5 | 0 | 59.1 | 31.7 | 30.5 | 31.5 | 52.5 | 90.0 | 106.5 |
| C-Peptide | 5 | 5 | 0 | 9.02 | 4.95 | 1.90 | 4.70 | 10.45 | 12.63 | 13.60 |
| Insulin | 5 | 5 | 0 | 32.8 | 27.2 | 6.0 | 10.0 | 24.0 | 60.1 | 68.6 |
| PYY | 5 | 5 | 0 | 165.4 | 130.7 | 66.5 | 63.0 | 122.5 | 289.3 | 375.3 |
| Leptin | 5 | 5 | 0 | 66.5 | 52.4 | 8.3 | 19.7 | 61.8 | 115.8 | 142.7 |
| Glucogon | 5 | 5 | 0 | 817 | 505 | 318 | 391 | 817 | 1243 | 1625 |
| IGF-I | 5 | 4 | 1 | 335 | 218 | 208 | 210 | 235 | 559 | 660 |
| IGF-II | 5 | 5 | 0 | 1656 | 471 | 1243 | 1308 | 1426 | 2120 | 2397 |

(N = number of samples used in calculations, N* = number of missing values)

TABLE B

95% Confidence Intervals for Mean of Total Stimulation above the Baseline

| Variable | N | Mean | StDev | SE Mean | 95% CI |
|---|---|---|---|---|---|
| GLP1 (all 5 subjects) | 5 | 450.536 | 347.130 | 155.241 | (119.586, 781.487) |
| GLP1_1 (Subject 1 removed) | 4 | 301.058 | 108.201 | 54.101 | (173.739, 428.377) |
| Glucose | 5 | 59.1000 | 31.7144 | 14.1831 | (29.8638, 89.3362) |
| C-Peptide | 5 | 9.02000 | 4.95365 | 2.03646 | (4.67859, 13.36141) |
| Insulin | 5 | 32.8200 | 27.1838 | 12.1570 | (6.9032, 58.7368) |
| PYY | 5 | 165.444 | 130.684 | 58.444 | (40.851, 290.037) |
| Leptin | 5 | 66.5209 | 52.3629 | 23.4174 | (16.5985, 116.4433) |
| Glucogon | 5 | 816.740 | 505.028 | 225.855 | (335.250, 1298.229) |
| IGF-I | 4 | 334.875 | 217.749 | 108.874 | (78.654, 591.096) |
| IGF-II | 5 | 1656.30 | 471.30 | 210.77 | (1206.97, 2105.63) |

6A

| Time | Patient E | Normal |
|------|-----------|--------|
| 0 | 71.3 | 17 |
| 1 | 69.2 | 45 |
| 2 | 92.4 | 25 |
| 3 | 104.8 | 25 |
| 4 | 69.5 | 21.67 |
| 5 | 137.6 | 21.67 |
| 6 | 122.9 | 21.67 |
| 7 | 113.7 | 21.67 |
| 8 | 127.7 | 21.67 |
| 9 | 113.2 | 21.67 |
| 10 | 64.4 | 21.67 |
| mean | 98.80073 | 23.97182 |

6B

| Time | Patient F | Normal |
|---|---|---|
| 0 | 88.4 | 17 |
| 1 | 64.1 | 45 |
| 2 | 83.4 | 25 |
| 3 | 132.8 | 25 |
| 4 | 89.2 | 21.67 |
| 5 | 90.7 | 21.67 |
| 6 | 103.3 | 21.67 |
| 7 | 114.8 | 21.67 |
| 8 | 133.7 | 21.67 |
| 9 | 125.6 | 21.67 |
| 10 | 109.4 | 21.67 |
| mean | 103.2081 | 23.97182 |

6C

| Time | Patient G | Normal |
|------|-----------|--------|
| 0 | 67.5 | 17 |
| 1 | 85.7 | 45 |
| 2 | 69.3 | 25 |
| 3 | 96.0 | 25 |
| 4 | 129.9 | 21.67 |
| 5 | 168.4 | 21.67 |
| 6 | 98.9 | 21.67 |
| 7 | 90.6 | 21.67 |
| 8 | 116.0 | 21.67 |
| 9 | 109.1 | 21.67 |
| 10 | 78.5 | 21.67 |
| mean | 100.9009 | 23.97182 |

6D

| Time | Patient H | Normal |
|---|---|---|
| 0 | 54.7 | 17 |
| 1 | 88.3 | 45 |
| 2 | 80.5 | 25 |
| 3 | 80.0 | 25 |
| 4 | 121.0 | 21.67 |
| 5 | 80.1 | 21.67 |
| 6 | 61.1 | 21.67 |
| 7 | 72.2 | 21.67 |
| 8 | 56.5 | 21.67 |
| 9 | 45.1 | 21.67 |
| 10 | 67.0 | 21.67 |
| mean | 73.31355 | 23.97182 |

6E

| Time | Patient J | Normal |
|---|---|---|
| 11 | 116.2 | 19.24709 |
| 12 | 119.1 | 18.45964 |
| 13 | 122.0 | 17.67218 |
| 14 | 124.9 | 16.88473 |
| 15 | 127.8 | 16.09727 |
| 16 | 130.7 | 15.30982 |
| 17 | 133.5 | 14.52236 |
| 18 | 136.4 | 13.73491 |
| 19 | 139.3 | 12.94745 |
| 20 | 142.2 | 12.16 |
| 21 | 145.1 | 11.37255 |
| mean | 130.6508 | 15.30982 |

6F

| Time | Patient I Outlier | Normal |
|---|---|---|
| 11 | 129.4 | 19.24709 |
| 12 | 133.7 | 18.45964 |
| 13 | 138.1 | 17.67218 |
| 14 | 142.5 | 16.88473 |
| 15 | 146.8 | 16.09727 |
| 16 | 151.2 | 15.30982 |
| 17 | 155.6 | 14.52236 |
| 18 | 159.9 | 13.73491 |
| 19 | 164.3 | 12.94745 |
| 20 | 168.6 | 12.16 |
| 21 | 173.0 | 11.37255 |
| mean | 151.1929 | 15.30982 |

7A

| Tube # | Subject # Patient F | Bag Number (Collection Time Group) | PYY3-36 (pg/ml) | CV% of PYY |
|---|---|---|---|---|
| 6 | F 01253441 | 0 | 55.051 | 15.82 |
| 27 | F 01253448 | 2 | 49.062 | 7.09 |
| 37 | F 01253454 | 3 | 52.352 | 0.79 |
| 47 | F 01253457 | 4 | 46.307 | 8.35 |
| 57 | F 01253462 | 5 | 40.328 | 14.28 |
| 67 | F 01253464 | 6 | 45.078 | 8.38 |
| 77 | F 01253468 | 7 | 39.996 | 6.56 |
| 87 | F 01253469 | 8 | 39.574 | 12.29 |
| 97 | F 01253471 | 9 | 33.776 | 13.01 |
| 107 | F 01253472 | 10 | 23.446 | 20.18 |
| Tube # | Subject # | Bag Number (Collection Time Group) | PYY3-36 (pg/ml) | CV% of PYY |

7B

| Tube # | Subject # Patient F | Bag Number (Collection Time Group) | PYY3-36 (pg/ml) | CV% of PYY |
|---|---|---|---|---|
| 6 | F 01253441 | 0 | 55.051 | 15.82 |
| 27 | F 01253448 | 2 | 49.062 | 7.09 |
| 37 | F 01253454 | 3 | 52.352 | 0.79 |
| 47 | F 01253457 | 4 | 46.307 | 8.35 |
| 57 | F 01253462 | 5 | 40.328 | 14.28 |
| 67 | F 01253464 | 6 | 45.078 | 8.38 |
| 77 | F 01253468 | 7 | 39.996 | 6.56 |
| 87 | F 01253469 | 8 | 39.574 | 12.29 |
| 97 | F 01253471 | 9 | 33.776 | 13.01 |
| 107 | F 01253472 | 10 | 23.446 | 20.18 |
| Tube # | Subject # | Bag Number (Collection Time Group) | PYY3-36 (pg/ml) | CV% of PYY |

7C

| Tube # | Subject # Patient H | Bag Number (Collection Time Group) | PYY3-36 (pg/ml) | CV% of PYY |
|---|---|---|---|---|
| 8 | H 01253517 | 0 | 19.526 | 0.08 |
| 19 | H 01253519 | 1 | 27.029 | 6.28 |
| 29 | H 01253524 | 2 | 25.417 | 15.65 |
| 39 | H 01253525 | 3 | 28.263 | 5.23 |
| 49 | H 01253526 | 4 | 60.507 | 18.63 |
| 59 | H 01253528 | 5 | 47.955 | 11.06 |
| 69 | H 01253530 | 6 | 28.593 | 8.66 |
| 79 | H 01253531 | 7 | 24.088 | 7.71 |
| 89 | H 01253532 | 8 | 18.302 | 46.37 |
| 99 | H 01253536 | 9 | 20.853 | 11.11 |
| 109 | H 01253538 | 10 | 29.730 | 22.84 |

7D

| Tube # | Subject # Patient I | Bag Number (Collection Time Group) | PYY3-36 (pg/ml) | CV% of PYY |
|---|---|---|---|---|
| 9 | I 01253545 | 0 | 91.100 | 52.80 |
| 20 | I 01253548 | 1 | 97.321 | 10.95 |
| 30 | I 01253550 | 2 | 109.973 | 3.16 |
| 40 | I 01253551 | 3 | 90.102 | 5.75 |
| 50 | I 01253553 | 4 | 65.384 | 3.05 |
| 60 | I 01253554 | 5 | 47.106 | 6.36 |
| 70 | I 01253557 | 6 | 42.368 | 1.46 |
| 80 | I 01253559 | 7 | 35.334 | 0.32 |
| 90 | I 01253562 | 8 | 31.396 | 11.19 |
| 100 | I 01253564 | 9 | 28.382 | 12.89 |
| 110 | I 01253565 | 10 | 22.907 | 3.21 |

7E

| Tube # | Subject # | Bag Number (Collection Time Group) | PYY3-36 (pg/ml) | CV% of PYY |
|---|---|---|---|---|
| 10 | J 01253678 | 0 | 31.108 | 4.10 |
| 21 | J 01253681 | 1 | 21.537 | 0.29 |
| 31 | J 01253683 | 2 | 20.643 | 2.32 |
| 41 | J 01253684 | 3 | 19.759 | 2.49 |
| 51 | J 01253685 | 4 | 17.887 | 2.67 |
| 61 | J 01253686 | 5 | 18.581 | 1.06 |
| 71 | J 01253688 | 6 | 20.607 | 11.62 |
| 81 | J 01253689 | 7 | 16.867 | 15.05 |
| 91 | J 01253694 | 8 | 17.320 | 14.79 |
| 101 | J 01253696 | 9 | 27.709 | 43.85 |
| 111 | J 01253697 | 10 | 13.785 | single-tube |

FIGURE 8
8A
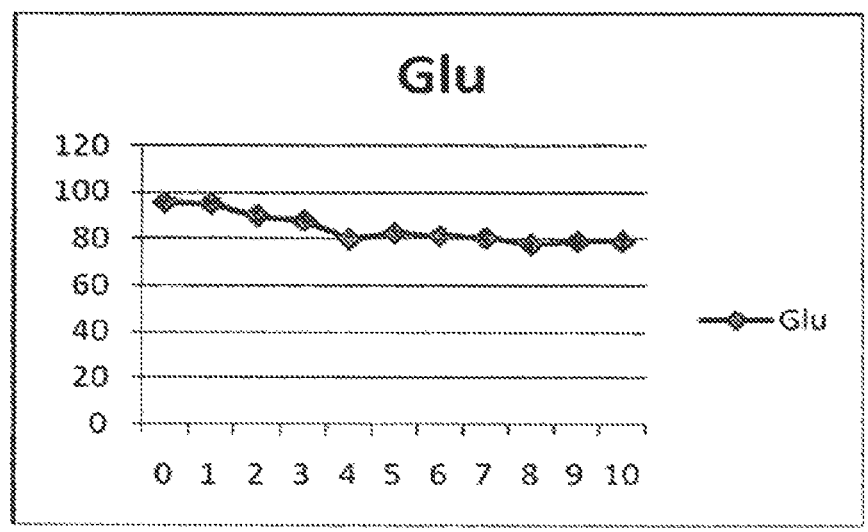
8B
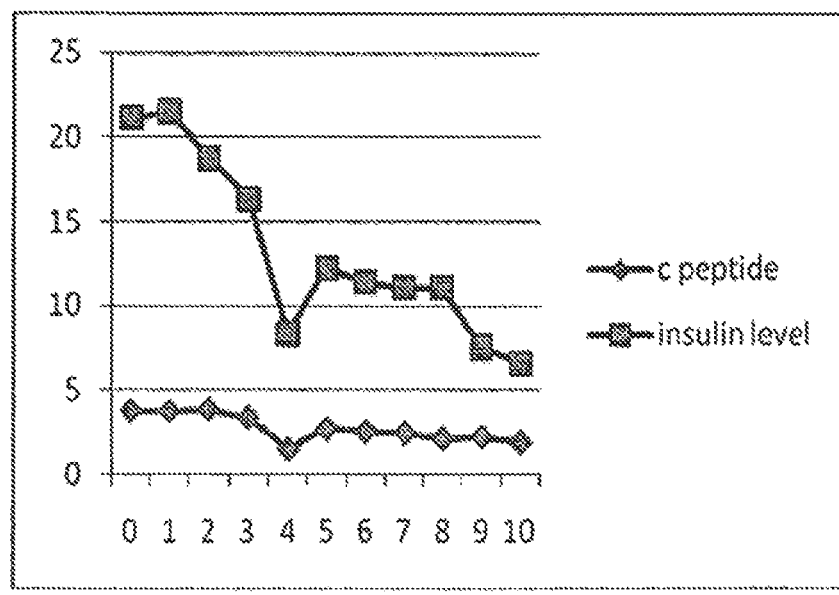

FIGURE 8 (Cont'd)
8C
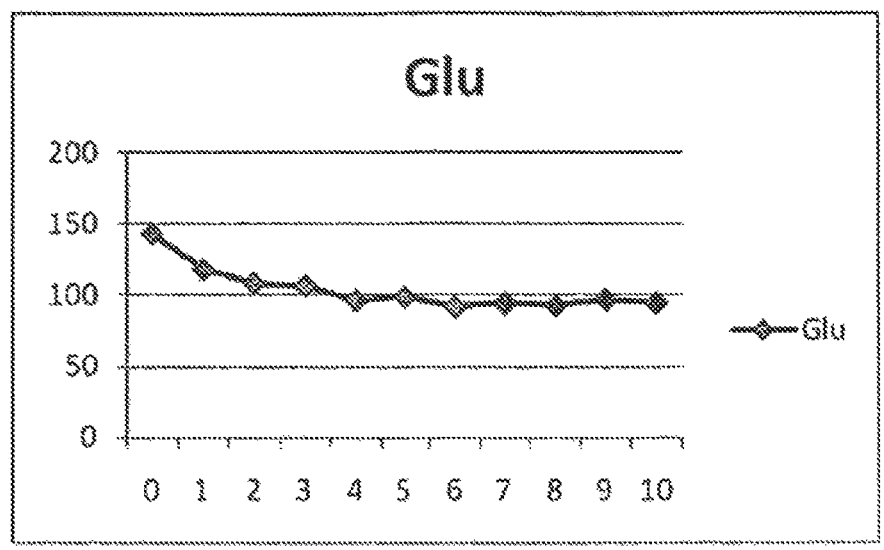
8D
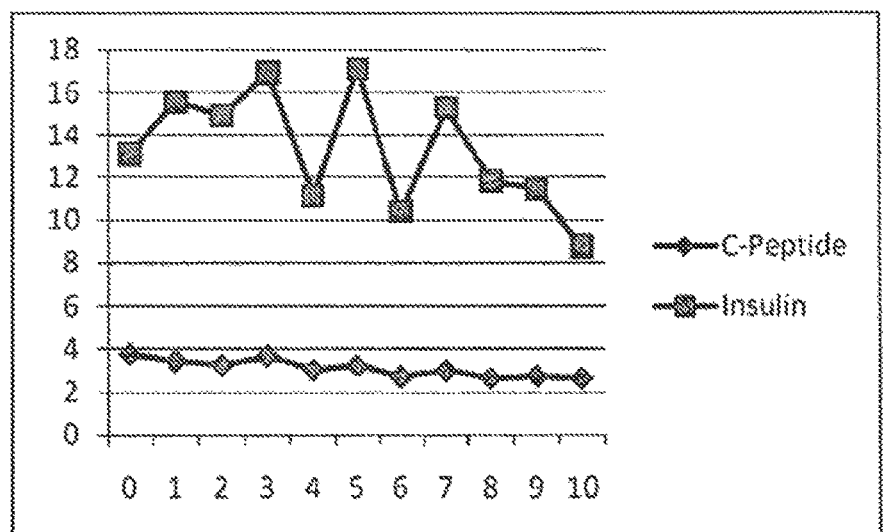

FIGURE 8 (Cont'd)
8E
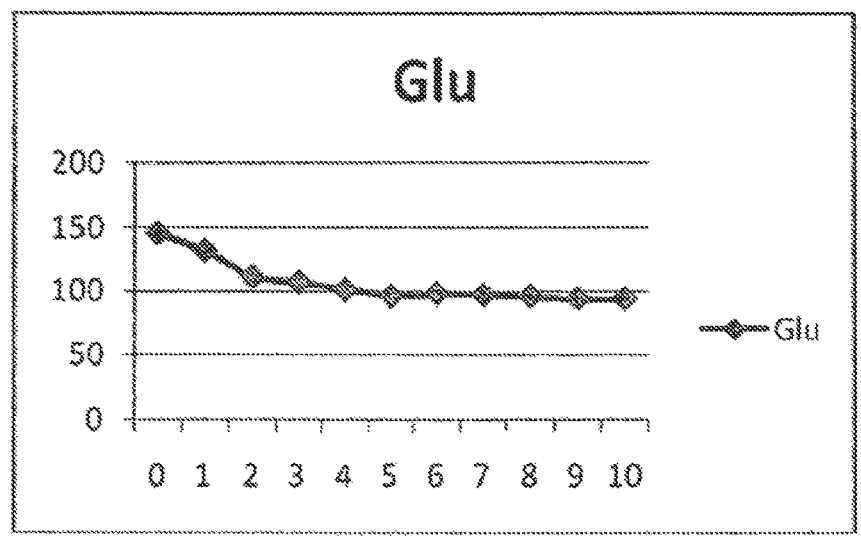
8F
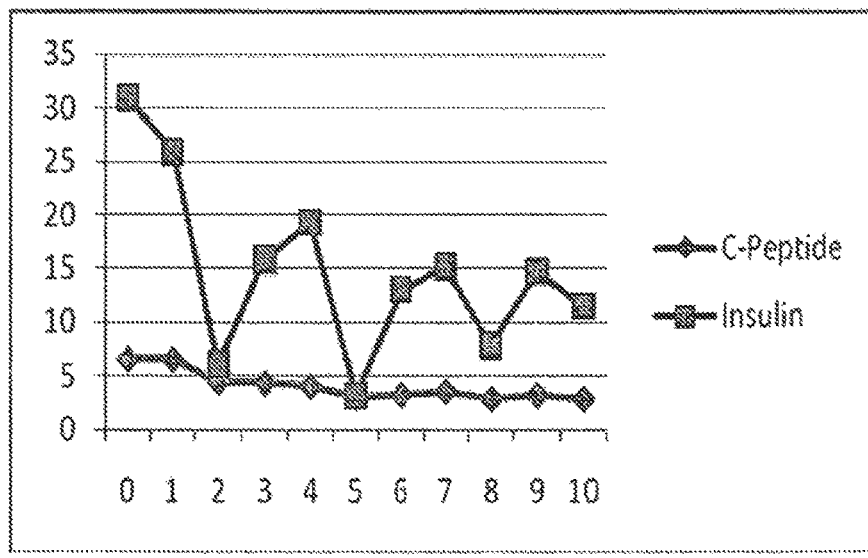

FIGURE 8 (Cont'd)
8G
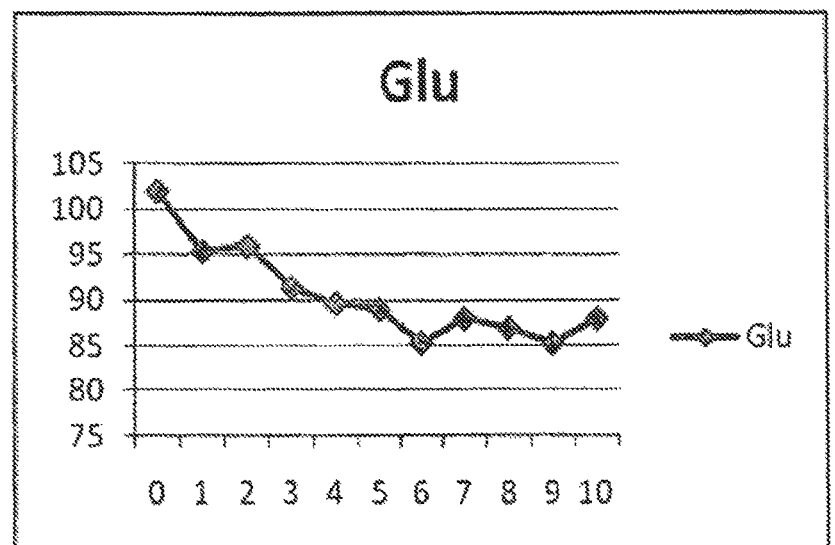
8H
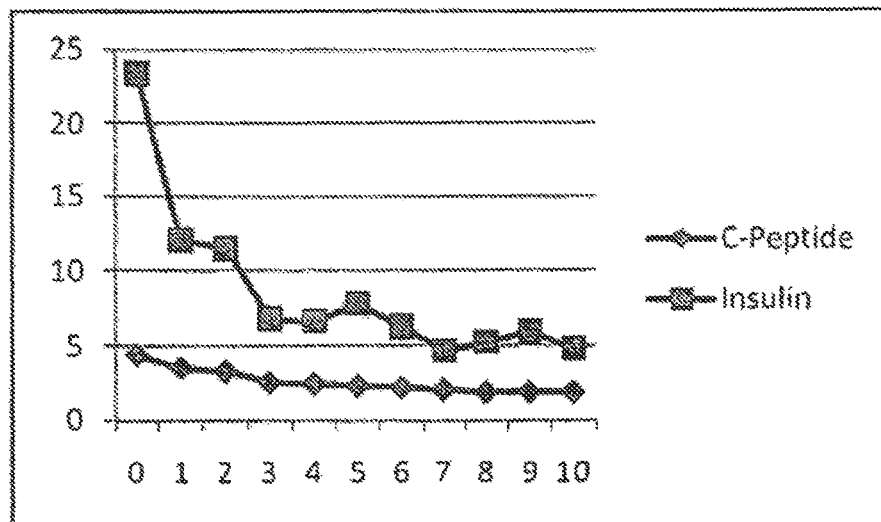

FIGURE 8 (Cont'd)
8I
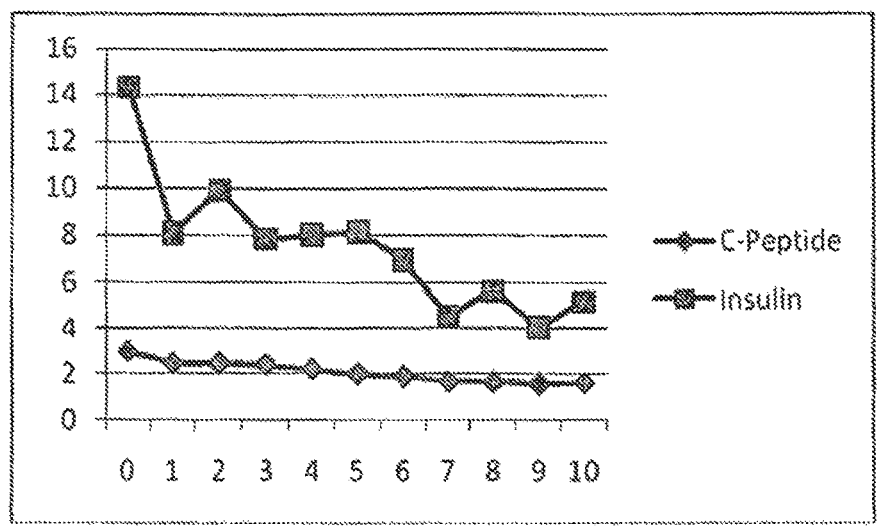
8J
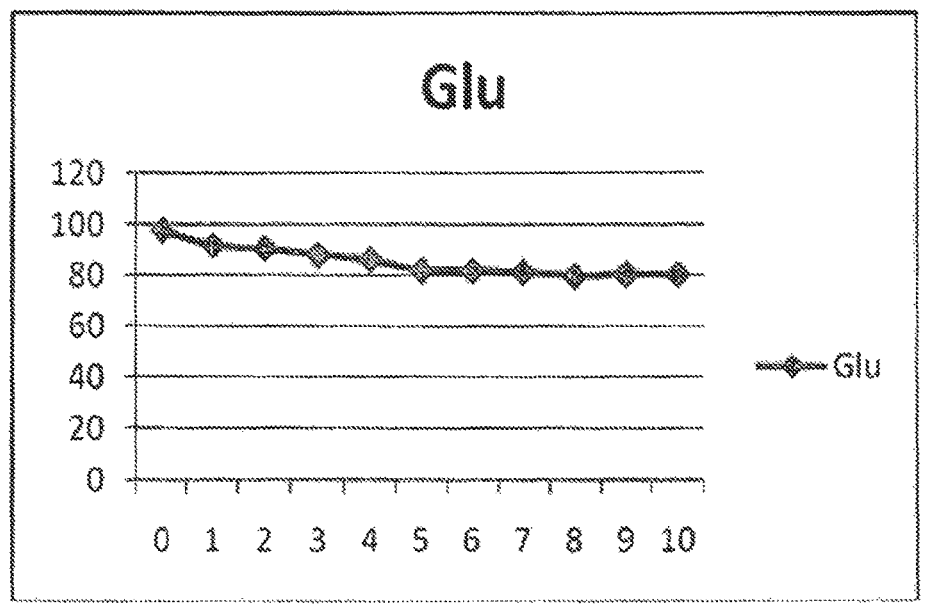

Table 1

| Bag Number (Collection Time Group) | PYY3-36 (pg/ml) | Glucagon (pg/ml) | GLP-1 (pM) | GLP-2 (ng/ml) | Leptin (ng/ml) | Glu | C-Peptide | Insulin |
|---|---|---|---|---|---|---|---|---|
| 0 | 18.4 | 76.75 | 28.1 | 0.98 | 6.45 | 113 | 4.2 | 17.7 |
| 1 | 27.4 | 91.97 | 12.9 | 0.76 | 2.52 | 103 | 3.5 | 14.1 |
| 2 | 18.7 | 75.39 | 32.3 | 0.84 | 0.83 | 103 | 4.2 | 19.7 |
| 3 | 5.0 | 49.86 | 28.2 | 0.89 | 4.95 | 93 | 2.7 | 8.9 |
| 4 | 21.5 | 42.22 | 10.8 | 0.76 | 0.78 | 91 | 2.2 | 7.6 |
| 5 | 26.9 | 65.82 | 59.3 | 0.47 | 0.55 | 91 | 2.1 | 6.9 |
| 6 | 43.1 | 132.99 | 54.4 | 0.69 | 1.07 | 90 | 2.2 | 6.8 |
| 7 | 21.8 | 47.82 | 17.3 | 0.76 | 5.02 | 91 | 2.1 | 7 |
| 8 | 14.3 | 52.95 | 42.4 | 0.72 | 0.63 | 92 | 2 | 6.6 |
| 9 | 16.7 | 58.28 | 24.095 | 0.72 | 2.99 | 87 | 1.7 | 5.3 |
| 10 | 5.0 | 43.06 | 17.2 | 0.61 | 0.84 | 92 | 1.9 | 4.1 |

Table 2

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C-Peptide | Insulin |
|---|---|---|---|---|---|---|---|---|---|
| 1942288 B | 0 | 20.9 | 77.59 | 23.1 | 0.66 | 0.57 | 97 | 1.4 | 4.4 |
| 1942314 B | 1 | 15.2 | 43.01 | 14.1 | 0.69 | 0.39 | 101 | 1.6 | 5.4 |
| 1942320 B | 2 | 5.0 | 48.08 | 10.9 | 0.73 | 0.45 | 96 | 1.5 | 4.2 |
| 1942323 B | 3 | 15.4 | 54.09 | 11.5 | 0.83 | 0.56 | 94 | 1.2 | 2.2 |
| 1942327 B | 4 | 22.8 | 43.04 | 20.2 | 0.59 | 0.40 | 92 | 1 | 1 |
| 1942329 B | 5 | 36.3 | 113.23 | 44.3 | 0.52 | 0.50 | 90 | 0.8 | 1 |
| 1942331 B | 6 | 20.3 | 43.11 | 83.8 | 0.58 | 0.46 | 87 | 0.7 | 1 |
| 1942334 B | 7 | 5.0 | 42.77 | 0.2 | 0.75 | 0.67 | 85 | 0.7 | 1 |
| 1942336 | 8 | 5.0 | | | | | | | |

Table 3

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C-Peptide | Insulin |
|---|---|---|---|---|---|---|---|---|---|
| 1942824 C | 0 | 20.4 | 64.69 | 33.1 | 0.89 | 13.77 | 91 | 1.5 | 3 |
| - | - | | | | | | 74 | 0.9 | 1 |
| 1942828 C | 2 | 21.3 | 85.79 | 45.2 | 0.72 | 11.52 | 87 | 1.3 | 2.8 |
| 1942829 C | 3 | 18.2 | 63.29 | 24.0 | 0.80 | 4.64 | 83 | 1.1 | 1 |
| 1942831 C | 4 | 41.2 | 89.90 | 17.9 | 0.70 | 10.91 | 82 | 0.9 | 1 |
| 1942635 C | 5 | 33.7 | 60.98 | 44.6 | 0.71 | 4.77 | 83 | 1 | 1 |
| 1942636 C | 6 | 18.4 | 55.62 | 53.3 | 0.74 | 6.10 | 78 | 0.9 | 1 |
| 1942639 C | 7 | 15.4 | 41.17 | 0.2 | 1.04 | 7.29 | 76 | 0.9 | 2 |
| 1842641 C | 8 | 5.0 | 41.88 | 22.2 | 0.77 | 3.85 | 77 | 1.1 | 1 |
| 1942647 C | 9 | 21.9 | 98.89 | 33.0 | 0.80 | 3.03 | 77 | 0.8 | 1 |
| 1942649 C | 10 | 16.4 | 70.45 | 77.8 | 0.94 | 3.39 | 77 | 0.8 | 1 |

Table 4

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C-Peptide | Insulin |
|---|---|---|---|---|---|---|---|---|---|
| 1942664 D | 0 | 5.0 | 48.94 | 18.5 | 0.92 | 8.92 | 99 | 2.5 | 5.1 |
| 1942666 D | 1 | 23.5 | 54.75 | 28.2 | 1.27 | 5.47 | 94 | 1.1 | 1 |
| 1942668 D | 2 | 15.9 | 69.95 | 15.4 | 1.03 | 4.21 | 92 | 2.4 | 4.6 |
| 1942672 D | 3 | 40.1 | 192.29 | 33.5 | 1.38 | 6.76 | 93 | 2.1 | 7.3 |
| 1942675 D | 4 | 38.1 | 82.18 | 33.3 | 0.98 | 5.47 | 87 | 1.5 | 4.7 |
| 1942678 D | 5 | 22.0 | 68.66 | 55.7 | 1.07 | 4.37 | 81 | 1.4 | 1 |
| 1942681 D | 6 | 23.1 | 43.26 | 19.3 | 1.12 | 3.95 | 81 | 1.6 | 3.5 |
| 1942682 D | 7 | 5.0 | 42.12 | 35.7 | 1.28 | 5.23 | 81 | 1.3 | 2 |
| 1942683 D | 8 | 19.8 | 70.42 | 61.7 | 1.14 | 3.06 | 82 | 1.3 | 3.1 |
| 1942898 D | 9 | 14.4 | 64.25 | 61.7 | 0.93 | 2.82 | 85 | 1.4 | 3.5 |
| 1942893 D | 10 | 5.0 | 55.34 | 56.7 | 1.09 | 2.48 | 84 | 1.3 | 1 |

Table 5

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C. Peptide | Insulin |
|---|---|---|---|---|---|---|---|---|---|
| 1942704 E | 0 | 19.9 | 86.40 | 8.8 | 0.44 | 5.81 | 99 | 2.3 | 9 |
| 1942707 E | 1 | 14.4 | 43.38 | 3.7 | 0.47 | 3.18 | 94 | 1.9 | 3.7 |
| 1942713 E | 2 | 34.0 | 161.27 | 22.1 | 0.57 | 3.74 | 88 | 1.7 | 1 |
| 1942716 E | 3 | 19.8 | 65.02 | 124.4 | 0.68 | 3.57 | 84 | 2 | 5.8 |
| 1942720 E | 4 | 18.8 | 72.41 | 13.4 | 0.50 | 3.88 | 86 | 1.3 | 2.5 |
| 1942726 E | 5 | 18.7 | 47.89 | 0.2 | 0.51 | 3.90 | 83 | 1.3 | 2 |
| 1942729 E | 6 | 5.0 | 42.46 | 10.5 | 0.68 | 5.84 | 82 | 1.3 | 2.5 |
| 1942738 E | 7 | 15.7 | 53.70 | 28.4 | 0.73 | 4.39 | 81 | 1.2 | 1 |
| 1942736 E | 8 | 5.0 | 50.19 | 0.2 | 0.55 | 3.72 | 81 | 1.1 | 1 |
| 1942737 E | 9 | 5.0 | 44.83 | 41.9 | 0.46 | 3.49 | 80 | 0.9 | 1 |
| 1942738 E | 10 | 12.3 | 87.33 | 42.4 | 0.48 | 3.78 | 82 | 1 | 1 |

Table 6

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C-Peptide | Insulin |
|---|---|---|---|---|---|---|---|---|---|
| 1842803 F | 0 | 22.8 | 52.39 | 16.5 | 0.88 | 24.58 | 89 | 3 | 19.8 |
| 1842805 F | 1 | 38.9 | 82.32 | 0.8 | 0.71 | 12.09 | 88 | 3.5 | 24.5 |
| 1842807 F | 2 | 25.2 | 59.38 | 95.8 | 0.92 | 20.28 | 85 | 3.6 | 20.5 |
| 1842809 F | 3 | 18.9 | 69.14 | 39.2 | 1.07 | 11.57 | 83 | 2.5 | 13.5 |
| 1842811 F | 4 | 24.3 | 44.12 | 9.8 | 0.77 | 18.68 | 79 | 2.3 | 14.7 |
| 1842814 F | 5 | 14.4 | 31.09 | 0.2 | 0.63 | 16.93 | 74 | 1.9 | 10.5 |
| 1842815 F | 6 | 25.3 | 45.29 | 22.3 | 0.95 | 19.07 | 75 | 2 | 11.5 |
| 1842816 F | 7 | 5.0 | 46.74 | 0.2 | 0.73 | 13.32 | 75 | 1.9 | 11.3 |
| 1842819 F | 8 | 5.0 | 34.26 | 68.7 | 0.77 | 15.63 | 73 | 1.7 | 10.1 |
| 1842821 F | 9 | 19.9 | 55.95 | 47.8 | 0.71 | 12.97 | 74 | 2 | 8.1 |
| 1842822 F | 10 | 16.5 | 59.82 | 44.5 | 0.75 | 16.93 | 73 | 1.6 | 8.1 |

Table 7

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C-Peptide | Insulin |
|---|---|---|---|---|---|---|---|---|---|
| 1942838 G | 0 | 37.2 | 80.14 | 19.3 | 0.91 | 27.44 | 136 | 4.1 | 15.9 |
| 1942840 G | 1 | 21.4 | 48.73 | 20.3 | 1.01 | 16.18 | 116 | 3.9 | 16.8 |
| 1942842 G | 2 | 11.6 | 147.82 | 28.6 | 0.78 | 25.33 | 113 | 3.7 | 16.2 |
| 1942846 G | 3 | 14.0 | 57.93 | 31.4 | 0.84 | 22.09 | 110 | 3.7 | 16.5 |
| 1942848 G | 4 | 5.0 | 50.77 | 20.6 | 0.88 | 75.80 | 95 | 3 | 7.4 |
| 1942850 G | 5 | 18.4 | 66.02 | 41.7 | 0.79 | 78.75 | 99 | 3.6 | 19 |
| 1942852 G | 6 | 15.0 | 51.22 | 52.4 | 0.68 | 64.28 | 90 | 3.3 | 13.1 |
| 1942857 G | 7 | 5.0 | 92.26 | 29.5 | 0.79 | 19.93 | 91 | 3.4 | 16.7 |
| 1942860 G | 8 | 12.0 | 74.45 | 30.4 | 0.74 | 55.48 | 88 | 2.9 | 11.9 |
| 1942862 G | 9 | 5.0 | 53.78 | 61.1 | 0.88 | 19.52 | 91 | 3.1 | 11.2 |
| 1942863 G | 10 | 36.2 | 161.36 | 85.7 | 0.79 | 24.47 | 94 | 3.2 | 13.7 |

Table 8

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C Peptide | Insulin |
|---|---|---|---|---|---|---|---|---|---|
| 1942879 H | 0 | 20.4 | 69.53 | 28.3 | 0.66 | 13.90 | 102 | 3.3 | 13 |
| 1942879 H | 1 | 12.1 | 50.11 | 15.5 | 0.57 | 5.85 | 93 | 2.7 | 8.3 |
| 1942880 H | 2 | 14.8 | 83.40 | 23.1 | 0.84 | 9.49 | 96 | 3.3 | 12.8 |
| 1942881 H | 3 | 5.0 | 41.57 | 27.6 | 0.76 | 7.57 | 94 | 2.7 | 7.6 |
| 1942882 H | 4 | 25.4 | 65.72 | 53.9 | 0.71 | 7.87 | 92 | 2.7 | 9.8 |
| 1942885 H | 5 | 19.9 | 59.05 | 66.8 | 0.58 | 4.58 | 82 | 2.2 | 8 |
| 1942888 H | 6 | 5.0 | 38.62 | 58.9 | 0.58 | 9.09 | 81 | 2 | 4.5 |
| 1942891 H | 7 | 16.8 | 71.36 | 0.2 | 0.87 | 5.90 | 81 | 1.9 | 6.1 |
| 1942895 H | 8 | 5.0 | 80.61 | 44.6 | 0.59 | 6.55 | 82 | 1.9 | 5.9 |
| 1942897 H | 9 | 29.8 | 99.30 | 55.7 | 0.66 | 5.24 | 78 | 1.9 | 5.1 |
| 1942899 H | 10 | 16.7 | 80.67 | 100.8 | 0.54 | 5.26 | 85 | 2.1 | 7.5 |

Table 9

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C-Peptide | Insulin |
|---|---|---|---|---|---|---|---|---|---|
| 1842809 | 0 | 24.5 | 115.39 | 29.5 | 1.42 | 7.58 | 81 | 3.1 | 14.4 |
| 1942814 | 1 | 25.1 | 21.28 | 27.8 | 1.29 | 2.55 | 93 | 2.4 | 4.8 |
| 1942816 | 2 | 5.0 | 69.75 | 47.1 | 1.28 | 4.71 | 93 | 2.7 | 8.9 |
| 1942818 | 3 | 29.8 | 91.02 | 108.6 | 1.39 | 2.09 | 87 | 2.4 | 9.6 |
| 1842820 | 4 | 29.6 | 83.38 | 131.2 | 1.48 | 4.26 | 84 | 2.2 | 5.7 |
| 1842822 | 5 | 5.0 | 34.68 | 41.9 | 1.11 | 2.45 | 84 | 2.2 | 9.9 |
| 1842824 | 6 | 23.5 | 52.35 | 32.9 | 1.16 | 5.88 | 86 | 2.1 | 8.4 |
| 1842826 | 7 | 18.4 | 112.60 | 23.2 | 1.27 | 4.80 | 83 | 1.5 | 3.7 |
| 1842828 | 8 | 32.8 | 207.41 | 27.2 | 1.23 | 3.50 | 87 | 1.6 | 6.6 |
| 1842830 | 9 | 18.5 | 67.67 | 67.2 | 1.13 | 3.01 | 88 | 1.5 | 2 |
| 1842832 | 10 | 5.0 | 86.62 | 41.4 | 1.23 | 3.14 | 81 | 1.8 | 4.6 |

Table 11

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C. Peptide | Insulin |
|---|---|---|---|---|---|---|---|---|---|
| 1843018 K | 0 | 13.6 | 44.91 | 10.4 | 0.65 | 78.59 | 90 | 2.8 | 26.6 |
| 1843018 K | 1 | 23.3 | 45.05 | 0.2 | 0.64 | 30.73 | 85 | 1.5 | 3.9 |
| 1843026 K | 2 | 11.7 | 66.07 | 29.3 | 0.64 | 66.13 | 89 | 1.1 | 4.2 |
| 1843031 K | 3 | 15.1 | 37.40 | 29.5 | 0.72 | 32.29 | 87 | 1.3 | 5.1 |
| 1843032 K | 4 | 34.0 | 68.19 | 75.8 | 0.91 | 67.76 | 87 | 1.7 | 7.5 |
| 1843035 K | 5 | 25.3 | 76.34 | 38.4 | 0.98 | 22.50 | 87 | 1.6 | 8.9 |
| 1843038 K | 6 | 44.3 | 103.67 | 54.3 | 1.06 | 67.77 | 77 | 1.2 | 4.6 |
| 1843041 K | 7 | 22.2 | 71.06 | 19.3 | 0.90 | 33.89 | 83 | 1 | 2.6 |
| 1843043 K | 8 | 6.0 | 71.17 | 16.3 | 0.77 | 15.90 | 83 | 1.1 | 4.1 |
| 1843052 K | 9 | 5.0 | 47.47 | 3.5 | 0.53 | 18.50 | 81 | 1.2 | 6.1 |
| 1843053 K | 10 | 5.0 | 49.96 | 0.2 | 0.64 | 17.62 | 83 | 1.1 | 3.8 |

Table 12

Table 13

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C-Peptide | Insulin |
|---|---|---|---|---|---|---|---|---|---|
| 1843196 M | 0 | 20.0 | 84.86 | 23.2 | 0.86 | 29.16 | 95 | 2.1 | 6.4 |
| 1843187 M | 1 | 5.0 | 31.48 | 17.9 | 0.62 | 20.11 | 99 | 2 | 5.2 |
| 1843188 M | 2 | 22.4 | 114.53 | 66.4 | 1.12 | 23.48 | 92 | 1.9 | 4.9 |
| 1843189 M | 3 | 26.4 | 81.14 | 20.2 | 0.89 | 16.04 | 94 | 1.7 | 1 |
| 1843190 M | 4 | 40.2 | 173.91 | 69.0 | 0.58 | 27.82 | 96 | 1.4 | 2.7 |
| 1843191 M | 5 | 20.5 | 52.80 | 9.3 | 0.70 | 20.14 | 87 | 1.2 | 1 |
| 1843193 M | 6 | 15.5 | 58.01 | 44.4 | 0.78 | 23.82 | 88 | 1.5 | 3.6 |
| 1843194 M | 7 | 12.0 | 44.07 | 0.2 | 0.82 | 18.67 | 90 | 1.1 | 1 |
| 1843195 M | 8 | 5.0 | 50.51 | 15.9 | 0.71 | 18.99 | 85 | 1.1 | 1 |
| 1843196 M | 9 | 21.4 | 60.70 | 39.5 | 0.55 | 13.86 | 83 | 1 | 1 |
| 1843197 M | 10 | 5.0 | 68.10 | 39.3 | 0.71 | 17.84 | 85 | 1 | 1 |

Table 14

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C-Peptide | Insulin |
|---|---|---|---|---|---|---|---|---|---|
| 1843207 N | 0 | 16.0 | 52.93 | 17.7 | 1.02 | 5.81 | 109 | 3.6 | 4.2 |
| 1843209 N | 1 | 26.2 | 34.19 | 17.6 | 0.81 | 2.10 | 108 | 3.5 | 3.6 |
| 1843212 N | 2 | 21.1 | 71.86 | 110.8 | 0.64 | 1.79 | 103 | 3.6 | 4 |
| 1843213 N | 3 | 45.9 | 115.70 | 24.3 | 0.74 | 4.17 | 101 | 3.4 | 4.6 |
| 1843214 N | 4 | 35.1 | 83.55 | 22.8 | 0.49 | 3.40 | 98 | 3.1 | 4.8 |
| 1843215 N | 5 | 21.6 | 58.61 | 18.4 | 0.79 | 2.11 | 98 | 3.3 | 3.6 |
| 1843217 N | 6 | 27.1 | 46.95 | 21.6 | 0.88 | 3.73 | 95 | 3.7 | 4.8 |
| 1843218 N | 7 | 5.0 | 43.01 | 25.9 | 0.80 | 2.00 | 90 | 2.7 | 1 |
| 1843220 N | 8 | 28.0 | 69.09 | 18.4 | 0.96 | 3.77 | 91 | 2.7 | 3.2 |
| 1843222 N | 9 | 22.4 | 81.14 | 15.5 | 0.75 | 1.87 | 90 | 2.5 | 3.7 |
| 1843223 N | 10 | 5.0 | 53.19 | 13.3 | 0.89 | 2.53 | 88 | 2.4 | 1 |

Table 15

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C-Peptide | Insulin |
|---|---|---|---|---|---|---|---|---|---|
| 1943231 0 | 0 | 25.7 | 48.73 | 8.0 | 1.06 | 2.54 | 87 | 0.7 | 1 |
| 1943236 0 | 1 | 22.9 | 30.57 | 8.8 | 0.78 | 1.12 | 82 | 0.9 | 1 |
| 1943237 0 | 2 | 36.5 | 116.12 | 95.9 | 0.80 | 1.34 | 85 | 0.8 | 1 |
| 1943238 0 | 3 | 31.0 | 51.34 | 31.6 | 0.79 | 1.52 | 82 | 0.7 | 1 |
| 1943241 0 | 4 | 26.1 | 67.84 | 16.3 | 0.72 | 4.47 | 94 | 3.7 | 14.8 |
| 1943243 0 | 5 | 17.6 | 36.50 | 19.4 | 0.78 | 0.63 | 81 | 0.8 | 1 |
| 1943247 0 | 6 | 8.1 | 36.72 | 16.9 | 0.70 | 1.41 | 85 | 0.8 | 1 |
| 1943248 0 | 7 | 17.3 | 48.98 | 25.9 | 0.67 | 78.92 | 81 | 0.5 | 1 |
| 1943249 0 | 8 | 5.0 | 43.29 | 58.0 | 0.72 | 0.65 | 83 | 0.6 | 1 |
| 1943250 0 | 9 | 5.0 | 48.65 | 25.3 | 0.64 | 0.78 | 80 | 0.6 | 1 |
| 1943254 0 | 10 | 19.0 | 78.27 | 14.2 | 0.64 | 11.96 | 80 | 0.5 | 1 |

Table 16

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C-Peptide | Insulin |
|---|---|---|---|---|---|---|---|---|---|
| 1943287 P | 0 | 19.2 | 81.10 | 23.4 | 1.19 | 24.51 | 145 | 6.6 | 30.9 |
| 1943288 P | 1 | 39.5 | 468.87 | 36.0 | 0.94 | 14.97 | 132 | 6.6 | 25.3 |
| 1943289 P | 2 | 22.2 | 77.30 | 84.8 | 1.17 | 18.14 | 111 | 4.5 | 6.1 |
| 1943302 P | 3 | 29.5 | 67.18 | 33.9 | 1.00 | 76.83 | 107 | 4.4 | 15.8 |
| 1943304 P | 4 | 21.0 | 68.65 | 11.2 | 0.78 | 43.91 | 101 | 4.1 | 19.3 |
| 1943305 P | 5 | 12.6 | 44.44 | 12.7 | 0.93 | 24.44 | 96 | 3.1 | 3.2 |
| 1943307 P | 6 | 26.2 | 64.14 | 40.9 | 1.23 | 62.50 | 98 | 3.3 | 13 |
| 1943309 P | 7 | 5.0 | 49.63 | 20.2 | 0.98 | 18.07 | 97 | 3.6 | 15.2 |
| 1943313 P | 8 | 5.0 | 42.21 | 57.5 | 0.86 | 18.44 | 96 | 2.9 | 7.8 |
| 1943314 P | 9 | 22.8 | 73.17 | 52.1 | 1.00 | 21.34 | 94 | 3.3 | 18.7 |
| 1943315 P | 10 | 5.0 | 125.88 | 78.0 | 0.87 | 17.97 | 94 | 2.9 | 11.5 |

Table 17

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C Peptide | Insulin |
|---|---|---|---|---|---|---|---|---|---|
| 1843324 Q | 0 | 37.3 | 165.78 | 0.5 | 0.99 | 92.07 | 103 | 2.4 | 8.8 |
| 1843325 Q | 1 | 21.1 | 72.88 | 23.9 | 0.70 | 21.88 | 84 | 2 | 11.1 |
| 1843328 Q | 2 | 12.4 | 66.58 | 57.4 | 0.98 | 68.03 | 90 | 1.8 | 3.3 |
| 1843346 Q | 3 | 23.0 | 46.40 | 14.9 | 0.91 | 15.87 | 87 | 2.1 | 8.5 |
| 1843329 Q | 4 | 27.1 | 40.55 | 6.6 | 0.87 | 68.62 | 83 | 1.6 | 1 |
| 1843331 Q | 5 | 27.1 | 43.64 | 28.0 | 0.81 | 33.52 | 90 | 1.7 | 8.6 |
| 1843342 Q | 6 | 20.6 | 151.41 | 14.1 | 1.07 | 28.52 | 84 | 1.8 | 10 |
| 1843345 Q | 7 | 5.0 | 34.53 | 5.1 | 0.89 | 150 | 82 | 1.6 | 7.2 |
| 1843347 Q | 8 | 15.8 | 57.76 | 50.8 | 0.79 | 83.42 | 81 | 1.3 | 2.8 |
| 1843348 Q | 9 | 5.0 | 33.53 | 103.2 | 0.91 | 20.53 | 82 | 1.7 | 4.6 |
| 1843351 Q | 10 | 34.0 | 180.29 | 42.7 | 0.85 | 6.49 | 90 | 1.9 | 9.2 |

Table 18

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C-Peptide | Insulin |
|---|---|---|---|---|---|---|---|---|---|
| 1943396R | 0 | 20.5 | 55.74 | 23.2 | 0.95 | 92.42 | 88 | 1.9 | 9.8 |
| 1943397R | 1 | 5.0 | 58.77 | 19.4 | 0.86 | 22.07 | 82 | 2.9 | 11.6 |
| 1943401R | 2 | 16.7 | 48.75 | 25.7 | 0.79 | 40.66 | 83 | 1.5 | 1 |
| 1943402R | 3 | 18.2 | 43.78 | 13.7 | 0.72 | 12.90 | 75 | 1.4 | 2.4 |
| 1943404R | 4 | 24.5 | 70.29 | 8.5 | 0.89 | 20.08 | 80 | 1.5 | 3.9 |
| 1943406R | 5 | 24.5 | 51.43 | 27.4 | 0.77 | 22.59 | 73 | 1.2 | 2.4 |
| 1943407R | 6 | 5.0 | 40.90 | 23.4 | 0.96 | 20.43 | 79 | 1.1 | 3.8 |
| 1943408R | 7 | 13.0 | 68.14 | 0.2 | 0.73 | 30.40 | 77 | 1.2 | 6.3 |
| 1943410R | 8 | 5.0 | 55.27 | 42.6 | 0.58 | 1.01 | 75 | 1 | 1 |
| 1943411R | 9 | 30.4 | 131.08 | 70.0 | 0.83 | 12.17 | 85 | 1.2 | 6.1 |
| 1943415R | 10 | 17.0 | 104.64 | 16.8 | 0.64 | 18.25 | 80 | 1 | 3.8 |

Table 19

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C Peptide | Insulin |
|---|---|---|---|---|---|---|---|---|---|
| 1943425 S | 0 | 13.9 | 54.77 | 11.8 | 0.76 | 1.25 | 94 | 0.9 | 1 |
| 1943427 S | 1 | 14.6 | 69.83 | 17.1 | 0.71 | 1.84 | 97 | 1.8 | 3.5 |
| 1943430 S | 2 | 5.0 | 58.90 | 23.9 | 0.75 | 1.43 | 86 | 1.3 | 1 |
| 1943431 S | 3 | 32.5 | 59.04 | 10.8 | 0.68 | 1.33 | 88 | 1.2 | 2.6 |
| 1943433 S | 4 | 19.0 | 98.84 | 86.0 | 0.63 | 1.37 | 85 | 1.1 | 1 |
| 1943436 S | 5 | 16.6 | 39.45 | 30.8 | 0.74 | 0.73 | 86 | 1 | 1 |
| 1943438 S | 6 | 22.8 | 50.00 | 30.9 | 0.62 | 1.10 | 84 | 0.9 | 1 |
| 1943440 S | 7 | 5.0 | 103.91 | 13.2 | 0.64 | 1.78 | 82 | 1 | 1 |
| 1943443 S | 8 | 32.1 | 135.36 | 59.5 | 0.84 | 12.56 | 84 | 0.9 | 1 |
| 1943444 S | 9 | 17.9 | 43.55 | 80.6 | 0.51 | 1.67 | 79 | 0.7 | 1 |
| 1943445 S | 10 | 14.3 | 76.07 | 61.4 | 0.71 | 0.78 | 83 | 0.8 | 1 |

Table 20

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C-Peptide | Insulin |
|---|---|---|---|---|---|---|---|---|---|
| 1943455 | 0 | 17.5 | 38.80 | 0.2 | 0.89 | 2.16 | 87 | 1.5 | 4.2 |
| 1943456 | 1 | 5.0 | 48.02 | 0.2 | 0.74 | 3.24 | 90 | 2 | 4.9 |
| 1943466 | 2 | 23.3 | 81.99 | 3.2 | 0.76 | 3.06 | 94 | 1.1 | 1 |
| 1943467 | 3 | 23.5 | 47.26 | 9.4 | 0.73 | 1.63 | 89 | 1 | 1 |
| 1943473 | 4 | 14.8 | 42.20 | 38.4 | 0.74 | 1.81 | 85 | 0.8 | 1 |
| 1943476 | 5 | 22.8 | 58.46 | 25.8 | 0.90 | 2.40 | 88 | 1 | 1 |
| 1943478 | 6 | 5.0 | 55.67 | 43.6 | 0.72 | 1.55 | 87 | 0.8 | 1 |
| 1943480 | 7 | 34.5 | 182.48 | 8.0 | 0.88 | 1.60 | 89 | 0.7 | 1 |
| 1943483 | 8 | 23.0 | 64.82 | 60.3 | 0.70 | 1.64 | 88 | 0.6 | 1 |
| 1943484 | 9 | 5.0 | 63.79 | 15.9 | 0.62 | 1.27 | 85 | 0.6 | 1 |
| 1943485 | 10 | 13.2 | 55.66 | 0.2 | 0.75 | 1.01 | 85 | 0.6 | 1 |

Table 21

| Subject # | Bag Number (Collection Time Group) | PYY3-36 (pg/ml) | Glucagon (pg/ml) | GLP-1 (pM) | GLP-2 (ng/ml) | Leptin (ng/ml) | Glu | C-Peptide | Insulin |
|---|---|---|---|---|---|---|---|---|---|
| 1943489 U | 0 | 5.0 | 60.91 | 2.8 | 0.94 | 52.09 | 113 | 4.2 | 17.7 |
| 1943500 U | 1 | 20.4 | 67.74 | 22.5 | 0.80 | 7.14 | 103 | 3.5 | 14.1 |
| 1943505 U | 2 | 10.2 | 60.78 | 30.3 | 0.93 | 18.85 | 103 | 4.2 | 19.7 |
| 1943516 U | 3 | 16.6 | 42.86 | 31.3 | 0.66 | 28.21 | 93 | 2.7 | 8.9 |
| 1943517 U | 4 | 27.3 | 72.77 | 60.6 | 0.70 | 54.27 | 91 | 2.2 | 7.6 |
| 1943520 U | 5 | 16.6 | 52.17 | 56.8 | 0.98 | 17.59 | 91 | 2.1 | 6.9 |
| 1943523 U | 6 | 32.6 | 69.46 | 35.0 | 1.02 | 29.61 | 90 | 2.2 | 6.8 |
| 1943527 U | 7 | 14.1 | 95.22 | 41.1 | 0.79 | 67.59 | 91 | 2.1 | 7 |
| 1943530 U | 8 | 5.0 | 58.12 | 14.7 | 0.78 | 20.81 | 92 | 2 | 6.6 |
| 1943532 U | 9 | 13.3 | 44.07 | 25.4 | 0.85 | 17.75 | 87 | 1.7 | 5.3 |
| 1943535 U | 10 | 5.0 | 51.79 | 12.1 | 0.99 | 22.86 | 92 | 1.9 | 4.1 |

FIGURE 39
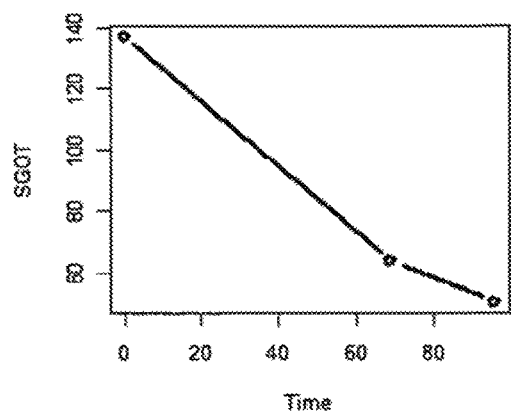
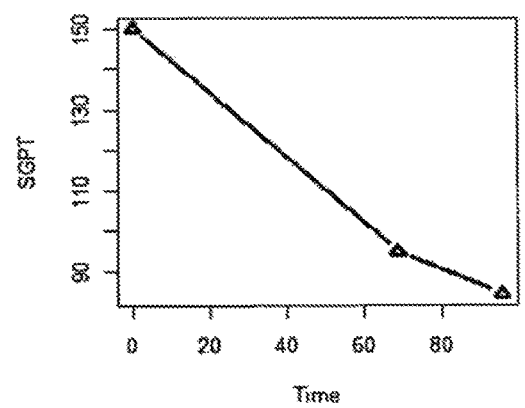
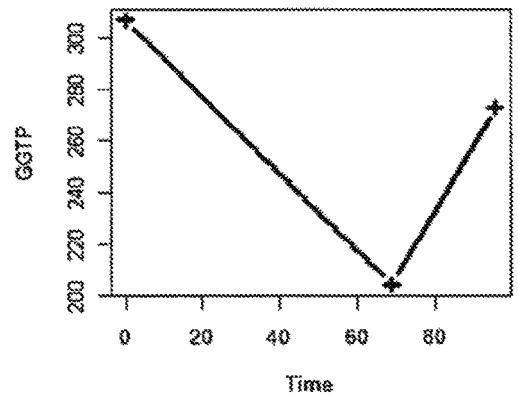
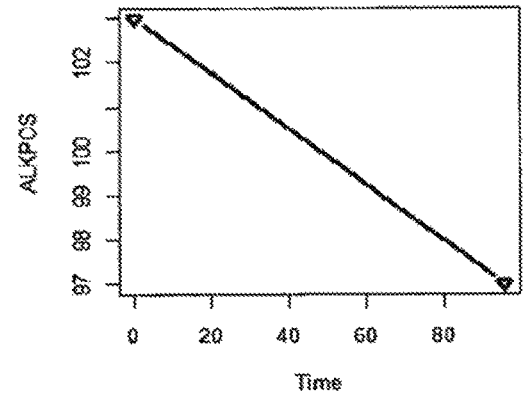

COMPOSITIONS AND METHODS FOR TREATING INSULIN RESISTANCE AND NON-INSULIN DEPENDENT DIABETES MELLITUS (TYPE II DIABETES)

RELATED APPLICATIONS

The present application is a continuation-in-part application of international application PCT/US09/005,016, filed Sep. 2, 2009, entitled "Compositions and Methods for Inducing Satiety and Treating Non-Insulin Dependent Diabetes Mellitus, Pre-diabetic symptoms, Insulin Resistance and Related Disease States and Conditions" which claims priority from U.S. provisional application U.S. 61/190,818, filed Sep. 3, 2008, entitled "Compositions and Methods for Inducing Satiety". The present application also claims priority from U.S. provisional application Ser. No. 61/309,991, filed Mar. 3, 2010, entitled "Compositions and Methods for Inducing Satiety and Treating Non-Insulin Dependent Diabetes Mellitus, Pre-diabetic symptoms, Insulin Resistance and Related Disease States and Conditions", the entire contents of each of the above applications being incorporated by reference in their entirety herein.

FIELD OF THE INVENTION

The present invention relates to compositions and methods for inducing satiety. The present invention also relates to nutritional supplements to the human diet, and more specifically to nutritional supplements which contain a combination of naturally occurring substances which are particularly adapted to treating noninsulin dependent diabetes mellitus, pre-diabetic symptoms, insulin resistance and related disease states and conditions of the gastrointestinal tract diagnostic applications and transport of other medicaments. The present invention also relates to methods of using and treating disease states, disorders and/or conditions.

BACKGROUND OF THE INVENTION

One of the factors thought to contribute to satiety is glucagon-like peptide-1 (7-36) amide (GLP-1), which is processed from proglucagon throughout the small bowel and in the distal small bowel (ileum), and to a lesser extent in the ascending colon, as well as in the central nervous system. GLP-1 has powerful actions on the gastrointestinal tract. Infused in physiological amounts, GLP-1 potently inhibits pentagastrin-induced as well as meal-induced gastric acid secretion. It also inhibits gastric emptying rate and pancreatic enzyme secretion. Similar inhibitory effects on gastric and pancreatic secretion and motility may be elicited in humans upon perfusion of the ileum with carbohydrate- or lipid-containing solutions. Concomitantly, GLP-1 secretion is greatly stimulated, and it has been speculated that GLP-1 may be at least partly responsible for this so-called "ileal-brake" effect.

Within the central nervous system, GLP-1 has a satiating effect, since administration of GLP-1 into the third cerebral ventricle reduces short-term food intake (and meal size), while administration of GLP-1 antagonists have the opposite effect. The administration of graded doses of human GLP-1 produced plasma glucagon-like peptide-1 concentrations within physiological ranges and resulted in the reduction of intake of food in non-obese, healthy male subjects.

GLP-1 is formed and secreted in parallel in the intestinal mucosa along with glicentin (corresponding to PG (1 69), with the glucagon sequence occupying residues Nos. 33 61); small amounts of C-terminally glycine-extended but equally bioactive GLP-1 (7 37), (PG (78 108)); intervening peptide-2 (PG (111 122)amide); and GLP-2 (PG (126 158)). A fraction of glicentin is cleaved further into GRPP (PG (1 30)) and oxyntomodulin (PG (33 69)).

GLP-1 is also effective in stimulating insulin secretion in NIDDM patients. Additionally, it potently inhibits glucagon secretion. Because of these actions it has pronounced blood glucose lowering effects, particularly in patients with NIDDM. Byetta® (exenatide) is an incretin mimetic and a GLP-1 receptor agonist. Byetta® mimics the actions of GLP-1 that occur naturally in the gastrointestinal tract and has emerged as an efficacious type 2 (non-insulin-dependent) diabetes therapy adjunct to one or more oral hypoglycemic agents.

Peptide YY (PYY), a 36-amino-acid peptide, is secreted primarily from L-cells residing in the intestinal mucosa of the ileum and large intestine. PYY, which belongs to a family of peptides including neuropeptide Y (NPY) and pancreatic polypeptide, is released into the circulation as PYY(PYY (1-36) and PYY(PYY (3-36); the latter is the major form of PYY in gut mucosal endocrine cells and throughout the circulation. Plasma PYY levels begin to rise within fifteen minutes after the ingestion of food, plateau within approximately ninety minutes, and remain elevated for up to six hours. Exogenous administration of PYY(PYY (3-36) reduces energy intake and body weight in both humans and animals. Via Y2 receptors, the satiety signal mediated by PYY inhibits NPY neurons and activates pro-opiomelanocortin neurons within the hypothalamic arcuate nucleus. Peripheral PYY(PYY (3-36) binds Y2 receptors on vagal afferent terminals to transmit the satiety signal to the brain.

Insulin is the principal hormone responsible for the control of glucose metabolism. It is synthesized in the β cells of the islets of Langerhans as the precursor, proinsulin, which is processed to form C-peptide and insulin, and both are secreted in equimolar amounts into the portal circulation.

U.S. Pat. Nos. 5,753,253 and 6,267,988 disclosed that since satiety feedback from the ileum is more intense per amount of sensed nutrient than from proximal bowel (jejunum), timing the release of a satiety-inducing agent to predominate in ileum will also enhance the satiety response per amount of agent ingested. Thus, both the spread and predominant site of delivery (ileum) will maximize the effect, so that a small amount of released nutrient will be sensed as though it were a large amount, creating a high satiating effect. U.S. Pat. Nos. 5,753,253 and 6,267,988 disclose administration of a satiety-inducing agent with a meal and at a time of around 4-6 hours before the next scheduled meal.

U.S. Pat. No. 7,081,239 discloses manipulating the rate of upper gastrointestinal transit of a substance in a mammal, as well as methods of manipulating satiety and post-prandialpyramidal visceral blood flow. The methods of treatment disclosed in U.S. Pat. No. 7,081,239 can be administered up to a period of 24 hours prior to ingestion of the food, nutrient and/or drug, but most preferably are administered between about 60 to 5 minutes before ingestion. U.S. Pat. No. 7,081,239 notes that in prolonged treatment of postprandial diarrhea or intestinal dumping, there is at least a potential for an adaptive sensory feedback response that can allow treatment to be discontinued for a number of days without a recurrence of the disorders.

Despite the aforementioned knowledge regarding the role of ileal hormones in digestion and insulin secretion, the need continues to exist for improved therapies that harness the "ileal-brake" effect and GLP-1-insulin pathway to treat or prevent the onset of obesity and obesity-related disorders. The growing prevalence of obesity and obesity-related disorders makes this need particularly acute.

Type II, or noninsulin-dependent diabetes mellitus (NIDDM) typically develops in adulthood. NIDDM is associated with resistance of glucose-utilizing tissues like adipose tissue, muscle, and liver, to the actions of insulin. Initially, the pancreatic islet beta cells compensate by secreting excess insulin. Eventual islet failure results in decompensation and chronic hyperglycemia. Conversely, moderate islet insufficiency can precede or coincide with peripheral insulin resistance.

There are several classes of drugs that are useful for treatment of NIDDM: 1) insulin releasers, which directly stimulate insulin release, carrying the risk of hypoglycemia; 2) prandial insulin releasers, which potentiate glucose-induced insulin secretion, and must be taken before each meal; 3) biguanides, including metformin, which attenuate hepatic gluconeogenesis (which is paradoxically elevated in diabetes); 4) insulin sensitizers, for example the thiazolidinedione derivatives rosiglitazone and pioglitazone, which improve peripheral responsiveness to insulin, but which have side effects like weight gain, edema, and occasional liver toxicity; 5) insulin injections, which are often necessary in the later stages of NIDDM when the islets have failed under chronic hyperstimulation.

Insulin resistance can also occur without marked hyperglycemia, and is generally associated with atherosclerosis, obesity, hyperlipidemia, and essential hypertension. This cluster of abnormalities constitutes the "metabolic syndrome" or "insulin resistance syndrome". Insulin resistance is also associated with fatty liver, which can progress to chronic inflammation, nonalcoholic steatohepatitis, fibrosis, and cirrhosis. Cumulatively, insulin resistance syndromes, including but not limited to diabetes, underlie many of the major causes of morbidity and death of people over age 40.

Despite the existence of various drugs, diabetes remains a major and growing public health problem. What is needed is not necessarily new drug therapies, which often are accompanied by significant side effects, but rather a method of treatment that utilizes a unique combination of natural substances, such as those which have been listed as GRAS (Generally Regarded As Safe), which may be administered as a nutritional supplement, without a prescription. There is a particular need to provide a new orally active therapeutic supplement which effectively addresses the primary defects of insulin resistance and insulin failure without side effects, so that the supplement can be administered to those who are in the pre-diabetic stages, or who exhibit pre-diabetic symptoms, so as to forestall or preclude the onset of diabetes.

When sugar is absorbed from the early portion of the jejunum, the sugar quickly reaches the beta cells of the pancreas and gets in these pancreatic cells via the glut 2 glucose transporter. The amount of sugar in the blood plasma is directly proportional to the sugar being transported into the beta cells. The glucose inside the beta cells is metabolised and oxidized, which produces a stimulation of insulin release that is augmented by the simultaneous stimulation of the gastric inhibitor peptide gip and glucagon-like peptide glp1 which occurs due to the oral ingestion of sugar.

When insulin is released into the body, it exerts an effect at the cellular level throughout the entire body, but more specifically in the liver, the muscle tissues, and the fat or adipose tissues. The effects can occur in a "short acting" way that stimulates the glucose uptake in muscles and fat cells, thereby increasing the synthesis of glycogen in muscle and liver, inhibiting glucose secretion in the liver, and increasing amino acid uptake, or in a "long term" way which increases protein synthesis and stimulates certain gene expression in all cells. Insulin works by binding with insulin receptors on a cell surface. Once coupled, kinase enzymes push glut 4, the major glucose transport receptor, to attach to the cell surface for driving the glucose intracellularly.

It is generally known that the surface of muscles and fat cells have other receptors that can drive the glucose intracellularly without insulin. These receptors work with IGF1 and IGF2 hormones. There is also believed to be a undefined IRR receptor structurally similar to the receptors working with IGF1 and IGF2 hormones located on the cell surface but the correlating hormone has not yet been found.

In general, the body should maintain a substantial equilibrium, that is, the amount of insulin secreted should be equal to the amount of insulin needed to keep the blood sugar level steady.

One problem that can be experienced is when insulin is not being adequately produced, typically because the pancreas, and more specifically the beta cells, have been destroyed or are sick as per type one diabetes, where the output of insulin is decreased or absent. A second problem is where insulin interactions, that is between the insulin, the insulin receptors, and the cells, are hindered by a multitude of factors so that the action is not an efficient use of the insulin available, and as a result, much more insulin is needed to achieve the same goal of driving the sugar intracellularly.

This second type of problem is associated with noninsulin dependent diabetes or adult onset diabetics, or a different syndrome of insulin resistance. It is this type of insulin inefficiency that the present method and composition are directed to.

Insulin resistance or insulin insensitivity encompasses the majority of the population dealing with diabetes; Type A, a genetic defect of the insulin receptors (i.e., leprechaunism, Rabson Mendhall syndrome, and lipodystrophy); Type B, an autoimmune type with an antibody to the insulin receptors; and Type 3, a post membrane receptor resistance, that includes obesity, hypertension, noninsulin dependent diabetes, aging, and polycystic ovary syndrome.

The commonly accepted theory for these two types of insulin resistant afflictions is that the sugars are not being transported into the cells due to an autoimmune antibody (Type B) or some sort of post receptor resistance (Type 3). As a result, sugars outside of the cells build up. The pancreas, attempting to equilibrate the level of sugar and insulin, causes insulin production to increase. Even though more insulin is being produced, sugars are not being transported into the cells. Initially, the increase in insulin is capable of overcoming the insulin resistance but this requires a much higher level of insulin production. This stage is Considered the pre-diabetic stage where insulin is high but glucose is normal. Ultimately, the pancreas becomes exhausted and it is not capable of keeping up with the high insulin production rate that is required, thereafter causing the sugar levels to spike, with the person eventually becoming a full diabetic.

The common non-invasive treatment for diabetics is to start and maintain a proper diet and exercise routine. Second, doctors may prescribe medication such as (i) sulphonyureas to stimulate over secretion of insulin, which can speed up the exhaustion of the pancreas; (ii) metformin prescribed to improve the efficiency of insulin action and also improve on the clearance of glucose in peripheral tissues, therefore decreasing the level of sugar and insulin as well; and (iii) IGF1 injection to decrease the level of insulin as well as blood sugar by activating the kinase via its own receptors.

While pre-diabetics have been treated at times with the same medications, the side effects of the medications made it difficult for the patient to improve their health since the foregoing treatments were designed for full diabetics.

SUMMARY OF THE INVENTION

The inventors have discovered that the once-daily administration, preferably once-daily of an ileum-targeting, delayed and/or controlled release dosage form containing a nutritional substance to a fasting subject—at a time of around four and one-half to around ten to twelve hours, preferably around six to around nine hours prior to the subject's next intended meal (most preferably at bedtime)) or in AM—induces satiety in the subject for a period of around twelve hours and preferably twenty-four hours or more (effect can be cumulative depending on the duration of taking the dosage). Alternatively, a dosage may be administered at least twice daily, preferably once before bedtime and once within the first two hours (preferably first hour) of waking. Alternatively three dosages may be administered— once in the morning, once in the afternoon and once before bedtime. While not wishing to be bound by any theory, the inventor believes that the nutritional substance stimulates the "ileal-brake" effect at a particularly advantageous point during a subject's feeding cycle and thereby induces satiety for an extended period of time (for at least about three hours, at least about six hours, at least about twelve hours or as long as twenty-four hours or longer). Compositions and methods of treatment of the invention therefore also prove particularly useful in the treatment or prevention of overweight, overeating, obesity and obesity-related disorders, as well as the treatment of noninsulin dependent diabetes mellitus, pre-diabetic symptoms, metabolic syndrome and insulin resistance, as well as disease states and conditions which occur secondary to diabetes, pre-diabetes, metabolic syndrome and insulin resistance, as well as polycystic (fibrous) ovaries, arteriosclerosis and fatty liver, as well as cirrhosis. The present methods also may be used to increase muscle mass and decrease fat in a subject.

Notably, compositions and methods of treatment of the invention modulate ileum ileal hormone and blood insulin and sugar levels relatively consistently in a variety of tested human subjects and can therefore be used to diagnose the presence of new or established disorders related to absolute or relative deficiency or excessive secretions of one or more hormones of the ileal break, and relative response to the stimuli in the overweight or obese, or in obese related disorders or likely onset of obesity or obesity-related disorders. Compositions according to the present invention may also be used to increase blood concentrations of insulin-like growth factor I and II (IGF1 and IGF2) as well as leptin in a subject.

Accordingly, in one embodiment, the invention provides a method of treatment comprising inducing satiety in a subject for a period of at least around twenty-four hours by once-daily administration to the subject of a delayed and/or controlled release dosage form. The dosage form is administered while the subject is in the fasted state and at a time of around six to around nine hours prior to the subject's next intended meal. The dosage form comprises an enterically-coated, ileum hormone-stimulating amount of a nutritional substance and releases the majority of the nutritional substance in vivo upon reaching the subject's ileum.

In some embodiments, satiety is induced in a subject who is overweight, or suffers from obesity or an obesity-related disorder, as determined by the BMI of the subject or patient.

In another embodiment, the invention provides a method of treatment comprising reducing and/or stabilizing a subject's blood sugar and insulin levels, decreasing insulin resistance, for a period of at least around twenty-four hours by once-daily administration to the subject of a delayed and/or controlled release oral dosage form. The dosage form is administered while the subject is in the fasted state and at a time of around six to around nine hours prior to the subject's next intended meal. The dosage form comprises an enterically-coated, ileum hormone-stimulating amount of a nutritional substance and releases the majority of the nutritional substance in vivo upon reaching the subject's ileum.

In still another embodiment, the invention provides a method of treating a subject suffering from a gastrointestinal disorder by administering to the subject a delayed and/or controlled release oral dosage form comprising an enterically-coated, ileum hormone-stimulating amount of a nutritional substance. The dosage form is administered while the subject is in the fasted state and at a time of around four and one-half to ten hours, more preferably around six to around nine hours prior to the subject's next intended meal. The dosage form comprises an enterically-coated, ileum hormone-stimulating amount of a nutritional substance and releases the majority of the nutritional substance in vivo upon reaching the subject's ileum.

In still other embodiments, the invention provides methods of inducing satiety, stabilizing blood sugar and insulin levels, and treating gastrointestinal disorders comprising once-daily administration to a subject in need thereof of an delayed and/or controlled release composition which may comprise an emulsion or a microemulsion containing an ileum hormone-stimulating amount of a nutritional substance. The composition is administered while the subject is in the fasted state and at a time of around four to ten, preferably around six to around nine hours prior to the subject's next intended meal. The composition releases the majority of the nutritional substance in vivo upon reaching the subject's ileum.

In preferred embodiments of the aforementioned methods of treatment of the invention, the dosage form is administered once-daily at bedtime, or in AM. By administering the dosage form to a subject in the fasted state at around four to ten, around six to around nine hours prior to the subject's next intended meal, and delivering substantially all of the nutritional substance to the ileum, methods and compositions of the invention achieve improved levels of plasma gastrointestinal hormones and prove useful in the treatment or prevention of one or more of obesity, obesity-related disorders, and gastrointestinal disorders, as well as metabolic syndrome and/or type II diabetes mellitus. The benefit of obtaining at least twenty-four hour appetite suppression or feeling of satiety and improved blood sugar and insulin levels from a single oral dosage of an inexpensive nutritional substance increases the likelihood that the subject will adhere to the methods of treatment for an extended time, thereby achieving a maximum health benefit. Further, compositions and methods of the invention utilize nutritional substances that are free of the safety and cost concerns associated with pharmacological and surgical intervention, and can induce long-term satiety with no or a minimal caloric intake.

In another embodiment, the invention provides a delayed and/or controlled release oral dosage form comprising an effective amount of a nutritional substance, preferably D-glucose or dextrose in an amount effective when released in the ileum to stimulate or inhibit the release of hormones in that portion of the small intestine of a subject or patient. This dosage form is administered in accordance with, and achieves the advantages of, the aforementioned methods of treatment of the invention. In addition, the present invention provides a method for diagnosing metabolic syndrome (glucose intolerance) and/or type II diabetes in a patient or subject.

Thus, the present method provides a means of stimulating or inhibiting the hormones (depending on the hormone) of the ileum in an easy and reproducible or standardized way which did not exist prior to the present method. Pursuant to the present application, the testing on a large scale of the ileal release to study and classify the variation or pathology of the hormone releases as such release relates to satiety and related pathological states and conditions, and the effect these hormones have on the rest of the metabolic and hormonal status of the body is another aspect of the invention. Thus, the present method allows the introduction of one or more dosages in oral dosage form to the ileum of the patient which can be standardized sufficiently to allow the creation of a normal reference range for the hormonal stimulation. It has been discovered that the present invention can be used to probe different diseases stemming from the relative or absolute increase or decrease of the ileal hormones, not only in treating the overweight/obesity metabolic syndrome axis but a number of other gastrointestinal diseases as otherwise described herein.

The present method also can be used to diagnose and treat a number of gastrointestinal disorders and/or conditions which may occur as a consequence of infection, medical treatment or diseases of atrophy, including atrophic gastritis, post chemotherapy disorder, intestinal motility disorder (gut dismotility), mild reflux, chronic pancreatitis, malnutrition, malabsorption, voluntary or involuntary long term starvation, post infectious syndrome, short bowel syndrome, irritable bowel, malabsorption, diarrheal states, post chemotherapy gastrointestinal disorder, post infectious syndrome, radiation enteritis, chronic pancreatitis, celiac disease, fatty liver disease, cirrhosis, radiation, inflammatory bowel disease and Crohn's disease, among others.

In another embodiment, the invention may be used to improve the health of the liver, improve the pancreas health, as well as the health of the intestine, and to decrease/ameliorate fatty liver, to increase the size of pancreatic beta cells (hyperplasia) in the pancreas as well as increase the size of the absorptive villae of the small bowel.

In another embodiment, the method of preparation of the pills can be used in combination with traditional bioactive agents (medication) delivery by itself or together with the core to deliver the content specifically to the ileum for targeted therapy avoiding absorption, side effects and increasing the yield of the therapy, such as specialized antibiotics, antispasmodic agents, non-specific chelating agents, antibacterial agents, antidiabetes agents, laxatives among numerous others, including natural plant oils such as olive oil, vegetable and animals oils, fats, such as animal fats, butter and vegetable fat, oils and fats from seeds and nuts, stimulants including caffeine, herbs, teas, ingredients that increase post receptor activities at the cellular level, selected extracts or food products and chemicals, natural or otherwise, including metabolites.

In another embodiment, the invention provides a method for diagnosing metabolic syndrome (glucose intolerance) and/or type II diabetes in a patient the present invention approaches the problem of satiety in a natural physiological manner by stimulating hormones in the ileum which act synergistically to provide satiety for a period of at least about 12 hours and preferably at least about 24 hours. It does this most preferably using natural nutritional components in healthful, pleasant compositions which are preferably coated using a polymeric, preferably aqueous pH-sensitive (dissolution/release of contents of formulation occurs at a pH of the ileum, or a pH of approximately 7-8, preferably 7.2-8.0, about 7.4-8.0, about 7.5-8.0) shellac nutrateric coating to effect a natural physiological response within the subject's ileum with favorable results. The present invention represents a change in the nature of inducing satiety in a subject to a more wholesome, natural physiological process, completely distinguishable over pharmaceutical or synthetic approaches.

In other particular embodiments, orally administering a nutritional supplement composition containing an effective amount, more particularly, an ileal hormone stimulating effective amount of a sugar such as dextrose or other nutritional substance as otherwise described herein, optionally combined with one or more of other advantageous substances such as alfalfa leaf, chlorella algae, chlorophyllin and barley grass juice concentrate, and further formulated with a delayed release base adapted to release the composition in the lower gut, in particular the ileum, has been shown to result in normalized blood sugar and insulin levels. In particular, in subjects where there previously was shown to be an absence of elevated blood sugar but the subjects exhibited high insulin levels, that is, pre-diabetic symptoms, administering the supplement caused a decrease in insulin levels back to a normal range while glucose levels remained normal (reduced and/or stabilized). In other words, the body system achieved substantial equilibrium, with substantially no side effects reported. The result was similar to what can be achieved administering drugs such as Metformin and IGF-1, but with a drug free natural food supplement, with relatively few, if any, side effects.

Without being limited by way of theory, it is believed that by stimulating the ileal hormones contained in the lower gut, the inventive nutritional supplement drives the sugar intercelluarly by either (i) stimulating the production or increasing the level of IGf-1 and/or IGF-2 and/or leptin that will act on their own receptors, (ii) direct action on IGF-1 and/or IGF-2 and/or leptin receptors, or (iii) stimulating one or more intestinal hormones, including a new intestinal hormone that will act on its own receptors as per the IRR receptors.

Accordingly, in another embodiment, the invention provides a method of treating noninsulin dependent diabetes mellitus, pre-diabetic symptoms, metabolic syndrome, increasing glucose tolerance and/or decreasing insulin resistance by reducing insulin levels in the bloodstream comprising administering a nutritional supplement composition containing an effective amount of a sugar, such as dextrose or other nutritional substance as otherwise defined herein, optionally and preferably combined with one or more of alfalfa leaf, chlorella algae, chlorophyllin and barley grass juice concentrate or sodium alginate, alone or in combination with the other ingredients and further formulated with a delayed release base adapted to release the composition in the lower gut (ileum), that is, in a delayed and/or controlled release dosage form. The dosage form may comprise the nutritional supplement in a unit or partial dose form and have an enteric coating, including a nutrateric coating (e.g., containing shellac as a polymeric material, hypromellose, as an emulsifier, thickener and suspending agent and triacetin as an emulsifier). Alternatively, the nutritional substance (preferably D-glucose or dextrose) and optionally, one or more of alfalfa leaf, chlorella algae, chlorophyllin and barley grass juice concentrate may be combined with binders, diluents, additives and other pharmaceutical additives such as one or more of a filler, compressibility enhancer (e.g., corn starch or lactose), lubricant (stearic acid), extrusion agent (magnesium stearate), silicon dioxide (dispersing agent), and enteric coated or nutrateric coated with a coating which dissolves at the pH of the ileum and includes one more polymeric components as otherwise described herein.

In another embodiment, the invention provides a method which comprises equilibrating a subject's insulin level to compliment a blood sugar level, preferably by once-daily administration to the subject of a delayed and/or controlled release oral dosage form of the invention.

In still another embodiment, the invention provides a method of treating a subject exhibiting pre-diabetic symptoms comprising administering a nutritional supplement composition containing an effective amount (generally, at least in part, to reduce insulin) of a sugar such as dextrose (glucose) or other nutritional substance as otherwise described here, either alone, or preferably in combination with one or more of alfalfa leaf, chlorella algae, chlorophyllin and barley grass juice concentrate, in a delayed and/or controlled release dosage form, adapted to release the composition in the lower gut, the combination providing an insulin reducing effect so as to equilibrate the amount of insulin produced to correspond to the amount of blood sugar. The dosage form may comprise the nutritional supplement in a unit or partial dose form and having an enteric coating.

By administering the nutritional supplement to a person who exhibits noninsulin dependent diabetes mellitus, pre-diabetic symptoms, and/or insulin resistance, reduced levels of insulin are produced so as to avoid the "over-working" of the pancreas, thereby reducing stress on the pancreas which may forestall, for example, in someone exhibiting pre-diabetes symptoms, the onset of full blown diabetes. Thus, the present invention also has the advantage of reducing the likelihood that a patient or subject with metabolic syndrome or noninsulin dependent diabetes mellitus (type II diabetes) will see these conditions advance to insulin dependent diabetes mellitus (type I diabetes). One benefit of the present invention is that this result can be achieved by administering a relatively inexpensive nutritional supplement, formulated using GRAS ingredients to assure safety, which substantially diminishes cost and avoids as well the side effects associated with drug therapies.

Other aspects of the invention relate to compositions which comprise an effective amount of a nutritional substance as otherwise described herein, preferably glucose or dextrose which is formulated in delayed and/or controlled release dosage form in order to release an effective amount of nutritional substance in the ileum of the patient or subject to whom compositions according to the present invention are administered, generally, at least about 50% of the total amount of the nutritional substance present, and preferably at least about 70%, at least about 75%, at least about 80%, at least about 85%, at least about 90%, and at least about 95% or more of the nutritional substance present in the composition. In the case of D-glucose or dextrose as the nutritional substance, it is preferred that at least about 2.5 grams, at least about 7.5 grams and more preferably about 10-12.5 grams or more of glucose be released in the patient's or subject's ileum in order to stimulate ileal hormone release. Compositions according to the present invention comprise effective amounts of a nutritional substance, preferably D-glucose or dextrose, which may be combined with at least one delayed or controlled release component such as a delayed/controlled release polymer or compound such as a cellulosic material, including, for example, ethyl cellulose, methyl cellulose, hydroxymethylcellulose, hydroxypropylcellulose, polyvinylpyrrolidone, cellulose acetate trimellitiate (CAT), hydroxypropylmethyl cellulose phthalate (HP-MCP), polyvinyl acetate phthalate (PVAP), cellulose acetate phthalate (CAP), shellac, copolymers of methacrylic acid and ethyl acrylate, copolymers of methacrylic acid and ethyl acrylate to which a monomer of methylacrylate has been added during polymerization, a mixture of amylose-butan-1-ol complex (glassy amylose) with Ethocel® aqueous dispersion, a coating formulation comprising an inner coating of glassy amylose and an outer coating of cellulose or acrylic polymer material, pectins (of various types), including calcium pectinate, carageenins, aligns, chondroitin sulphate, dextran hydrogels, guar gum, including modified guar gum such as borax modified guar gum, beta.-cyclodextrin, saccharide containing polymers, e.g., a polymeric construct comprising a synthetic oligosaccharide-containing biopolymer including methacrylic polymers covalently coupled to oligosaccharides such as cellobiose, lactulose, raffinose and stachyose, or saccharide-containing, natural polymers including modified mucopolysaccharides such as cross-linked pectate; methacrylate-galactomannan, pH-sensitive hydrogels and resistant starches, e.g., glassy amylose. Other materials include methylmethacrylates or copolymers of methacrylic acid and methylmethacrylate having a pH dissolution profile that delays release in vivo of the majority of the nutritional substance until the dosage form reaches the ileum may also be used. Such materials are available as Eudragit® polymers (Rohm Pharma, Darmstadt, Germany). For example, Eudragit® L100 and Eudragit® S100 can be used, either alone or in combination. Eudragit® L100 dissolves at pH 6 and upwards and comprises 48.3% methacrylic acid units per g dry substance; Eudragit® S100 dissolves at pH 7 and upwards and comprises 29.2% methacrylic acid units per g dry substance. Generally, the encapsulating polymer has a polymeric backbone and acid or other solubilizing functional groups. Polymers which have been found suitable for purposes of the present invention include polyacrylates, cyclic acrylate polymer, polyacrylic acids and polyacrylamides. A particularly preferred group of encapsulating polymers are the polyacrylic acids Eudragit® L and Eudragit® S which optionally may be combined with Eudragit® RL or RS. These modified acrylic acids are useful since they can be made soluble at a pH of 6 or 7.5, depending on the particular Eudragit chosen, and on the proportion of Eudragit® S to Eudragit® L, RS, and RL used in the formulation. By combining one or both of Eudragit® L and Eudragit® S with Eudragit® RL and RS (5-25%), it is possible to obtain a stronger capsule wall and still retain the capsule's pH-dependent solubility.

A delayed and/or controlled release oral dosage form used in the invention can comprise a core containing an ileum hormonal-stimulating amount of a nutritional substance along with carriers, additives and excipients that is coated by an enteric coating. In some embodiments, the coating comprises Eudragit® L100 and shellac, or food glaze Eudragit® S100 in the range of 100 parts L100:0 parts S100 to 20 parts L100:80 parts S100, more preferably 70 parts L100:30 parts S100 to 80 parts L100:20 parts S100. In preferred alternatives, the preferred coating is a nutrateric coating which dissolves at the pH of the ileum (about 7-8, about 7.2-8.0, about 7.4-8.0, about 7.5-8.0) comprising a shellac, and emulsifiers, such as triacetone and hypromellose, among others. Alternative nutrateric coatings include ethyl cellulose, ammonium hydroxide, medium chain triglycerides, oleic acid, stearic acid. As the pH at which the coating begins to dissolve increases, the thickness necessary to achieve ileum-specific delivery decreases. For formulations where the ratio of Eudragit® L100:S100 is high, a coat thickness of the order 150-200 μm can be used. For coatings where the ratio Eudragit® L100:S100 is low, a coat thickness of the order 80-120 μm can be used in the present invention.

In still further embodiments, the present invention relates to a method of improving muscle functions and coordination in a patient in need thereof comprising administering an effective amount of a composition according to the present invention in a patient in need thereof, optionally in combination with a bioactive agent. Additional methods according to the present invention relate to improving the action of traditional anti-diabetes medications, including ddpi 4 (DDPI IV) inhibitors, among others, that suppress glp1 inhibition/destruction and work to potentiate glp1 levels stimulated by compositions according to the present invention. The agents act in a synergistic manner to produce favorable results in diabetes (especially including type II) treatment.

In additional embodiments of the present invention, a method of treating impairment to or improving basal membrane structure of gastrointestinal tract comprises administering an effective amount of a compound according to the present invention to a patient in need thereof, optionally in combination with a bioactive agent. This method may be used to treat, inhibit or reduce the likelihood of multiple sclerosis in a patient or to enhance recovery from injury which occurs secondary to radiation, chemotherapy or other toxins.

The present method also relates to a method of treating or reducing the likelihood of liver disease such as fatty liver and various forms of hepatitis, including steatohepatitis and autoimmune hepatitis, as well as other types of hepatitis in a patient comprising administering an effective amount of a compound according to the present invention to a patient in need thereof, optionally in combination with a bioactive agent. Hepatitis includes hepatitis from viral infections, including Hepatitis A, B, C, D and E, Herpes simplex, Cytomegalovirus, Epstein-Barr virus, yellow fever virus, adenoviruses; non-viral infections, alcohol, toxins, drugs, ischemic hepatitis (circulatory insufficiency); pregnancy; autoimmune conditions, including Systemic Lupus Erythematosus (SLE); metabolic diseases, e.g. Wilson's disease, hemochromatosis and alpha one antitrypsin deficiency; and non-alcoholic steatohepatitis.

In still a further embodiment, the present invention relates to a treatment or inhibition of hyperlipidemia, especially hyperlipidemia associated with high triglycerides comprising administering to a patient in need thereof an effective amount of a compound according to the present invention, optionally in combination with a bioactive agent.

These and other aspects of the invention are explained further in the following detailed description of the invention.

BRIEF DESCRIPTION OF THE FIGURES

FIGS. 3A and B show the total stimulation above the baseline as a consequence of administration as a function of time to subjects. 2A is the total stimulation above the baseline for Case 1. 2B is the total stimulation above the baseline for Case 2.

FIG. 4 discloses a table A containing the statistical correlations undertaken in connection with the experiments of example 3.

FIG. 6F represents outlier results for patient I.

FIGS. 8A-J shows the results of glucose, insulin and C-peptide response in five groups of individuals following the ingestion of a formulation according to the present invention. 8A shows the results of glucose (mg/dl), insulin (μIu/ml) and C-peptide (ng/ml) response in individuals with normal glucose and mild elevation of insulin; 8B shows the results of glucose, insulin and C-peptide response in individuals with elevated glucose and normal to reduced/low levels of insulin; 8C shows the results of glucose, insulin and C-peptide response in individuals with elevated levels of glucose and insulin; 8D shows the results of glucose, insulin and C-peptide response in individuals with normal glucose and elevated fasting insulin and 8E shows the results of glucose, insulin and C-peptide response in individuals with normal glucose and mild insulin increase. 8F demonstrates the continual seesaw between insulin stimulation and suppression as it relates to suppression of insulin resistance as insulin trended down over time with insulin evidencing bouts of stimulation within a cycle. 8G and 8H show a decline in glucose and insulin consistently over time in individuals with normal glucose and elevated fasting insulin, 8I and 8J show an insulin reduction with decrease in blood glucose in individuals with normal glucose and mild insulin increase.

FIGURES FOR FURTHER EXAMPLES

Figure 29:
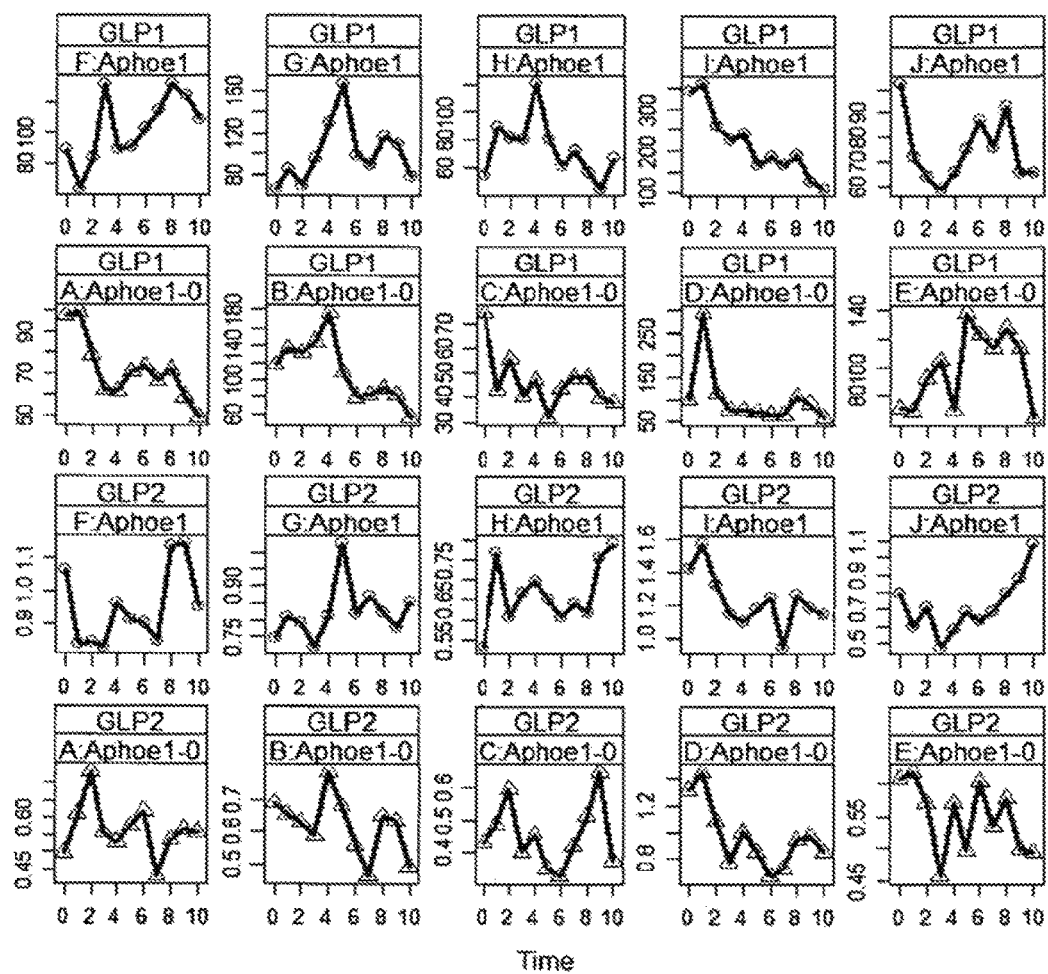

FIG. 29 (Further Examples) Testing Results for GLP1 and GLP2 by Formulation Aphoeline 0 and Aphoeline 1).

Figure 30:
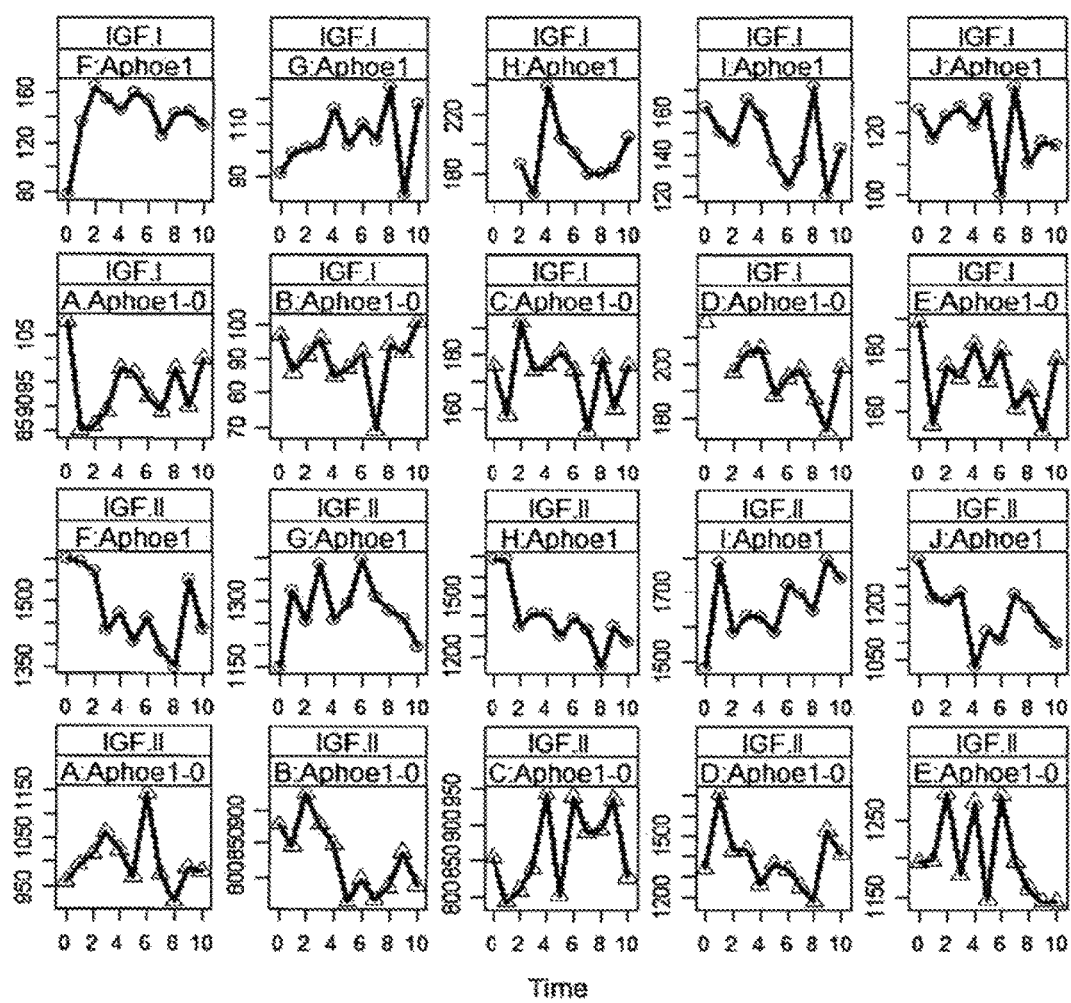

FIG. 30 (Further Examples) Testing Results for EGFI and IGF2 by Formulation Aphoeline 0 and Aphoeline 1).

Figure 31:
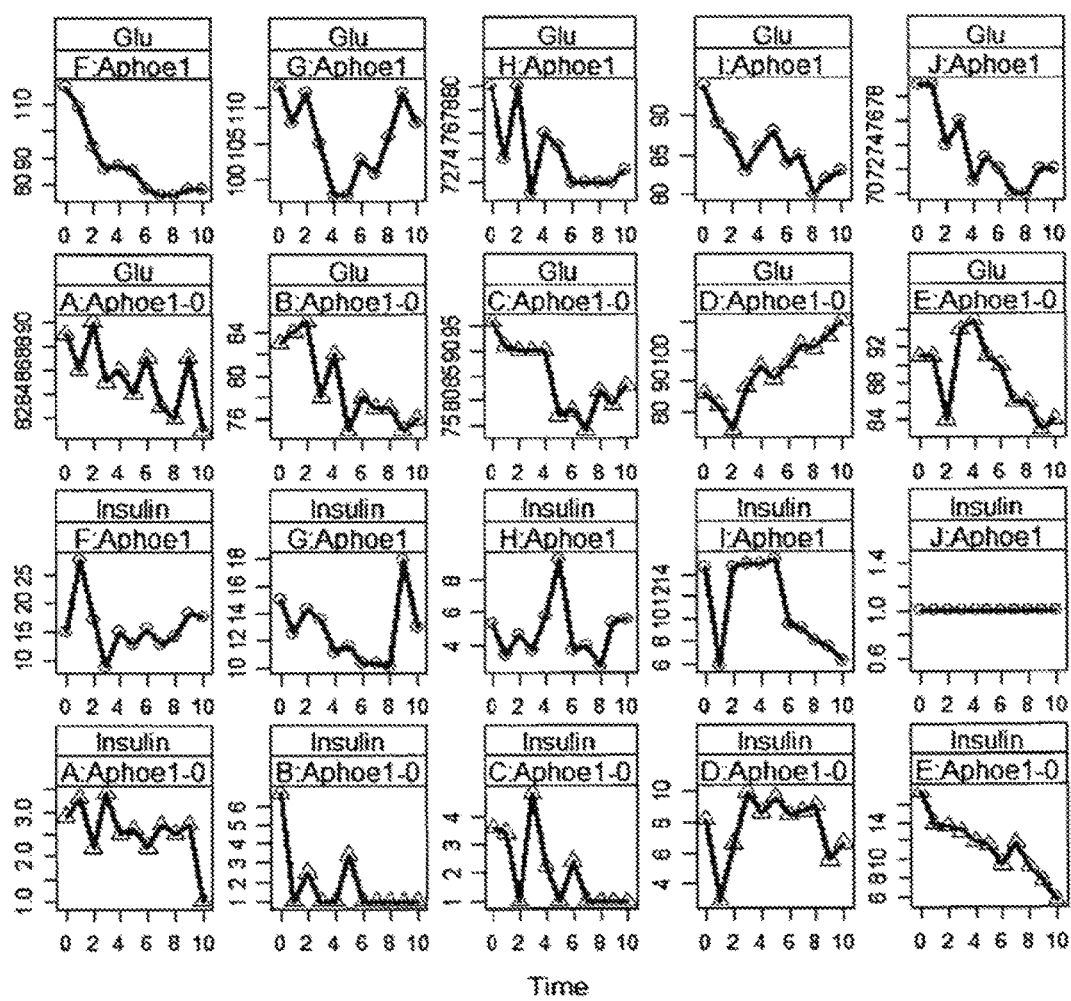

FIG. 31 (Further Examples) Testing Results for Glucose and Insulin by Formulation Aphoeline 0 and Aphoeline 1).

Figure 32:
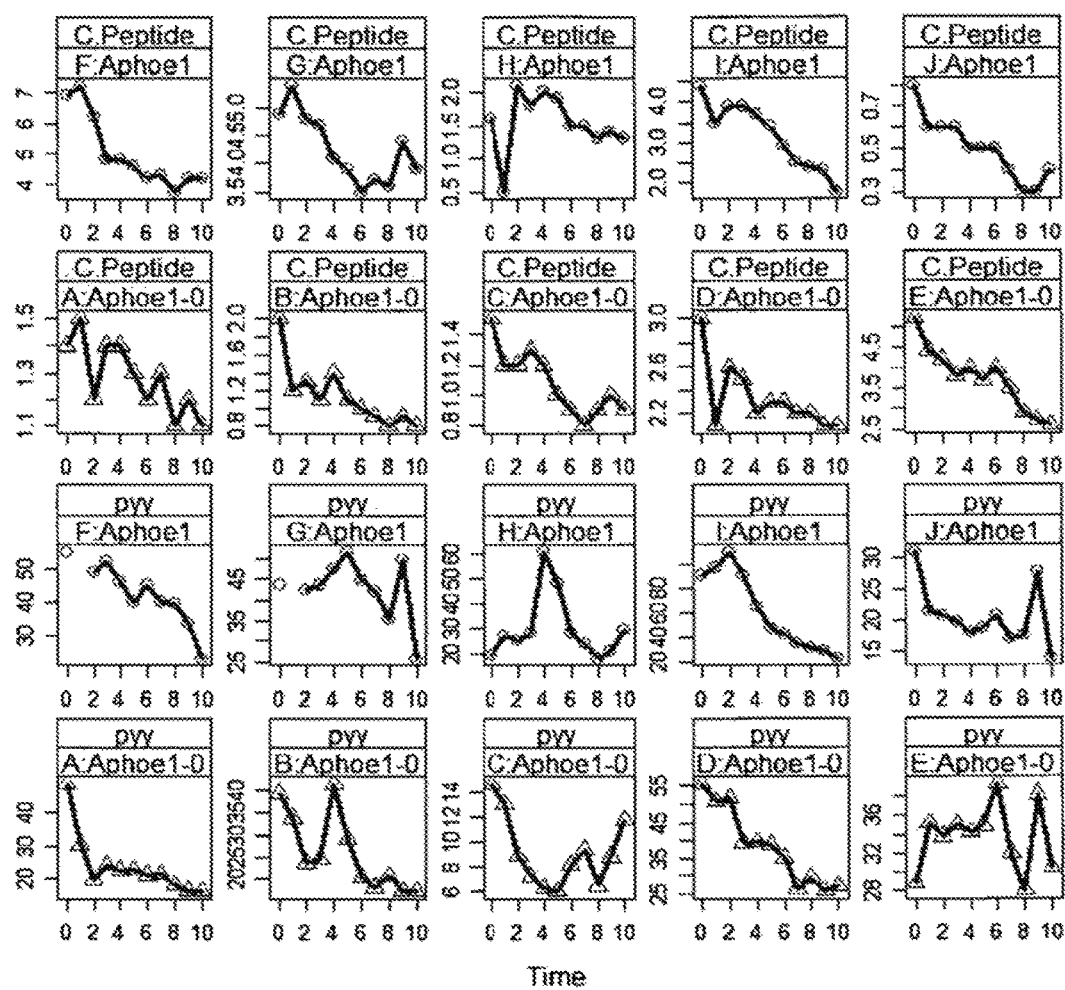

FIG. 32 (Further Examples) Testing Results for EGFI and IGF2 by Formulation Aphoeline 0 and Aphoeline 1).

Figure 33:
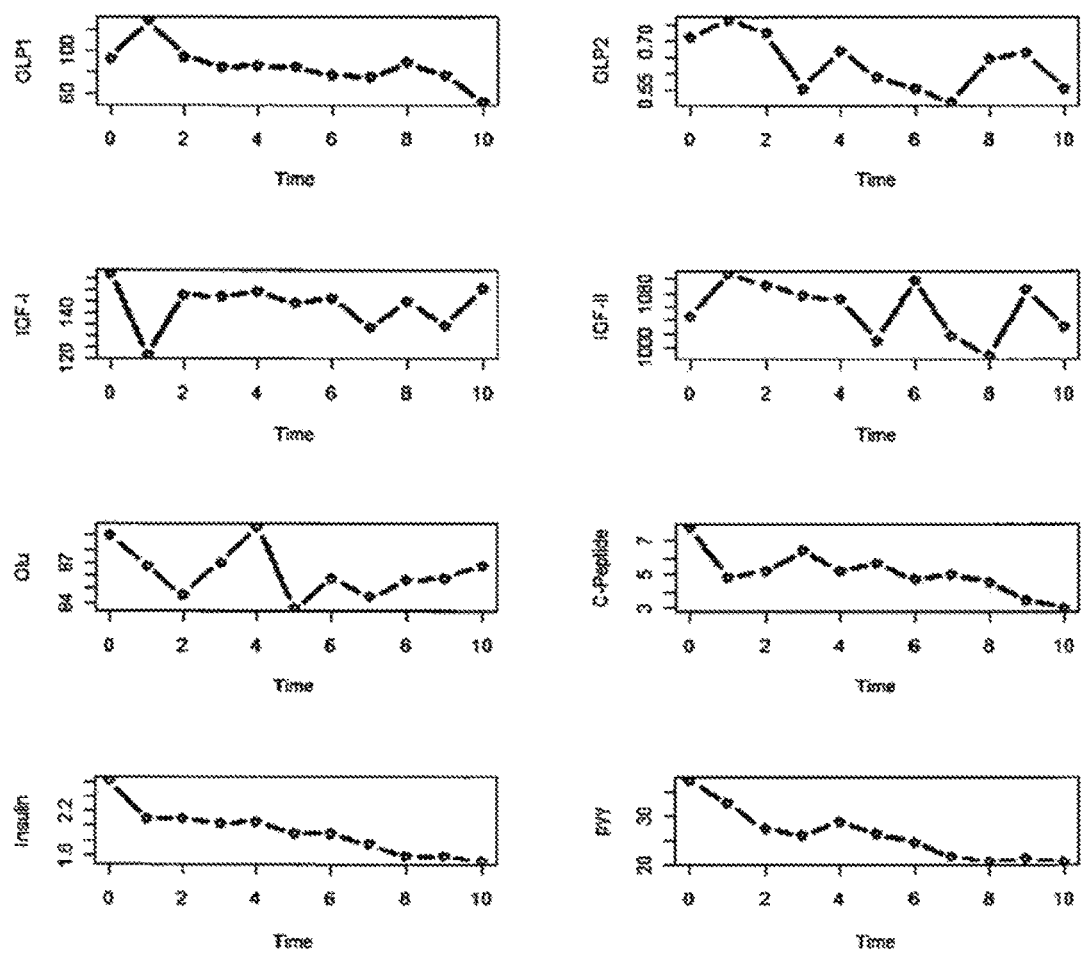

FIG. 33 (Further Examples) Average Levels for Aphoeline 0 Group.

Figure 34:
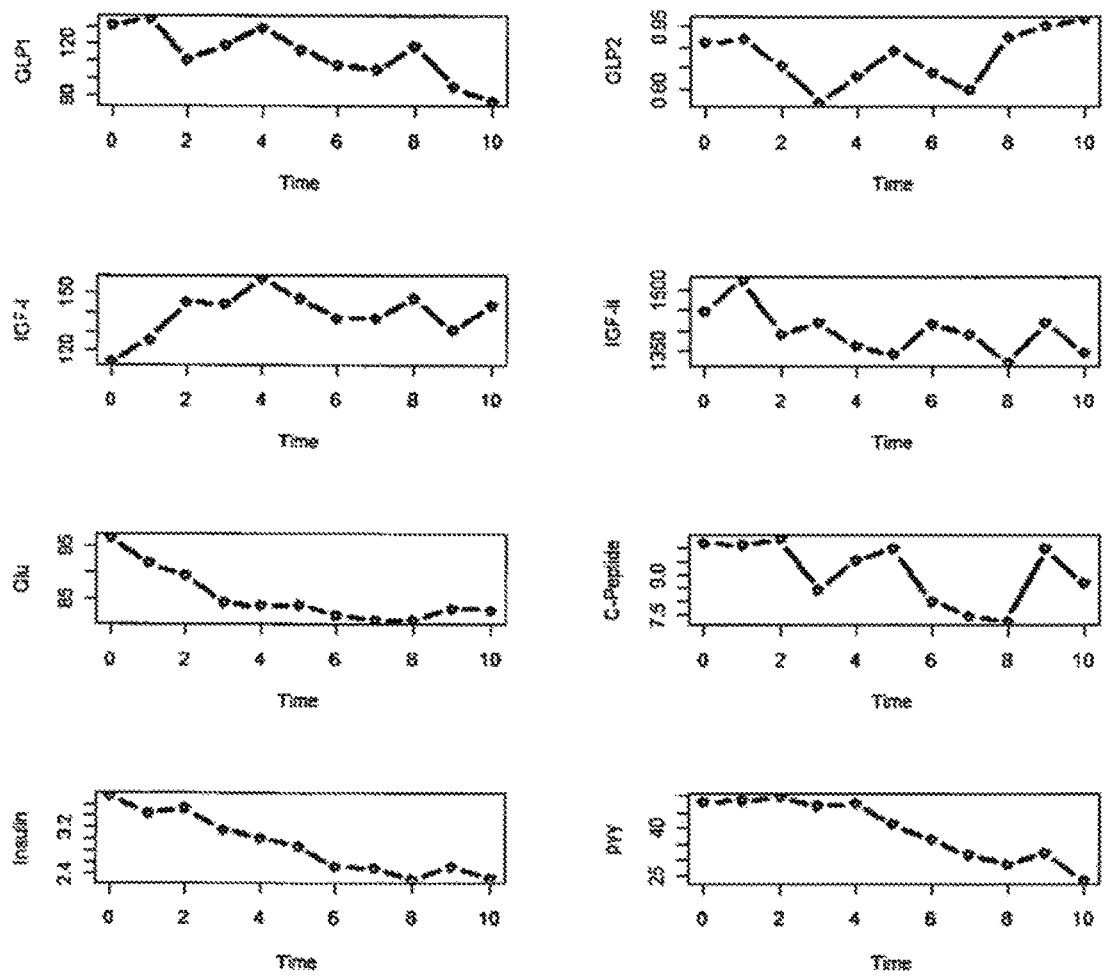

FIG. 34 (Further Examples) Average Levels for Aphoeline 1 Group.

Figure 35:
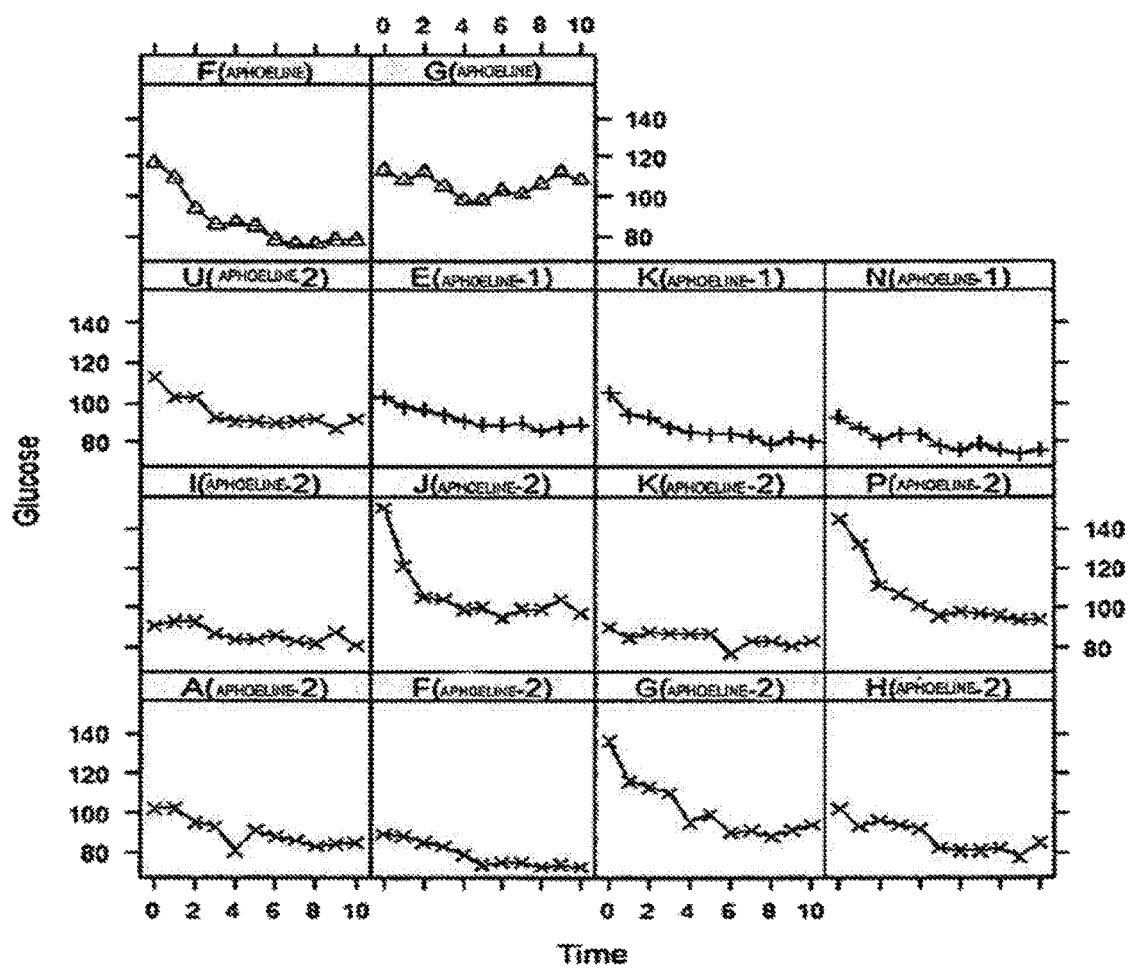

FIG. 35 (Further Examples) Glucose concentrations for subjects with elevated Glucose/Insulin concentrations.

Figure 36:
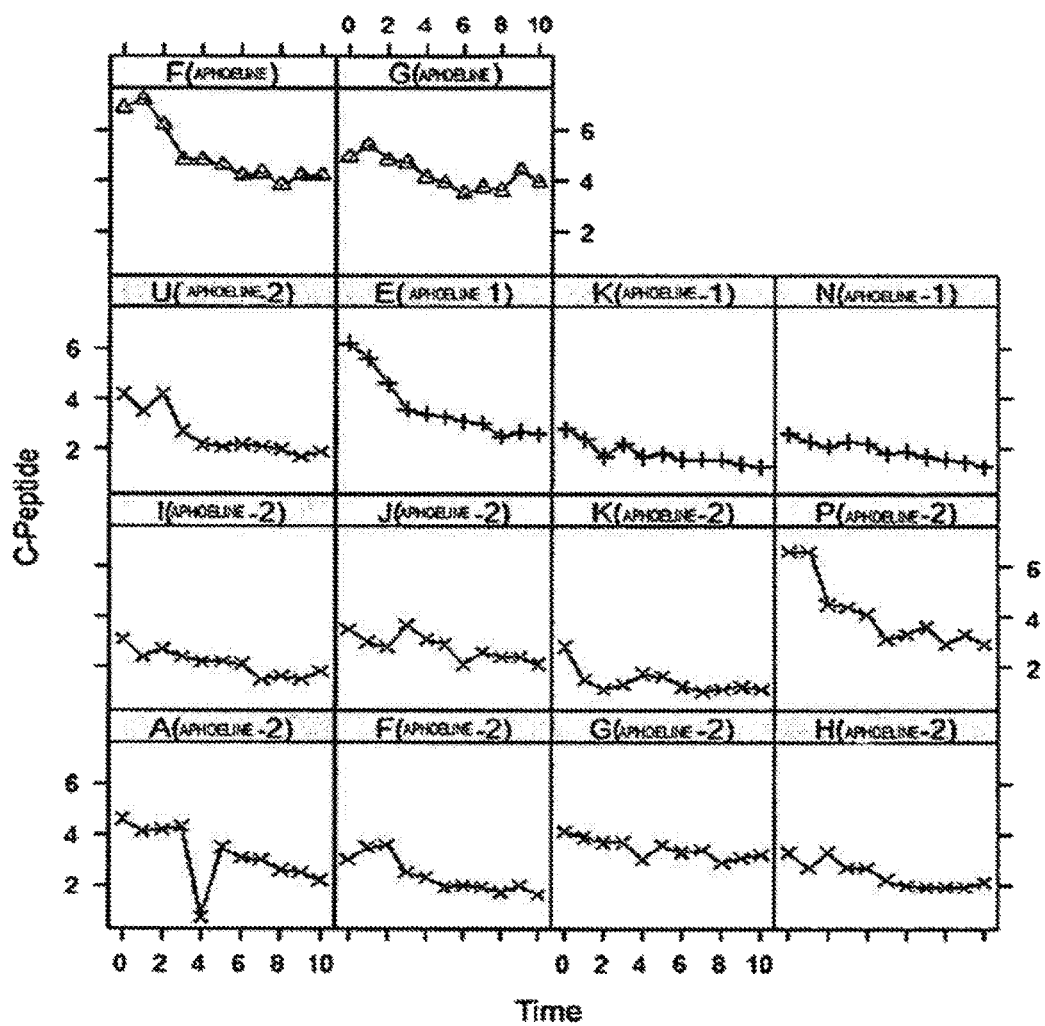

FIG. 36 (Further Examples) C-Peptide concentrations for subjects with elevated Glucose/Insulin concentrations.

Figure 37:
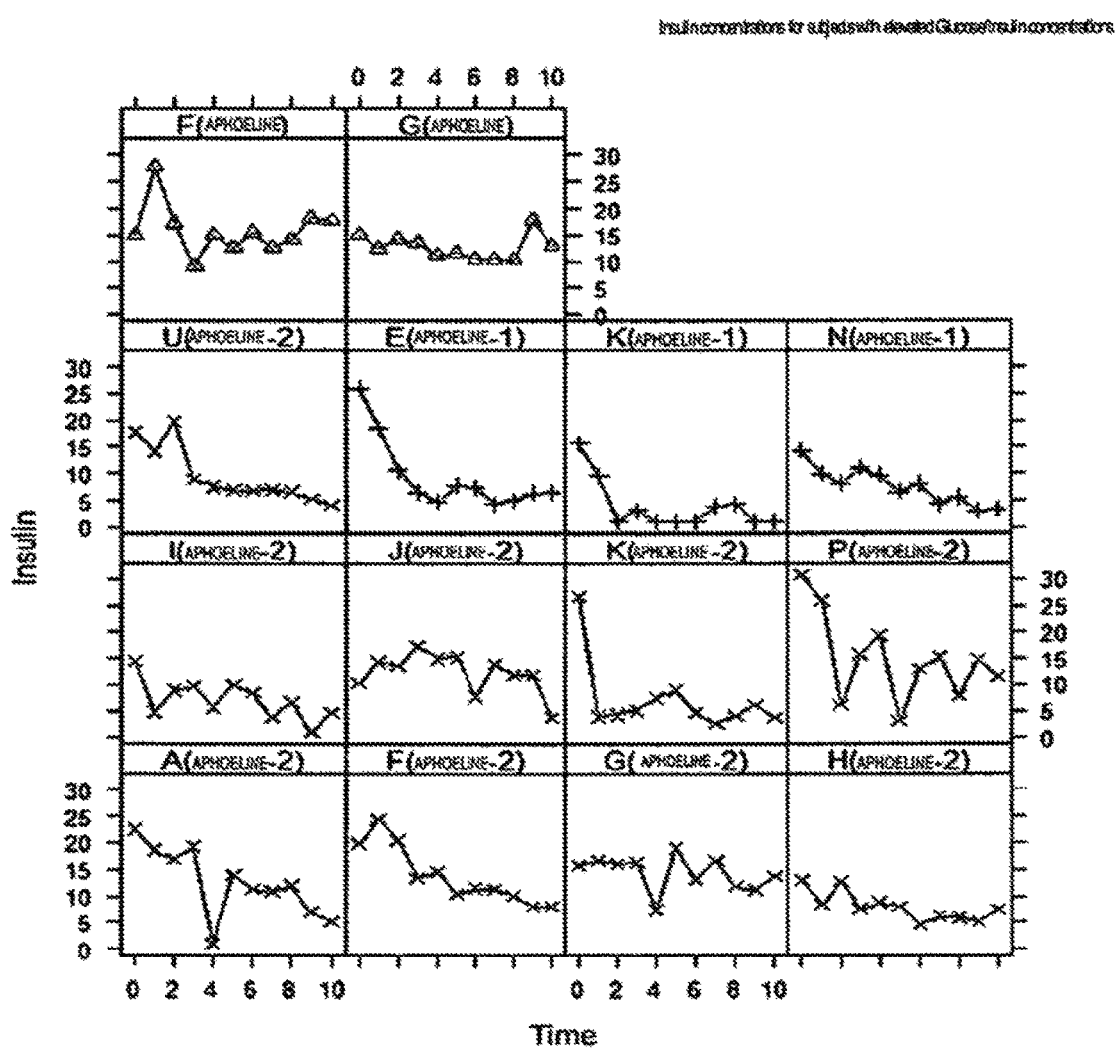

FIG. 37 (Further Examples) Insulin concentrations for subjects with elevated Glucose/Insulin concentrations.

Figure 11:
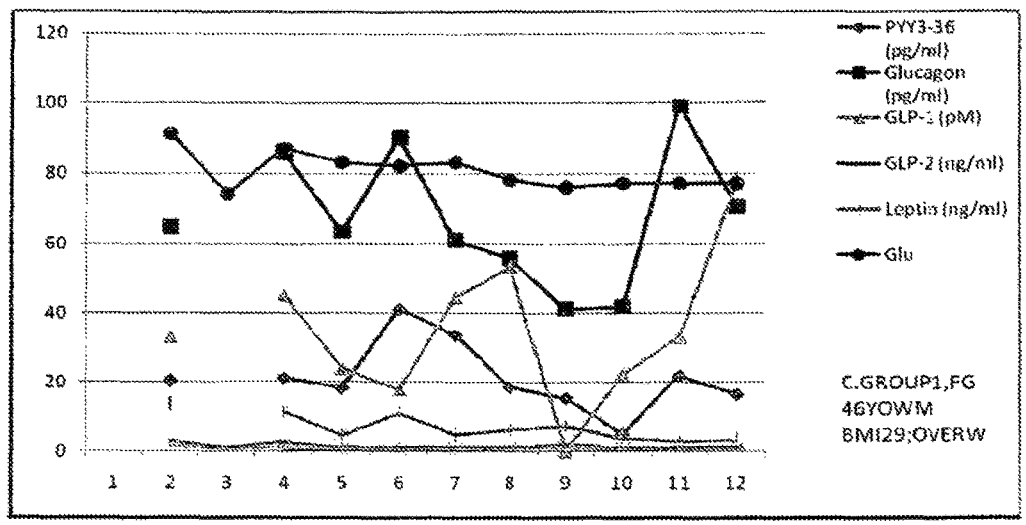
FIG. 11 is a chart showing the change in levels of various blood components during testing, with Table 3 showing the data, for the following subject: white male, 46 years old with a BMI of 29 (overweight)
Figure 12:
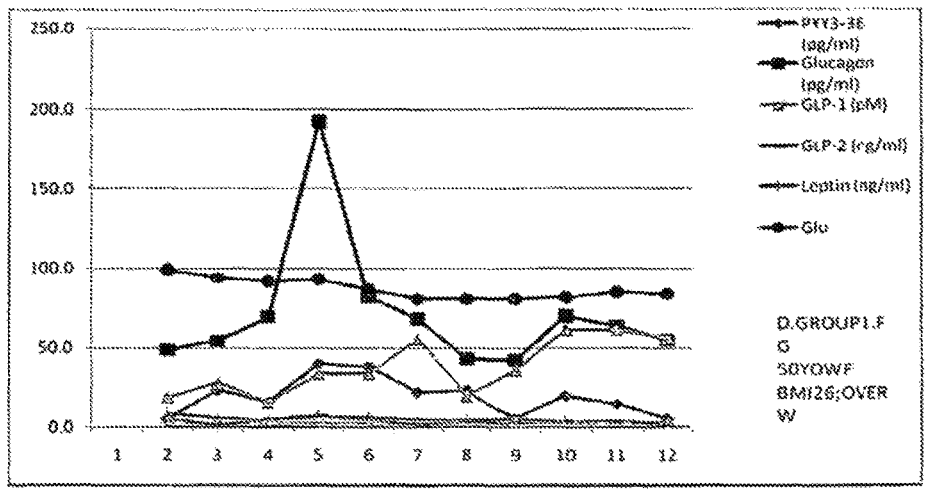
FIG. 12 is a chart showing the change in levels of various blood components during testing, with Table 4 showing the data, for the following subject: white female, 50 years old with a BMI of 26 (overweight)
Figure 13:
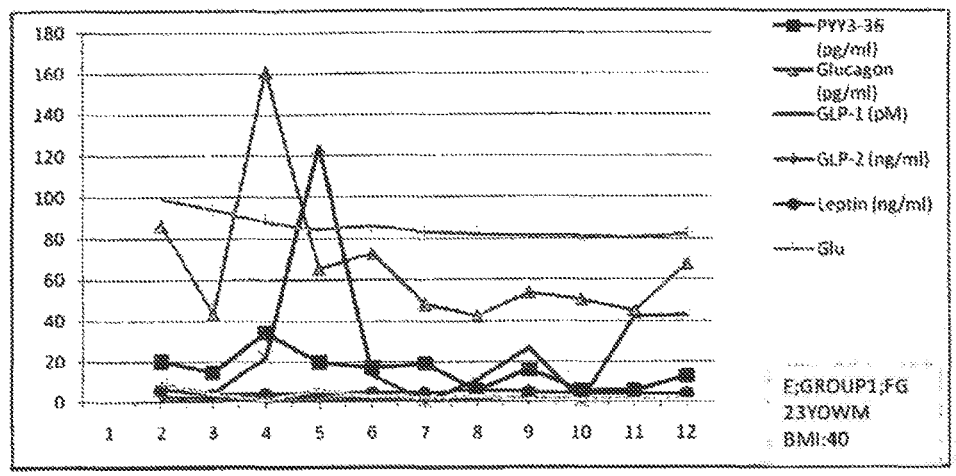
FIG. 13 is a chart showing the change in levels of various blood components during testing, with Table 5 showing the data, for the following subject: white male, 23 years old with a BMI of 40 (obese)
Figure 14:
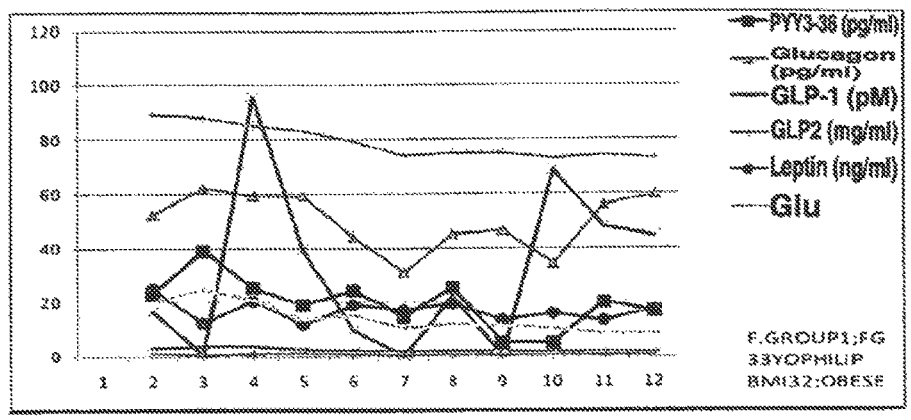
FIG. 14 is a chart showing the change in levels of various blood components during testing, with Table 6 showing the data, for the following subject: white male, 33 years old with a BMI of 32 (obese)
Figure 15:
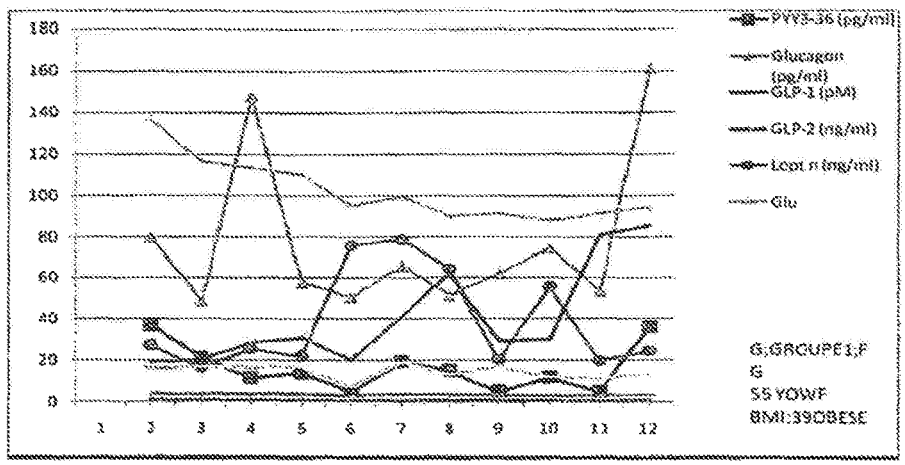
FIG. 15 is a chart showing the change in levels of various blood components during testing, with Table 8 showing the data, for the following subject: white male, 61 years old with a BMI of 34 (obese)
Figure 16:
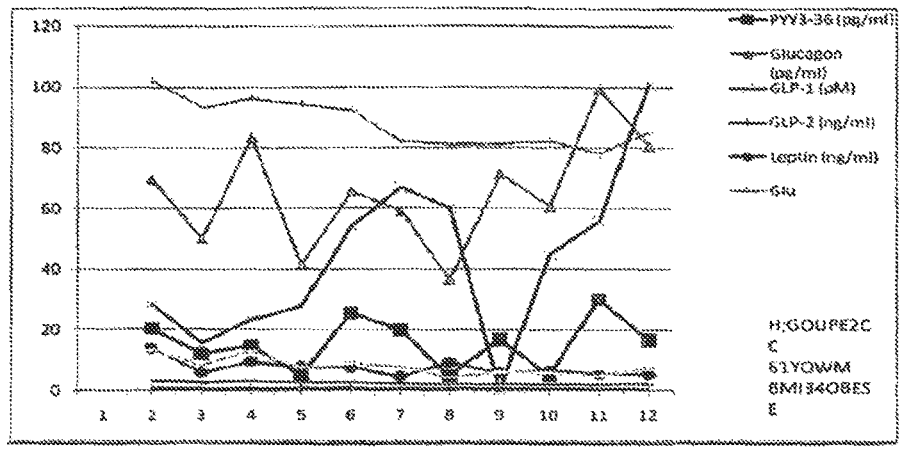
FIG. 16 is a chart showing the change in levels of various blood components during testing, with Table 9 showing the data, for the following subject: white male, 29 years old with a BMI of 26 (overweight)
Figure 17:
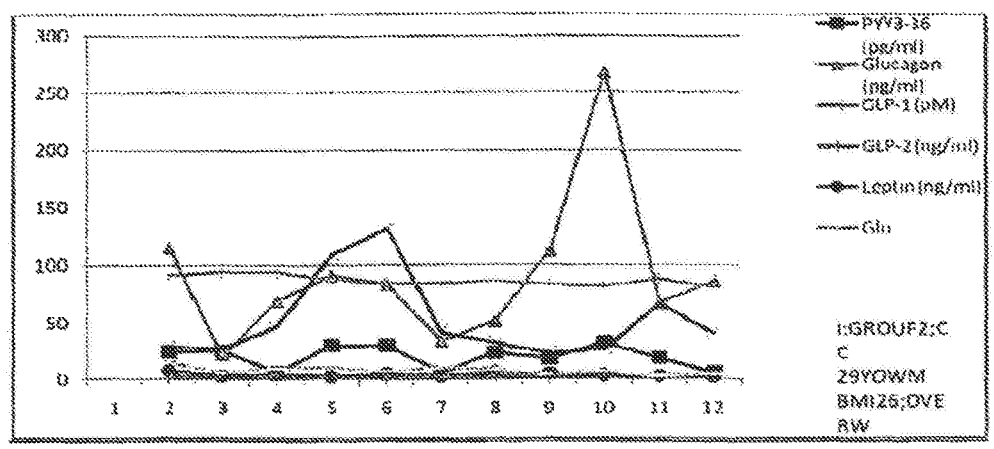
FIG. 17 is a chart showing the change in levels of various blood components during testing, with Table 10 showing the data, for the following subject: black female, 44 years old with a BMI of 37 (obese)
Figure 18:
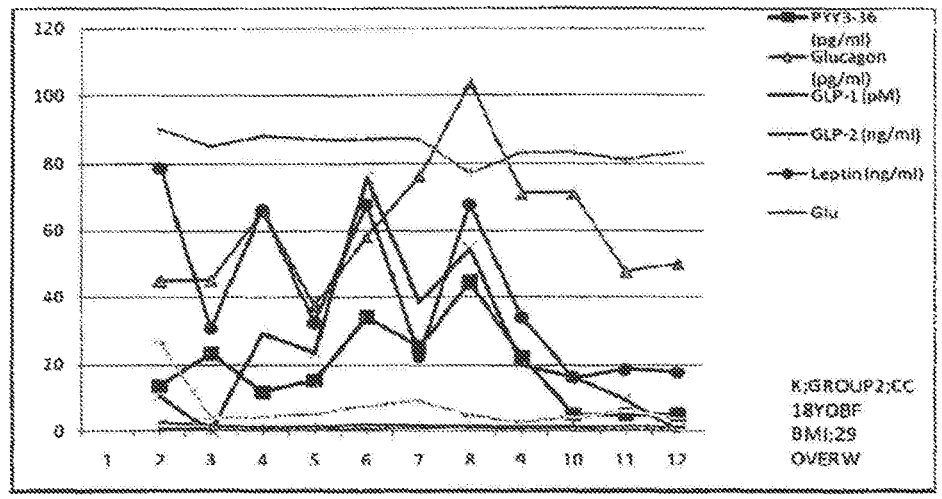
FIG. 18 is a chart showing the change in levels of various blood components during testing, with Table 11 showing the data, for the following subject: black male, 18 years old with a BMI of 29 (overweight)
Figure 19:
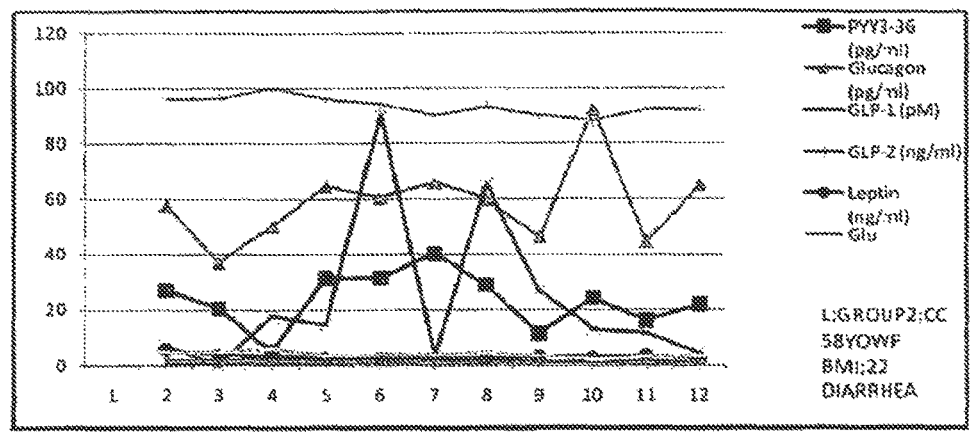
FIG. 19 is a chart showing the change in levels of various blood components during testing, with Table 12 showing the data, for the following subject: white female, 58 years old with a BMI of 22 (normal)
Figure 20:
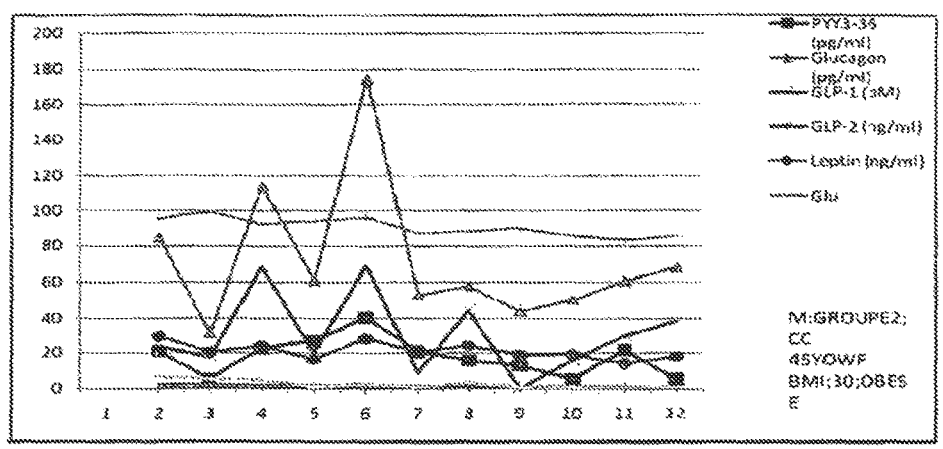
FIG. 20 is a chart showing the change in levels of various blood components during testing, with Table 13 showing the data, for the following subject: white female, 45 years old with a BMI of 30 (obese)
Figure 21:
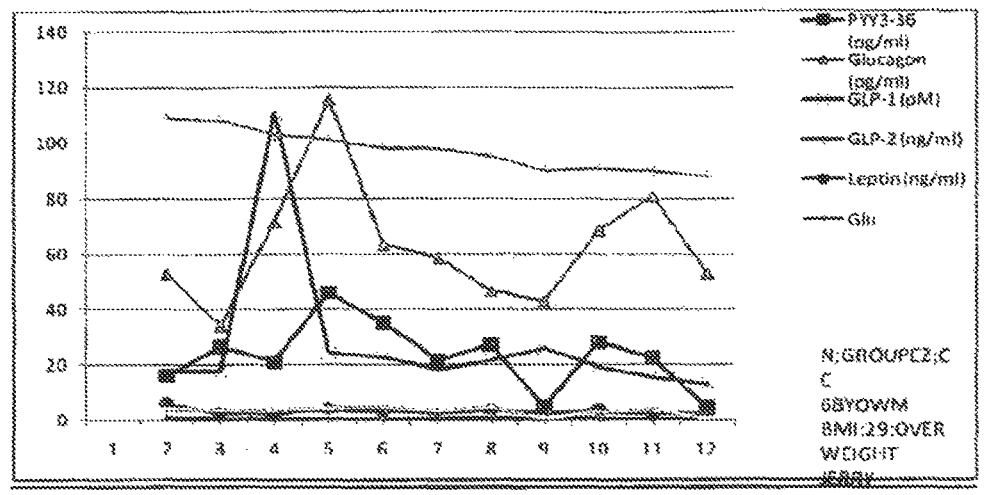
FIG. 21 is a chart showing the change in levels of various blood components during testing, with Table 14 showing the data, for the following subject: white male, 68 years old with a BMI of 29 (overweight)
Figure 22:
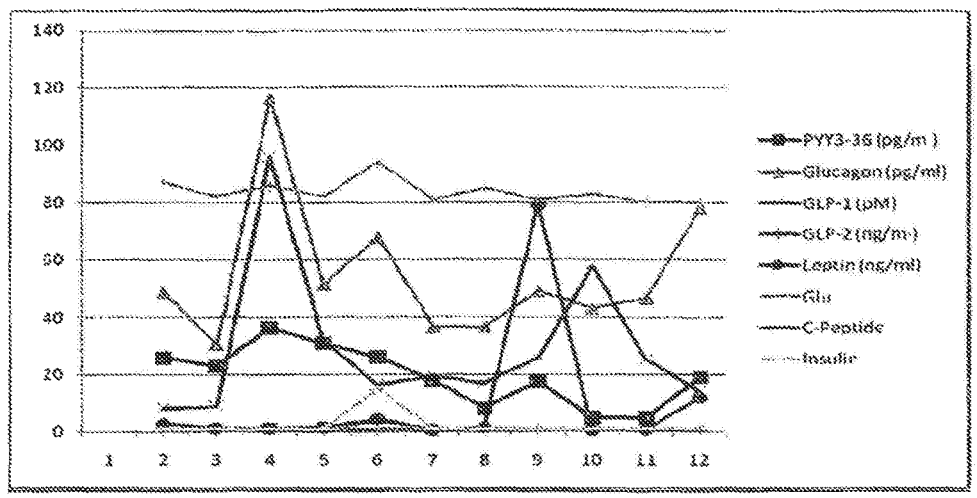
FIG. 22 is a chart showing the change in levels of various blood components during testing, with Table 15 showing the data, for the subject tested.
Figure 23:
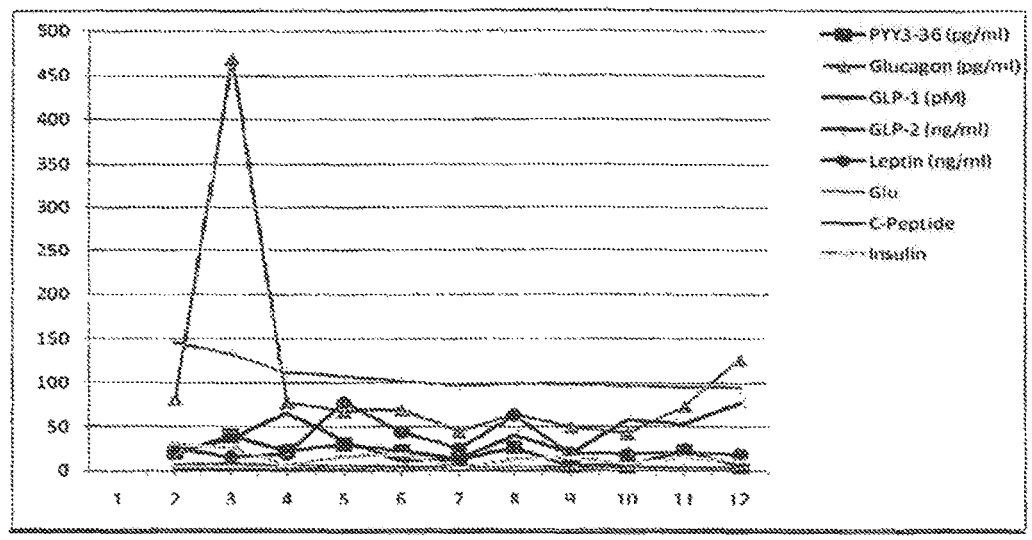
FIG. 23 is a chart showing the change in levels of various blood components during testing, with Table 16 showing the data, for the subject tested.
Figure 24:
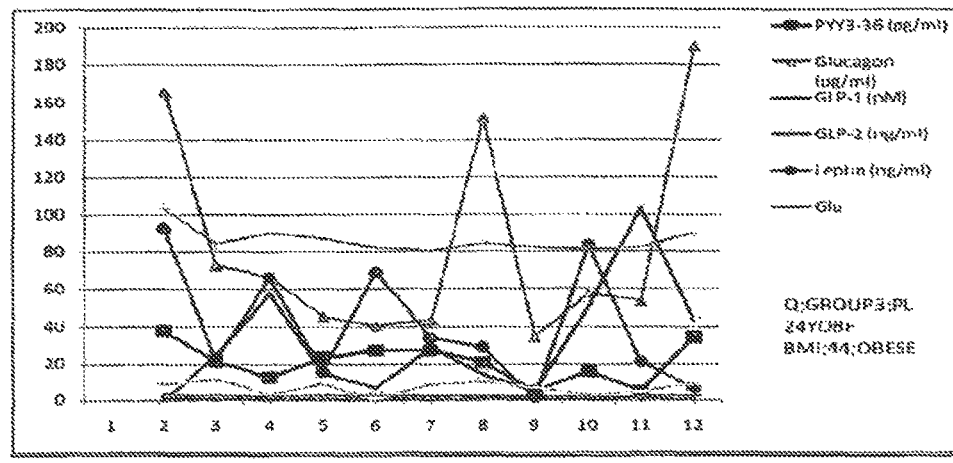
FIG. 24 is a chart showing the change in levels of various blood components during testing, with Table 1 showing the data, for the following subject: black female, 24 years old with a BMI of 44 (obese)
Figure 25:
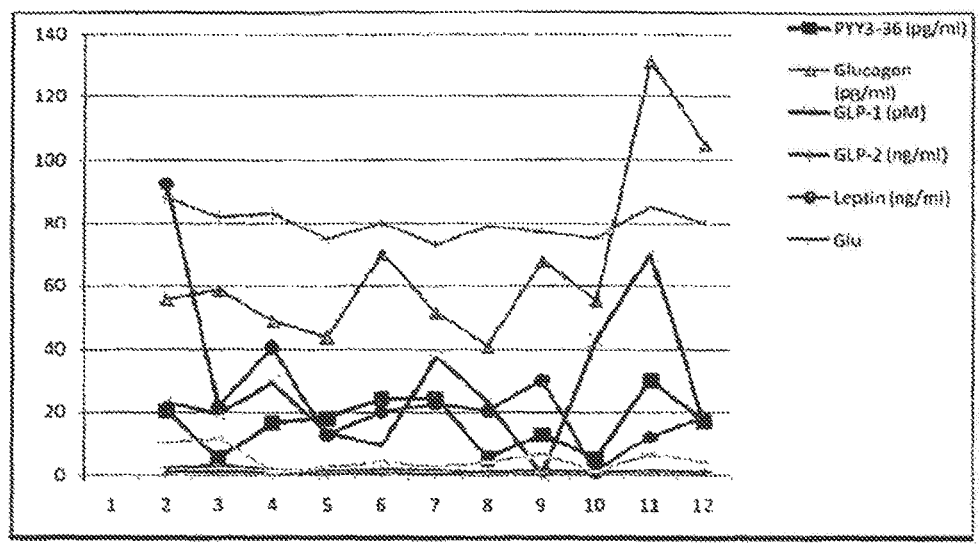
FIG. 25 is a chart showing the change in levels of various blood components during testing, with Table 18 showing the data, for the tested subject.
Figure 26:
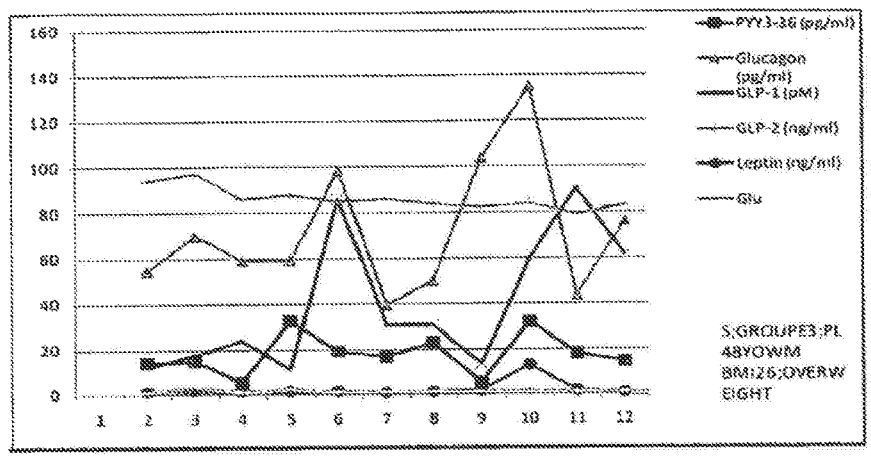
FIG. 26 is a chart showing the change in levels of various blood components during testing, with Table 19 showing the data, for the following subject: white male, 48 years old with a BMI of 26 (overweight)
Figure 27:
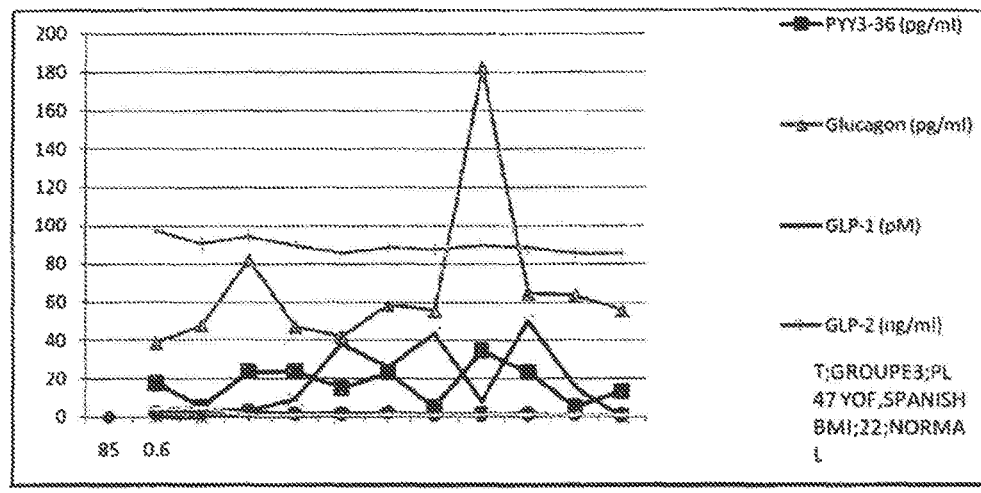
FIG. 27 is a chart showing the change in levels of various blood components during testing, with Table 20 showing the data, for the following subject: Hispanic female, 47 years old with a BMI of 22 (normal)
Figure 28:
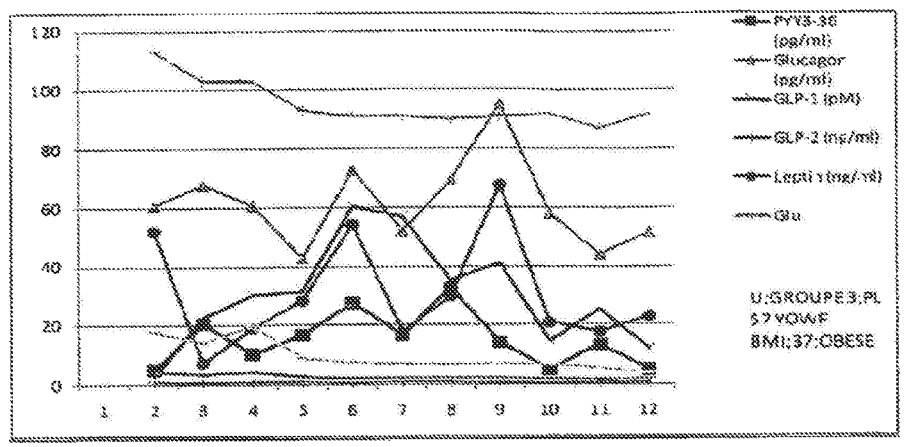
FIG. 28 is a chart showing the change in levels of various blood components during testing, with Table 21 showing the data, for the following subject: white female, 57 years old with a BMI of 37 (obese).
Figure 38:

FIG. 38 shows the total weight loss observed for a subject on Aphoeline 1 1 (50 year old female) as a function of days between measurements, and FIG. 11 shows levels of liver enzymes in the same patient at the times of measurements. For this subject, Aphoeline 1 1 clearly has a positive and significant effect on liver enzymes. Total weight loss for a 50 yowf with an initial blood sugar fasting of 220, ending with a blood sugar fasting of 110.

FIG. 39 shows the levels of liver enzymes for a steatohepatitis patient.

DETAILED DESCRIPTION OF THE INVENTION

The present invention approaches the problem of insulin resistance in a natural physiological manner by stimulating hormones in the lower gut, that is, the ileum which act synergistically to reduce insulin production, so as to promote a substantial equilibrium between the amount of insulin produced and the amount of blood sugar. It does this using natural nutritional components in healthful, pleasant compositions which are preferably coated using a polymeric, preferably nutrateric coating to release effective nutritional substances within the ileum of a patient or subject and effect a natural physiological response within the subject's ileum with favorable results. The present invention represents a change in the nature of treating an insulin imbalance in a subject, using a more wholesome, natural physiological process, completely distinguishable over pharmaceutical or synthetic approaches. The present invention may also be used treat noninsulin dependent diabetes mellitus, pre-diabetes syndrome, metabolic syndrome, glucose intolerance and insulin resistance as well as a number of gastrointestinal tract disorders or conditions as otherwise described herein. The following definitions are used to describe the present invention and apply unless otherwise indicated.

The term "patient" or "subject" is used throughout the specification within context to describe an animal, generally a mammal and preferably a human, to whom treatment, including prophylactic treatment, with the compositions and/or methods according to the present invention is provided. For treatment of a particular condition or disease state which is specific for a specific animal such as a human patient, the term patient refers to that specific animal.

The term "effective" is used herein, unless otherwise indicated, to describe an amount of a compound, composition or component and for an appropriate period of time which, in context, is used to produce or effect an intended result, whether that result relates to the treatment of a disorder or condition associated with the present invention or alternatively, is used to produce another compound, agent or composition. This term subsumes all other effective amount or effective concentration terms which are otherwise described in the present application. In many instances, with the administration of D-glucose (dextrose) as a nutritional substance in compositions and methods according to the present invention, an effective amount of D-glucose ranges from about 500 mg. to about 12.5 grams or more, preferably about 10 grams used on a daily basis.

The term "nutritional substance" refers to the substance which produces the intended effect in the ileum of a patient or subject pursuant to the present invention.

A "nutritional substance" includes, but is not limited to, proteins and associated amino acids, fats including saturated fats, monosaturated fats, polyunsaturated fats, essential fatty acids, Omega-3 and Omega-6 fatty acids, trans fatty acids, cholesterol, fat substitutes, carbohydrates such as dietary fiber (both soluble and insoluble fiber), starch, sugars (including monosaccharidesmonosaccharide, fructose, galactose, glucose, disacharidesdisaccharides, lactose, maltose, sucrose, and alcohol), polymeric sugars including inulin and polydextrose, natural sugar substitutes (including brazzein. Curculin, erythritol, fructose, glycyrrhizin, glycyrrhizin, glycerol, hydrogenated starch hydrosylates, isomalt, lactitol, mabinlin, maltitol, mannitol, miraculin, monellin, pentadin, sorbitol, stevia, tagatose, thaumatin, and xylitol), sahlep, and halwa root extract. D-glucose (dextrose) is a preferred nutritional substance. Nutritional substances include all compositions that yield the aforementioned nutrients upon digestion or that contain such nutrients, including polymeric forms of these nutrients.

Additional nutritional components which may be included in compositions according to the present invention include, barley grass, known to be a rich source of highly metabolizable vitamins and minerals such as vitamins A, B1, B2, B6, and C, potassium, magnesium, and zinc. In addition, barley grass also has a high concentration of the enzyme superoxide dismutase (SOD), which has been shown to have high levels of antioxidant activity. Barley grass is believed to be an important nutrient in the regulation of the digestive process because the micronutrients, enzymes (e.g., SOD), and fiber contained in barley grass are believed to improve intestinal function.

Alfalfa fresh or dried leaf tea is also usable in the invention, to promote appetite, and as a good source of chlorophyll and fiber. Alfalfa contains biotin, calcium, choline, inositol, iron, magnesium, PABA, phosphorus, potassium, protein, sodium, sulfur, tryptophan (amino acid), and vitamins A, B complex, C, D, E, K, P, and U. Alfalfa supplements are recommended for treating poor digestion, and were shown to lower cholesterol levels in animal studies. Alfalfa is categorized as Generally Regarded as Safe (GRAS) by the FDA. Dosages can range from 25-1500 mg, preferably 500-1000 mg dried leaf per day.

Chlorella is yet another substance usable in the invention in combination with the nutritional substance (preferably D-glucose or dextrose), being a genus of unicellular green algae, grown and harvested in tanks, purified, processed and dried to form a powder. Chlorella is rich in chlorophyll, carotenes, and contains the full vitamin B complex, vitamins E and C, and has a wide range of minerals, including magnesium, potassium, iron and calcium. Chlorella also provides dietary fiber, nucleic acids, amino acids, enzymes, CGF (Chlorella Growth Factor) and other substances. Dosages can range from 300-1500 mg/day.

Chlorophyllin is yet another nutritional substance, being a known food additive and has been used as an alternative medicine. Chlorophyllin is a water-soluble, semi-synthetic sodium/copper derivative of chlorophyll, and the active ingredient in a number of internally-taken preparations intended to reduce odors associated with incontinence, colostomies and similar procedures, as well as body odor in general. It is also available as a topical preparation, purportedly useful for treatment and odor control of wounds, injuries, and other skin conditions, such as for radiation burns.

Sodium alginate may also be used as a nutritional substance, preferably in combination with D-glucose or dextrose.

The term "ileum" is used to describe the third (of three) portion of the small intestine just before the small intestine becomes the large intestine in the gastrointestinal tract. The ileum is the final section of the small intestine in most higher vertebrates, including mammals. The ileum follows the duodenum and jejunum in the small intestine, and is separated from the "Cecum" by the ileocecal valve (ICV). In humans, the ileum is about 2-4 meters long, and the pH usually ranges between 7 and 8 (neutral or slightly alkaline). The function of the ileum is mainly to absorb vitamin B12 bile salts and whatever products of digestion were not absorbed by the jejunum. The wall itself is made up of folds, each of which has many tiny finger-like projections known as "villi" on its surface. In turn, the epithelial cells which line these villi possess even larger numbers of microvilli. Therefore, the ileum has an extremely large surface area both for the adsorption of enzyme molecules and for the absorption of products of digestion. The DNES (diffuse neuroendocrine system) cells that line the ileum contain less amounts of the protease and carbohydrase enzymes (gastrin, secretin, cholecystokinin) responsible for the final stages of protein and carbohydrate digestion. These enzymes are present in the cytoplasm of the epithelial cells.

The term "Delays the release in vivo of the majority of the nutritional substance until the dosage form reaches the subject's ileum" means: (1) that not less than around 50% by weight, not less than around 70% by weight, more preferably not less than around 80% by weight, and more preferably not less than around 90%, of the nutritional substance remains unreleased in vivo prior to the dosage form's arrival at a subject's ileum; and (2) that not less than around 50%, not less than around 70% by weight, more preferably not less than around 80% by weight, and more preferably not less than around 90%, of the nutritional substance is remains unreleased in vivo by the time when the dosage form enters the subject's ileum. In preferred aspects of the invention this amount is at least about 1 gram, at least about 2.5 grams, at least about 3 grams, at least about 5 grams, at least about 7.5 grams, preferably about 10 grams to about 12-12.5 grams or more (about 12.5 to about 20 grams, especially of polymeric materials such as polydextrose or those compounds of higher molecular weight) of the nutritional substance and in particular, glucose, is released within the small intestine in the ileum in order to stimulate ileum hormones and related hormones and effect the intended result associated with inducing satiety and/or influencing one or more of insulin resistance (decrease resistance), blood sugar (decrease in/stabilize glucose levels), leptin (increase), glucagon secretion (decrease), insulin release (decrease and/or stabilize release and/or levels), ileum hormone release (increase) or other hormone release, in particular, one or more of GLP-1, glicentin, C-terminally glycine-extended GLP-1 (7 37), (PG (78 108)); C-peptide, intervening peptide-2 (PG (111 122) amide); GLP-2 (PG (126 158), GRPP (PG (1 30)), oxyntomodulin (PG (33 69), and other peptide fractions to be isolated, PYY (1-36), PYY (3-36), cholecystokinin (CCK), gastrin, enteroglucagon, secretin, as well as leptin, IGF-1 and IGF-2, and preferably, one or more, two or more, three or more, four or more, five or more, six or more, seven or more, or all of GLP1, GLP2, C-peptide, PYY (1-36 and/or 3-36), glucagon, leptin, IGF-1 and IGF-2.

The term "ileum hormones" includes all hormones that are associated with intraluminal food substances stimulating the release of said hormones, could be associated with satiety feedback from the ileum or ileum-related stimulation of insulin secretion or inhibition of glucagon secretion. "Ileum hormones" therefore include, but are not limited to, GLP-1, glicentin, C-terminally glycine-extended GLP-1 (7 37), (PG (78 108)); intervening peptide-2 (PG (111 122) amide); GLP-2 (PG (126 158), GRPP (PG (1 30)), oxyntomodulin (PG (33 69), and other peptide fractions to be isolated, PYY (PYY 1-36) and (PYY 3-36), cholecystokinin (CCK), gastrin, enteroglucagon and secretin.

The term "ileum hormone-stimulating amount of a nutritional substance" means any amount of a nutritional substance that is effective to induce measurable hormone release in the ileum, and induce satiety feedback from the ileum or ileum-related stimulation of insulin secretion or inhibition of glucagon secretion, or other effect such as shutting down or decreasing insulin resistance and increasing glucose tolerance. Consequently, an "ileum hormone-stimulating amount of a nutritional substance" can vary widely in dosage depending upon factors such as the specific nutrient at issue, the desired effect of administration, the desired goal of minimizing caloric intake, and the characteristics of the subject to whom the nutritional substance is administered. For example, at least about 500 mg of D-glucose is used, and a particularly preferred ileum hormonal-stimulating amount of D-glucose includes between about 7.5-8 g to about 12-12.5 g (preferably around 10 g).

The term "gastrointestinal disorder" includes diarrheal states, malabsorption in the lower gut (i.e., chronic pancreatitis, celiac disease), fatty liver, atrophic gastritis, short bowel syndrome, radiation enteritis, irritable bowel disease, Chron's disease, post infectious syndrome, mild reflux, certain gut dismotility, post chemotherapy disorder, malnutrition, malabsorption, and voluntary or involuntary long term starvation. The present invention may be used to treat each of these conditions, alone or secondary to the treatment or resolution of symptoms associated with noninsulin dependent diabetes mellitus, pre-diabetic symptoms, metabolic syndrome and insulin resistance.

Dosage forms used in methods of the invention can be in a form suitable for oral use, for example, as tablets, troches, lozenges, suspensions, microsuspensionsmicro suspensions, dispersible powders or granules, emulsions, microemulsionsmicro emulsions, hard or soft capsules. Useful dosage forms include osmotic delivery systems as described in U.S. Pat. Nos. 4,256,108; 5,650,170 and 5,681,584, multiparticulate systems as disclosed in U.S. Pat. No. 4,193,985; systems in which the nutritional substance is coated with a mixed film of a hydrophobic organic compound-enteric polymer as disclosed in U.S. Pat. No. 6,638,534; systems such as those described in U.S. Pat. Nos. 7,081,239; 5,900,252; 5,603, 953; and 5,573,779; enteric-coated dry emulsion formulations (e.g., *Journal of Controlled Release*, vol. 107, issue 1 20 Sep. 2005, Pages 91-96), and emulsions such as the emulsion system of Olibra® and those disclosed in U.S. Pat. No. 5,885,590. Those of ordinary skill in the prior art know how to formulate these various dosage forms such that they release the majority of their nutritional substance in a subject's ileum as otherwise described herein.

Exemplary dosage forms that will release the majority of the nutritional substance in vivo upon reaching the ileum include oral dosage forms such as tablets, troches, lozenges, dispersible powders or granules, or a hard or soft capsules which are formed by coating the nutritional substance with an enteric coating (e.g., an enteric cellulose derivative, an enteric acrylic copolymer, an enteric maleic copolymer, an enteric polyvinyl derivative, or shellac). Preferred enteric coatings have a pH dissolution profile that delays the release in vivo of the majority of the nutritional substance until the dosage form reaches the ileum. Enteric coatings can consist of a single composition, or can comprise two or more compositions, e.g., two or more polymers or hydrophobic organic compound-enteric polymer compositions as described in U.S. Pat. No. 6,638,534).

A "material having a pH dissolution profile that delays release in vivo of the majority of the nutritional substance until the dosage form reaches the ileum" includes but is not limited to cellulose acetate trimellitiate (CAT), hydroxypropylmethyl cellulose phthalate (HPMCP), polyvinyl acetate phthalate (PVAP), cellulose acetate phthalate (CAP), shellac, copolymers of methacrylic acid and ethyl acrylate, copolymers of methacrylic acid and ethyl acrylate to which a monomer of methylacrylate has been added during polymerization, a mixture of amylose-butan-1-ol complex (glassy amylose) with Ethocel® aqueous dispersion (Milojevic et al., Proc. Int. Symp. Contr. Rel. Bioact. Mater. 20, 288, 1993), a coating formulation comprising an inner coating of glassy amylose and an outer coating of cellulose or acrylic polymer material (Allwood et al. GB 9025373.3), calcium pectinate (Rubenstein et al., Pharm. Res., 10, 258, 1993) pectin, chondroitin sulphate (Rubenstein et al. Pharm. Res. 9, 276, 1992), resistant starches (PCT WO 89/11269), dextran hydrogelshydro gels (Hovgaard, et al., 3rd Eur. Symp. Control. Drug Del., Abstract Book, 1994, 87) modified guar gum such as borax modified guar gum, (Rubenstein and Gliko-Kabir, S. T. P. Pharma Sciences 5, 41-46, 1995), beta.-cyclodextrin (Sidke et al., Eu. J. Pharm. Biopharm. 40 (suppl), 335, 1994), saccharide containing polymers, e.g., a polymeric construct comprising a synthetic oligosaccharide-containing biopolymer including methacrylic polymers covalently coupled to oligosaccharides such as cellobiose, lactulose, raffinose and stachyose, or saccharide-containing, natural polymers including modified mucopolysaccharides such as cross-linked pectate (Sintov and Rubenstein PCT/US 91/03014); methacrylate-galactomannan (Lehmann and Dreher, Proc. Int. Symp. Control. Rel. Bioact. Mater. 18, 331, 1991) and pH-sensitive hydrogels (Kopecek et al., J. Control. Rel. 19, 121, 1992), and resistant starches, e.g., glassy amylose.

Methylmethacrylates or copolymers of methacrylic acid and methylmethacrylate are preferred materials having a pH dissolution profile that delays release in vivo of the majority of the nutritional substance until the dosage form reaches the ileum. Such materials are available as Eudragit® polymers (Rohm Pharma, Darmstadt, Germany). For example, Eudragit® L100 and Eudragit® S100 can be used, either alone or in combination. Eudragit® L100 dissolves at pH 6 and upwards and comprises 48.3% methacrylic acid units per g dry substance; Eudragit® S100 dissolves at pH 7 and upwards and comprises 29.2% methacrylic acid units per g dry substance. Generally, the encapsulating polymer has a polymeric backbone and acid or other solubilizing functional groups. Polymers which have been found suitable for purposes of the present invention include polyacrylates, cyclic acrylate polymer, polyacrylic acids and polyacrylamides. Another preferred group of encapsulating polymers are the polyacrylic acids Eudragit® L and Eudragit® S which optionally may be combined with Eudragit® RL or RS. These modified acrylic acids are useful since they can be made soluble at a pH of 6 or 7.5, depending on the particular Eudragit chosen, and on the proportion of Eudragit® S to Eudragit® L, RS, and RL used in the formulation. By combining one or both of Eudragit® L and Eudragit® S with Eudragit® RL and RS (5-25%), it is possible to obtain a stronger capsule wall and still retain the capsule's pH-dependent solubility. In additional preferred aspects of the invention, a coating of shellac (which also includes one or more emulsifiers such as hypromellose and/or triacetin) which is chosen to have a suitable pH-dependent dissolution profile for release the contents of a dosage form such as a tablet within the ileum of a patient or subject may be used. This type of coating provides a nutrateric approach to delayed and/or controlled release using naturally occurring, non-synthetic components.

A delayed and/or controlled release oral dosage form used in the invention can comprise a core containing an ileum hormonal-stimulating amount of a nutritional substance that is coated by an enteric coating. In some embodiments, the coating comprises Eudragit® L100 and shallac, or food glaze Eudragit® S100 in the range of 100 parts L100:0 parts S100 to 20 parts L100:80 parts S100, more preferably 70 parts L100:30 parts S100 to 80 parts L100:20 parts S100. As the pH at which the coating begins to dissolve increases, the thickness necessary to achieve ileum-specific delivery decreases. For formulations where the ratio of Eudragit® L100:S100 is high, a coat thickness of the order 150-200 µm can be used. For coatings where the ratio Eudragit® L100:S100 is low, a coat thickness of the order 80-120 µm can be used. Dosage forms used in methods of the invention can include one or more pharmaceutically acceptable carriers, additives, or excipients. The term "pharmaceutically acceptable" refers to a carrier, additive or excipient which is not unacceptably toxic to the subject to which it is administered. Pharmaceutically acceptable excipients are described at length by E. W. Martin, in "Remington's Pharmaceutical Sciences", among others well-known in the art. pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Emulsions and microemulsions may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the nutritional substance, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Techniques for formulating the aforementioned useful dosage forms are either disclosed in the references cited above or are well-known to those of ordinary skill in the art. is a particularly preferred dosage form that is useful in the methods of treatment of the invention.

The term "satiety" encompasses a lack of appetite for food or a cessation of food-seeking or food-ingesting behavior. Thus, satiety is a desirable state in conditions in which food intake is preferably curtailed, such as obesity. Alternatively, it can be desirable to suppress a state of satiety in conditions of anorexia or cachexia resulting from causes including illness, starvation, or chemotherapy.

"Stabilizing a subject's blood sugar and insulin levels" means lowering the subject's blood sugar and insulin levels to healthy levels within normal or close to normal ranges.

The terms "obesity" and "overweight" are generally defined by body mass index (BMI), which is correlated with total body fat and estimates the relative risk of disease. BMI is calculated by weight in kilograms divided by height in meters squared (kg/m2). Normal BMI is defined as a BMI of about 18.5 to 24.9 kg/m2. Overweight is typically defined as a BMI of 25-29.9 kg/m2, and obesity is typically defined as a BMI of at least 30 kg/m2. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998). Obesity and its associated disorders are common and very serious public health problems in the United States and throughout the world. Upper body obesity is the strongest risk factor known for type 2 diabetes mellitus and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia. Obesity reduces life-span and carries a serious risk of the co-morbidities listed above, as well as disorders such as infections, varicose veins, acanthosis nigricans, eczema, exercise intolerance, insulin resistance, hypertension hypercholesterolemia, cholelithiasis, orthopedic injury, and thromboembolic disease (Rissanen et al., Br. Med. J. 301: 835-7 (1990)). Obesity is also a risk factor for the group of conditions called insulin resistance syndrome, or "Syndrome X" and metabolic syndrome. The present compositions are useful for treating obesity, and favorably impact the conditions which often occur secondary to obesity.

"Obesity-related disorder" includes all of the diseases and disorders mentioned in the preceding definition of "obesity".

"Once-daily administration to the subject of a delayed and/or controlled release dosage form" includes self-administration of the dosage form by the subject.

The invention is described further in the following examples, which are illustrative and are not limiting.

Example 1

Healthy Human Volunteer Study
Formulation 1 for Further Studies
  600 mg/capsule glucose
  100 mg capsule
  10% Eudragit coating
  Plasticizer (propylene glycol, triethyl acetate and water)
  Magnesium stearate
  Silicone Dioxide A single formulation as described for formation 1 above was administered to five healthy adult human volunteers fasting in the morning at bedtime. Each of the volunteers was in the fasted state (i.e., none had eaten within two hours of the formulation administration). Blood levels (ng/ml) of GLP-1, GLP-2, C-peptide, GLP-1 (total) (determined by radioimmunoassay (ria)), PYY, blood sugar (bs), GLP-1 (total) (with plasma), and insulin for each of the volunteers were measured just prior to administration of the above formulation and every four hours after administration until the eleventh hour after administration of the formulation.

Based on the data obtained for the five individuals tested as above, it was concluded that for all subjects except for one, that blood levels of GLP-1 (total) (ria), GLP-1 (total) (with plasma), GLP-2, PYY, insulin, C-peptide, and blood sugar peaked at around 6-10 hours after administration of formulation 1. The peak levels of GLP-1 (total) (riaRIA), GLP-1 (total) (with plasma), GLP-2, and PYY correlated with the peak levels of insulin, C-peptide, and blood sugar, especially for subjects D and E. This suggests that there is an inverted correlation between these two groups and therefore the stimulation of the first grouping causing a reduction of levels of the second grouping.

Further, blood sugar and insulin levels dropped as the result of the stimulation of GLP-1, GLP-2, C-peptide, PYY, and insulin.

After the experiment described in this example, some patients continued to take formulation 1 above for an extended period of time and experienced a satiety which ultimately led to weight loss and as well as in one patient significant control of blood sugar and insulin levels.

Levels of blood sugar ileal hormones and their response to food stimulation could be assessed and abnormalities in the response could be evaluated (GLP1, GLP2, PYY) as well as their levels and stimulation was (bs) and insulin proved relatively consistent for each of the five volunteers, which indicates that methods of the invention can be used to diagnose whether a subject suffers from a disorder associated with an abnormality in their ileal break hormones to respond to food, blood sugar or insulin levels. For example, a standard dosage form comprising an enterically-coated, ileum hormone-stimulating amount of a nutritional substance could be administered to a subject, the subject's levels of ileal hormones blood sugar and insulin as well as ileal hormones including GLP1, GLP2, PYY, and IGF-1, IGF-2 and leptin could be measured at regular intervals subsequent to administration of the nutritional substance, and measured levels of the ileal hormones (e.g, GLP1, GLP2, PYY, IGF-1, IGF-2, leptin), as well as blood sugar and insulin could be compared to healthy levels of ileal hormones, blood sugar and insulin determined by administering an equivalent enterically-coated, ileum hormone-stimulating amount of a nutritional substance to a control subject.

Further, this example and the following examples establish that compositions such as formulation 1 above, among others, when administered while the subject is in the fasted state and at a time of about 3 to 12 hours, preferably about six to about nine hours prior to the subject's next intended meal, provide an ileum hormone-stimulating amount of a nutritional substance that approximates the minimum natural caloric amount of the substance needed to induce satiety.

Example 2

Obese Subject Study

Figure 1:
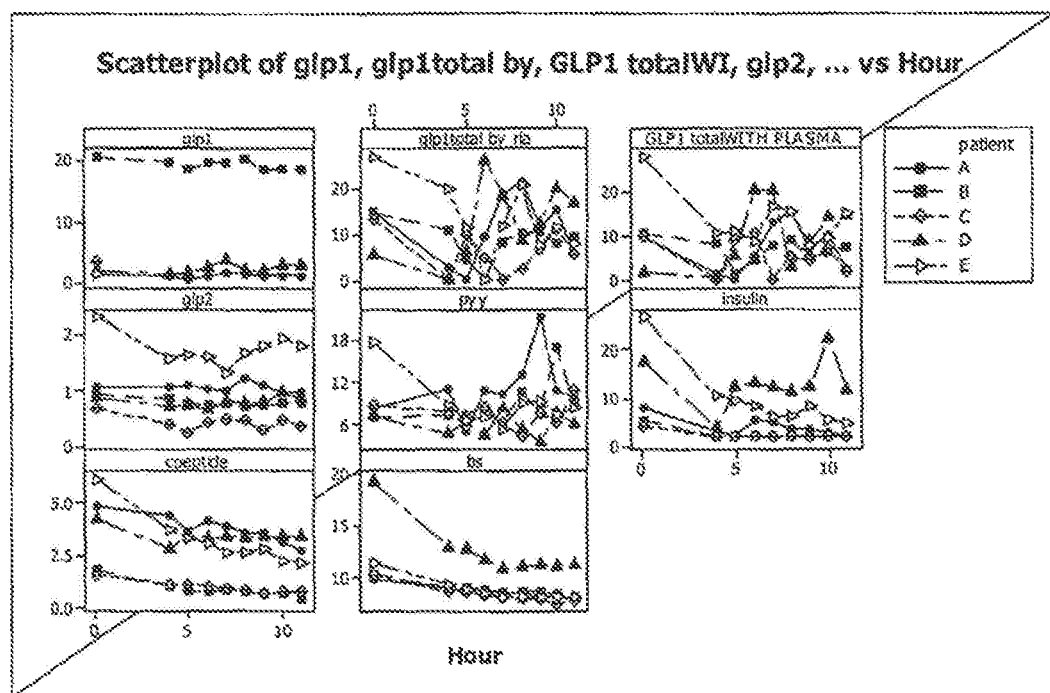
FIG. 1 is a scatter plot of blood levels (ng/ml) (CONFIRM UNITS) of GLP-1, GLP-2, C-peptide, GLP-1 (total) (determined by radioimmunoassay (riaRIA)), PYY, blood sugar (bsBS), GLP-1 (total) (with plasma), and insulin for five subjects tested in the experiment described in Example 1.
Figure 2:
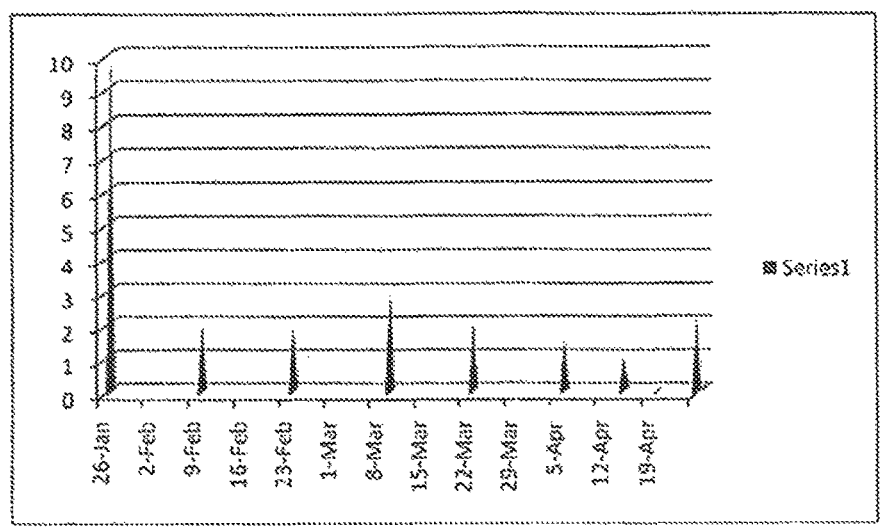
FIG. 2 illustrates four-month weight loss of the subject described in the experiment of example 2. Significant weight loss using the presently claimed compositions was evidenced. Further data (not presented) also evidenced consistent significant reduction/stabilization in glucose levels pursuant to the ingestion of a composition according to the present invention within about a 4 hour to 10 hour period.
Figure 5A:
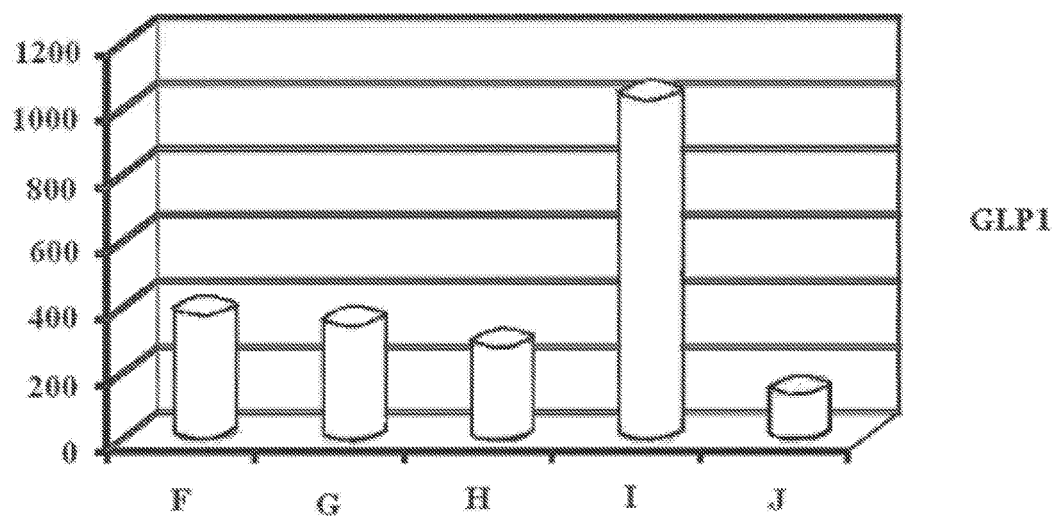
FIGS. 5A-J discloses twelve-hour values of blood levels above baseline of GLP-1 (pM), GLP-1 (with patient I as outlier and removed from graph), Glucose (blood sugar, mg/dl), C-peptide (ng/ml), Insulin (μIu/ml), GLP-1 (total) (ria), PYY (3-36, pg/ml), Leptin (ng/ml), Glucogon (pg/ml), IGF-I (ng/ml) and IGF-II (ng/ml) for subjects F, G, H, I and J tested in the experiment described in Example 3. The IGF and other parameters were measured to try to explain the decrease of insulin resistance seen as well as the simultaneous decrease in both the insulin and glucose showing a significant potential for treating diabetes as well as prediabetes and an increase in muscle mass and reduction in fat mass.
Figure 5B:
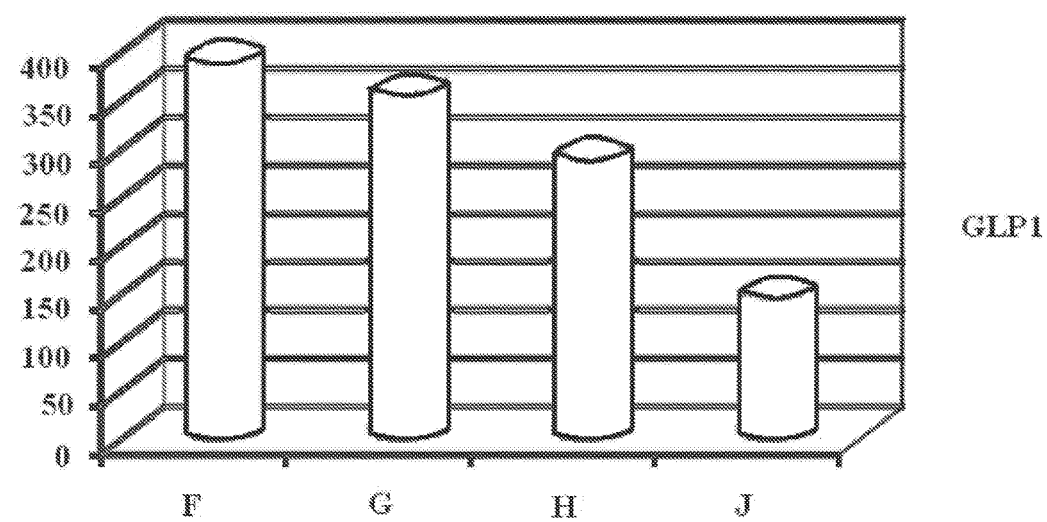
Figure 5C:
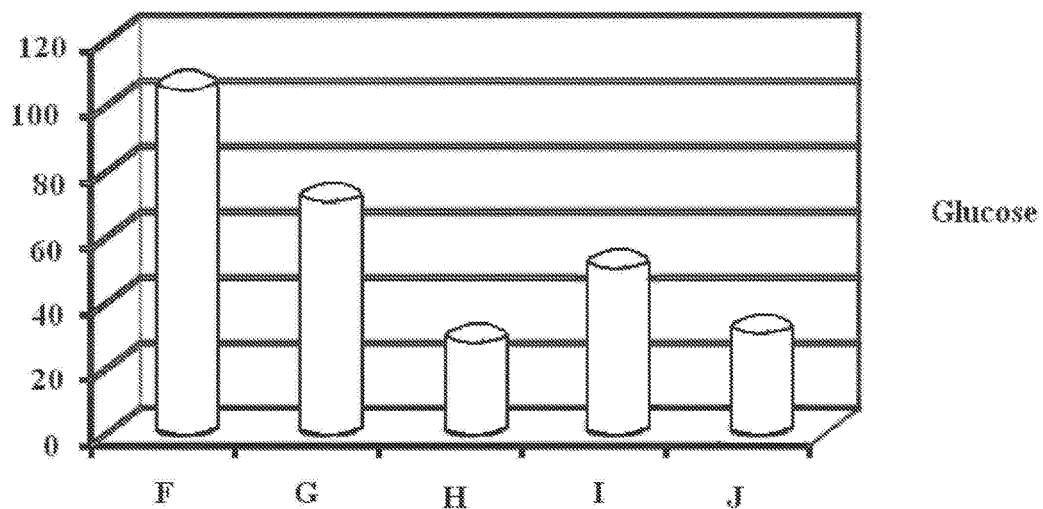
Figure 5D:
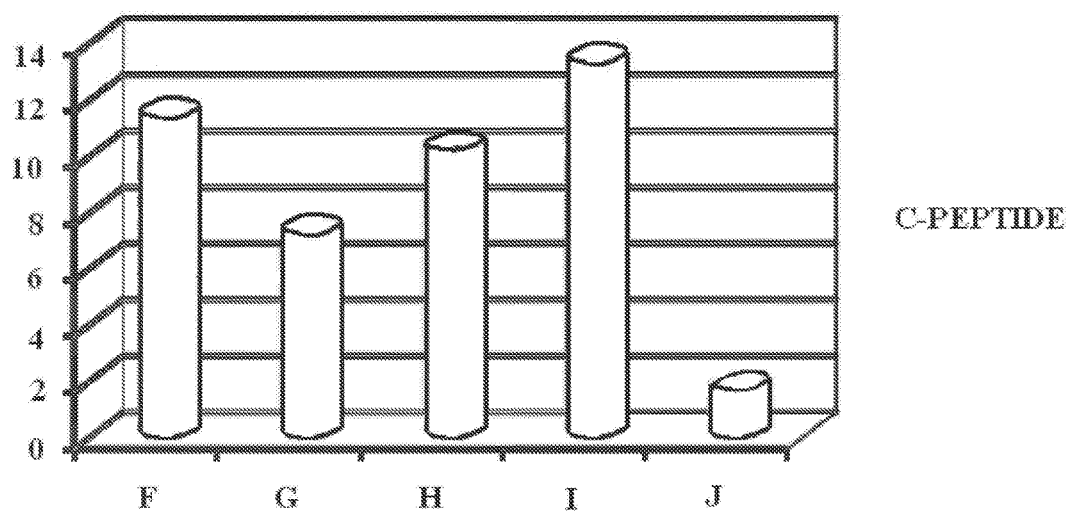
Figure 5E:
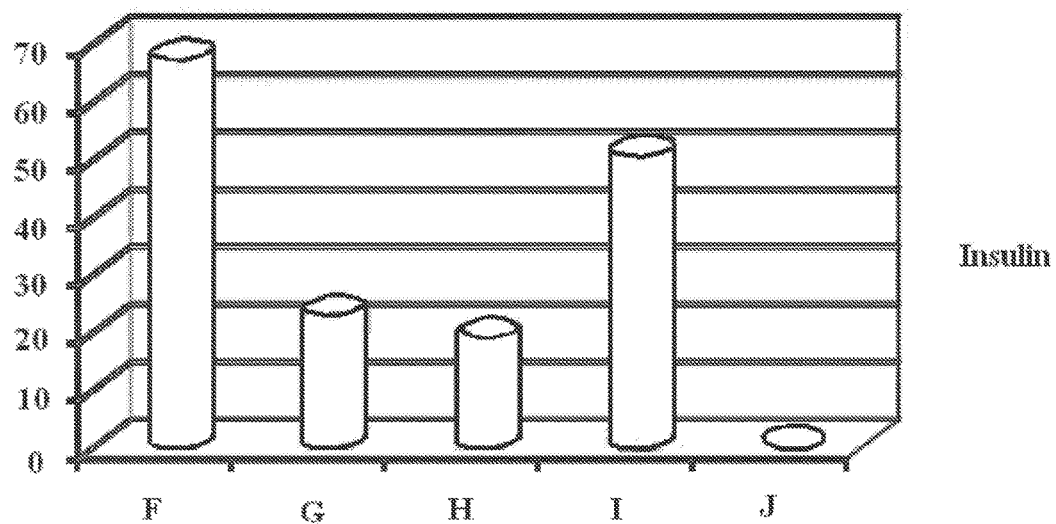
Figure 5F:
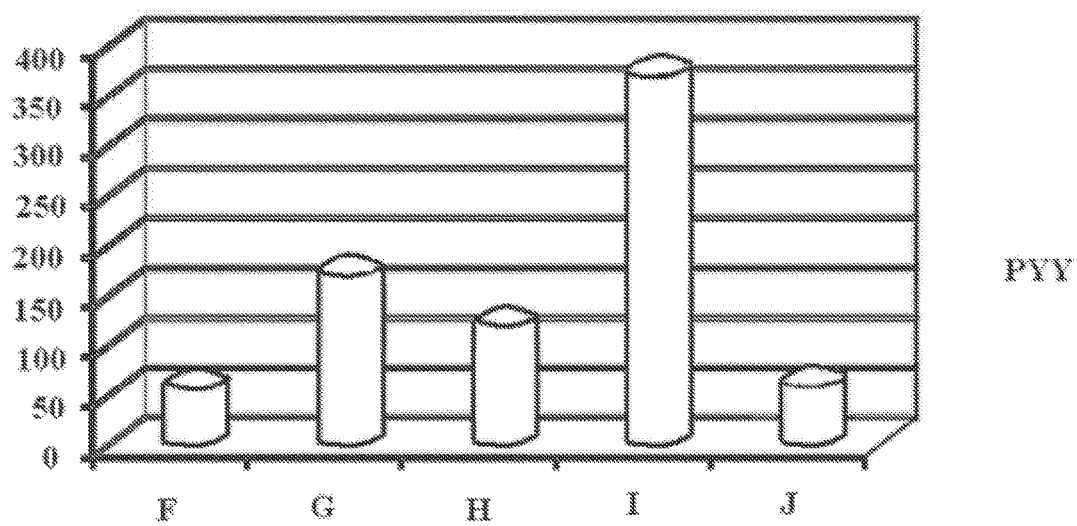
Figure 5G:
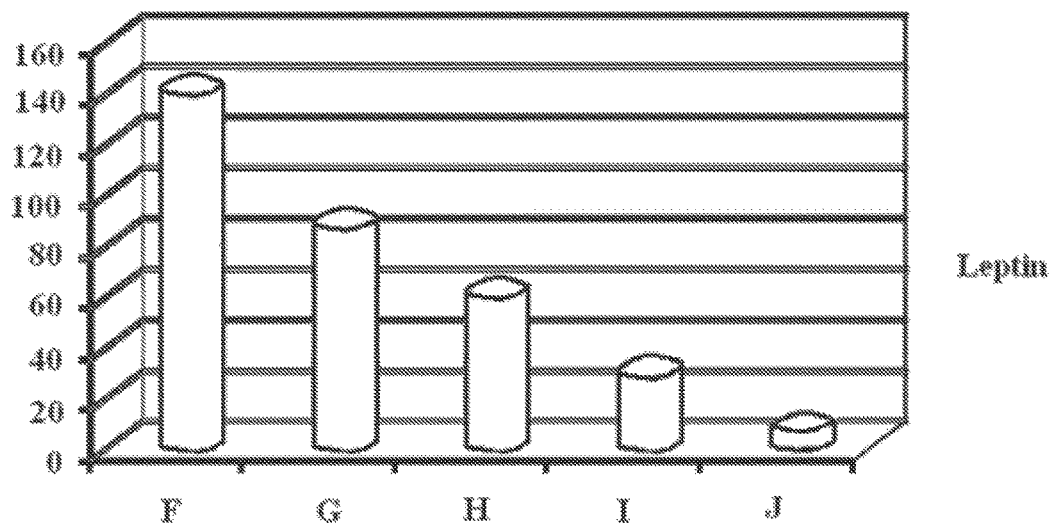
Figure 5H:
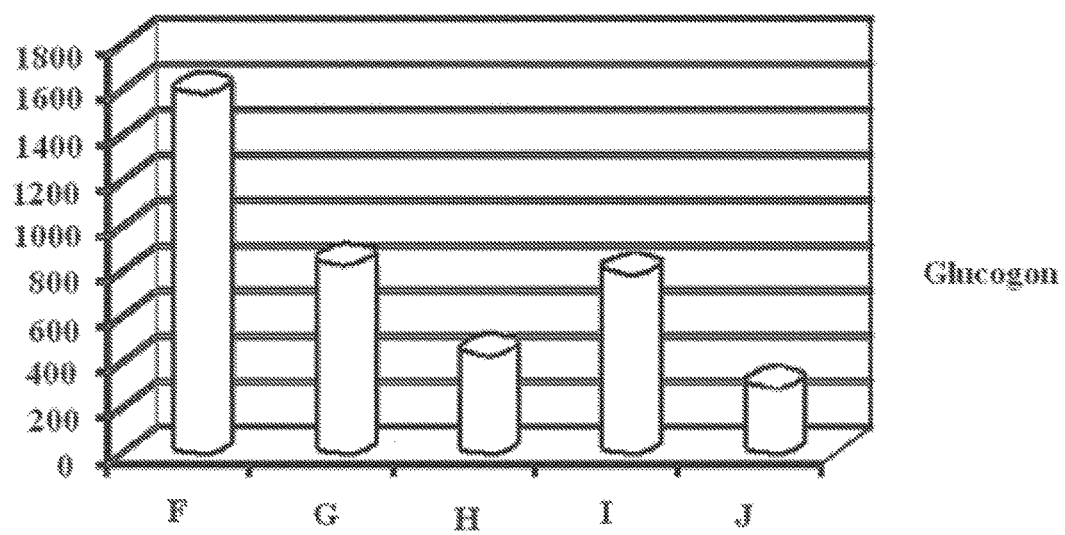
Figure 5I:
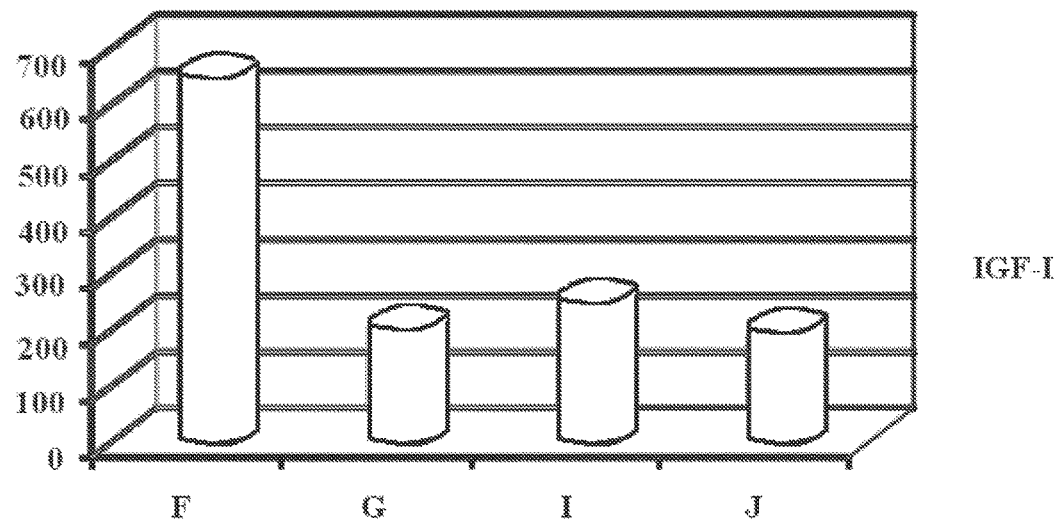
Figure 5J:
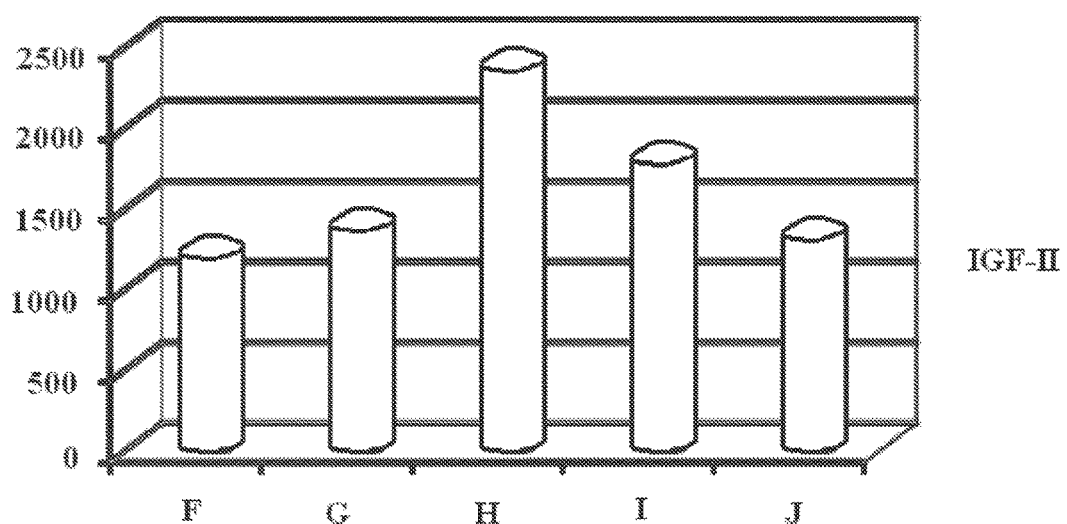
Figure 6:
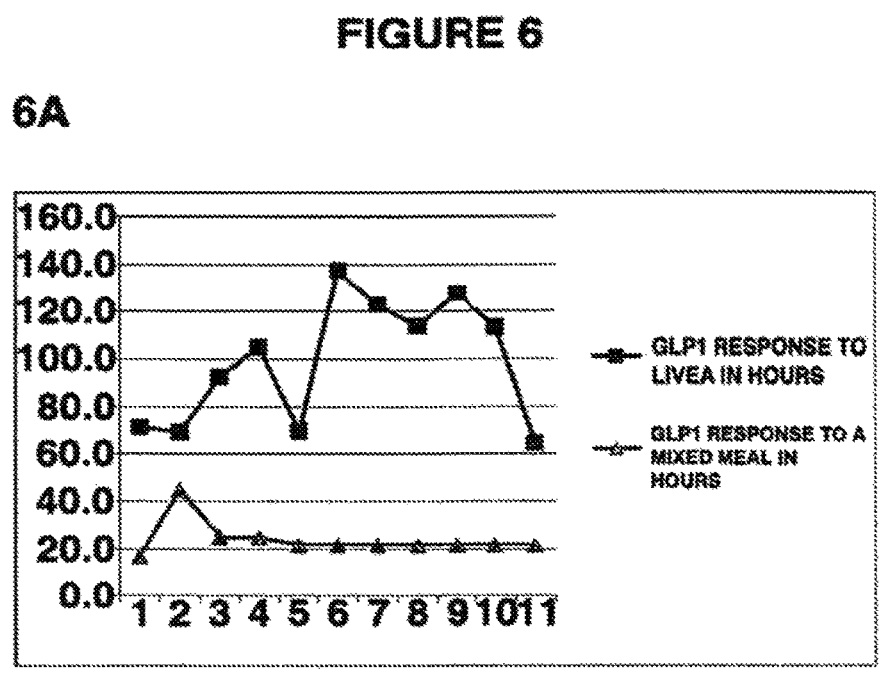
FIGS. 6A-F shows the results of GLP1 response to a formulation according to the present invention for five patients tested. The graphs presented represent the total GLP1 (pM) stimulation per hours comparing prior art levels in response to a mixed meal (triangles) and the results obtained from the use of the present invention in 5 patients. Note that the stimulation of the hormones by the present invention occurs between approximately hours 4 and 10 or more (after ingestion).
Figure 6:
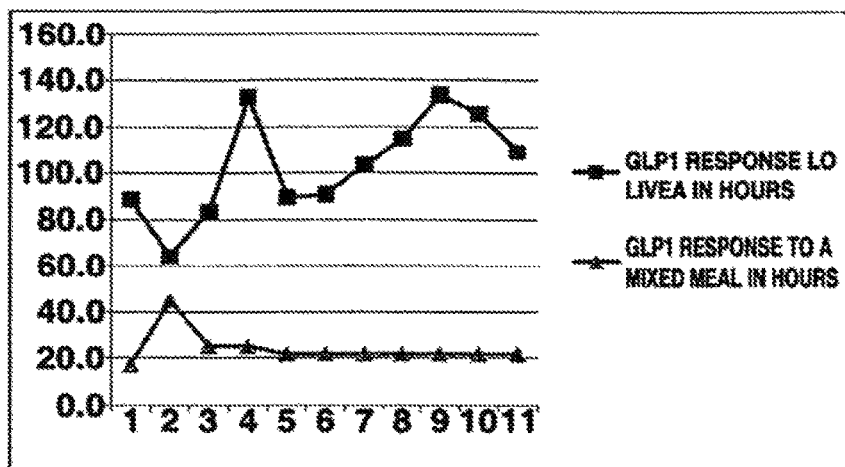
Figure 6:
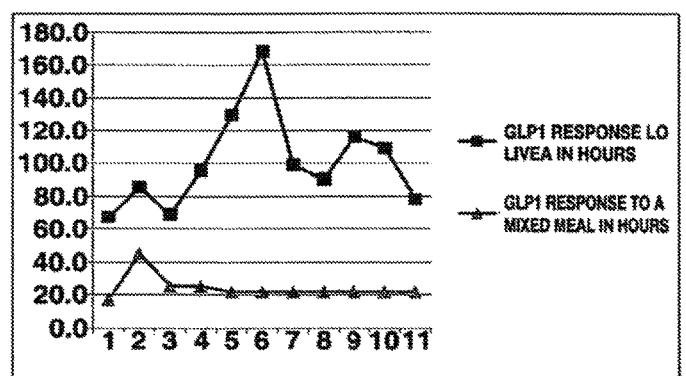
Figure 6:
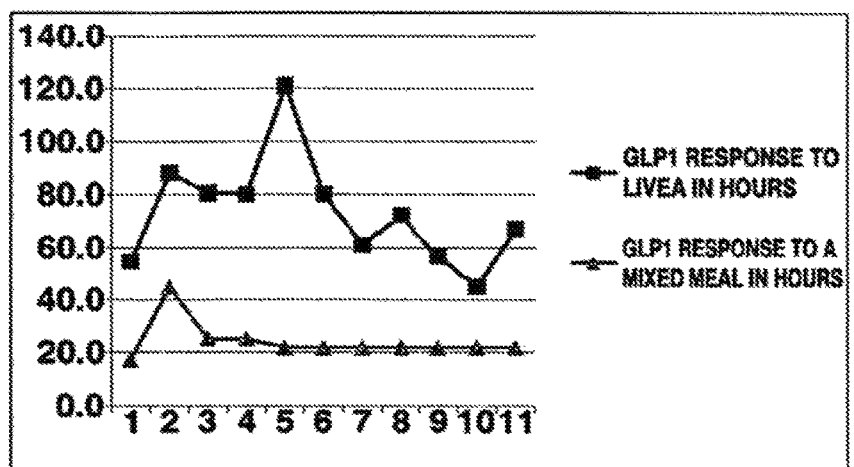
Figure 6:
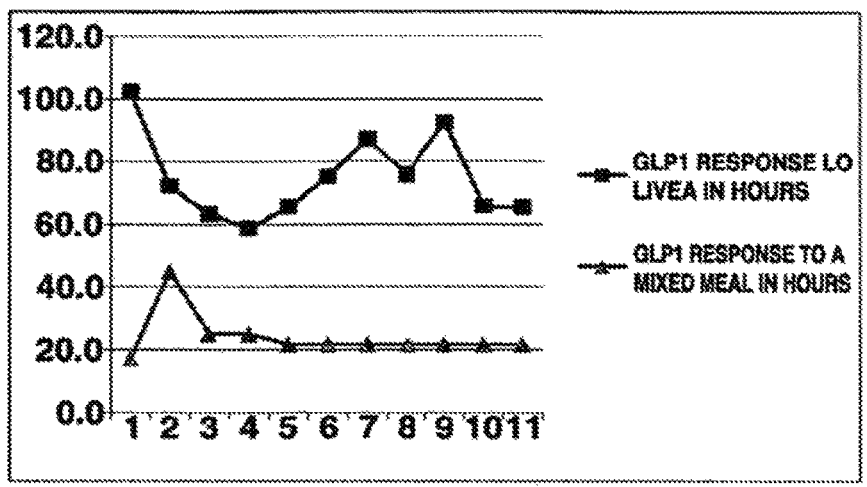
Figure 6:
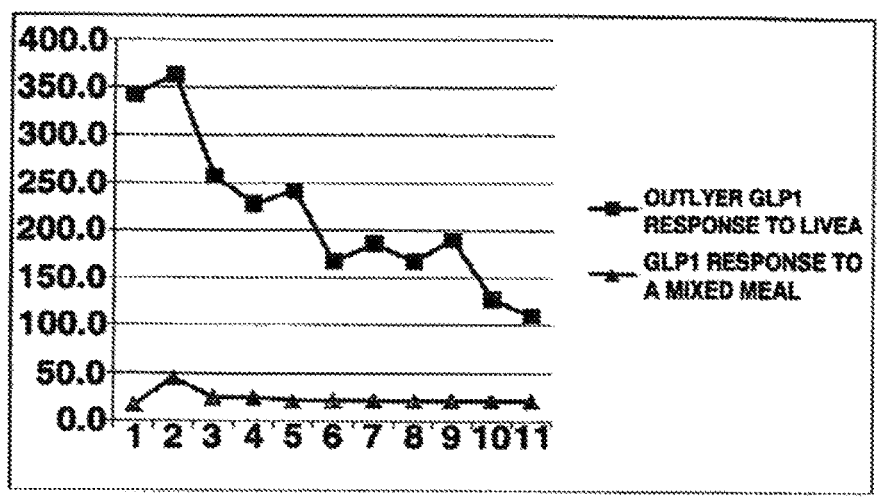
Figure 7:
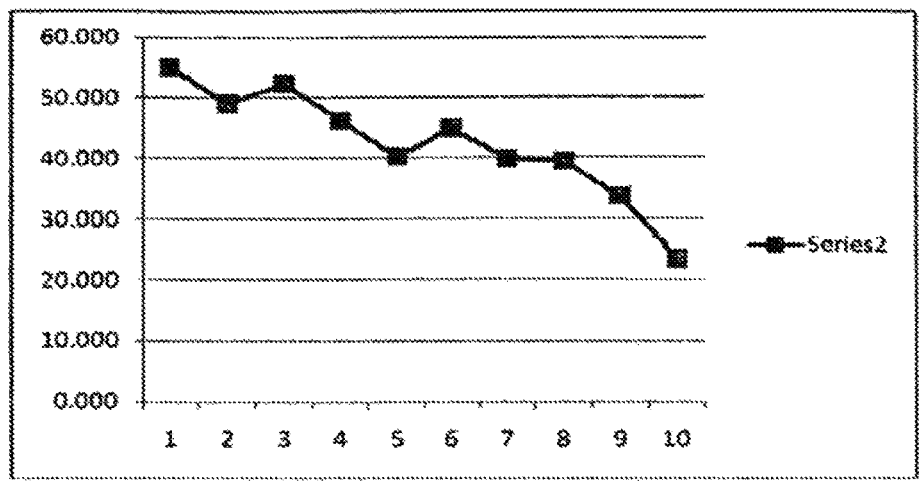
FIGS. 7A-E shows the results of PYY response in individuals following the ingestion of a formulation according to the present invention. As can be seen from the results presented in these figures, PYY stimulation (pg/ml) is the same pattern as other hormones of the ileal break with a maximum intensity between about 4 to 10 hours, even though the cephalic phase is more prominent than is GLP1 (pM). The overall stimulus is consistent with the stimulation by the formulation of the present invention.
Figure 7:
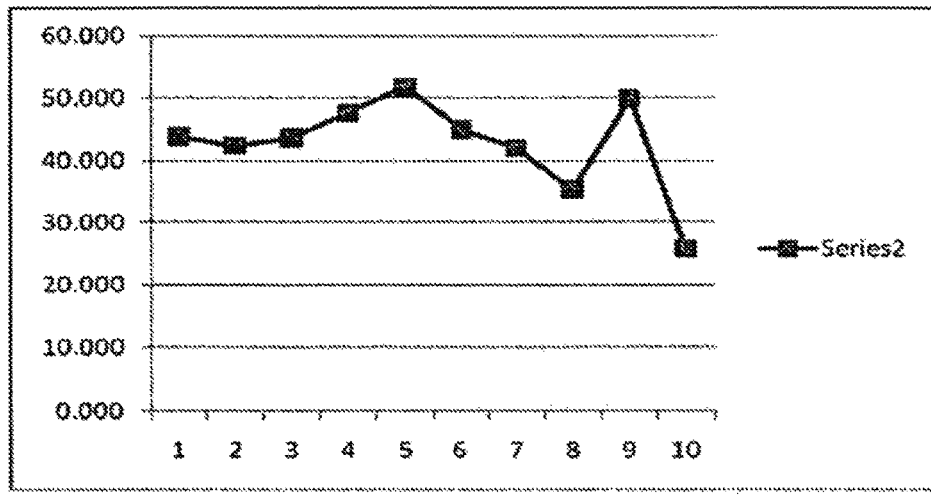
Figure 7:
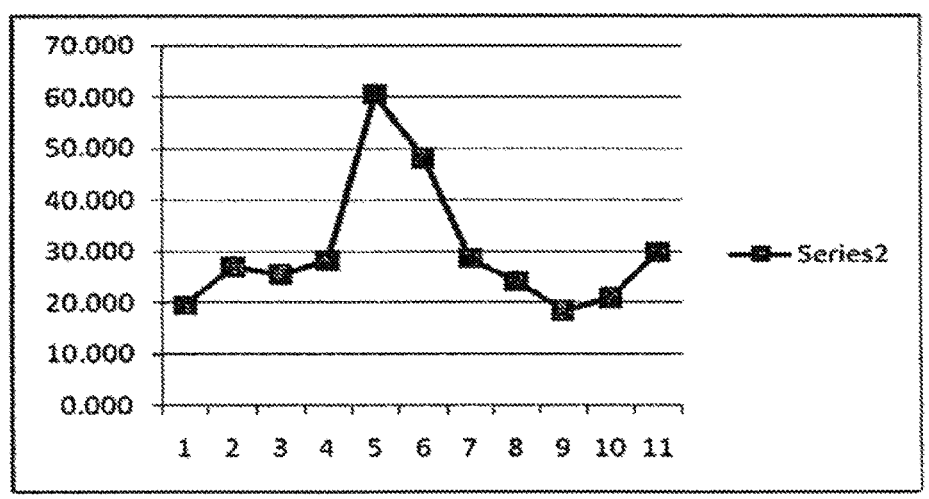
Figure 7:
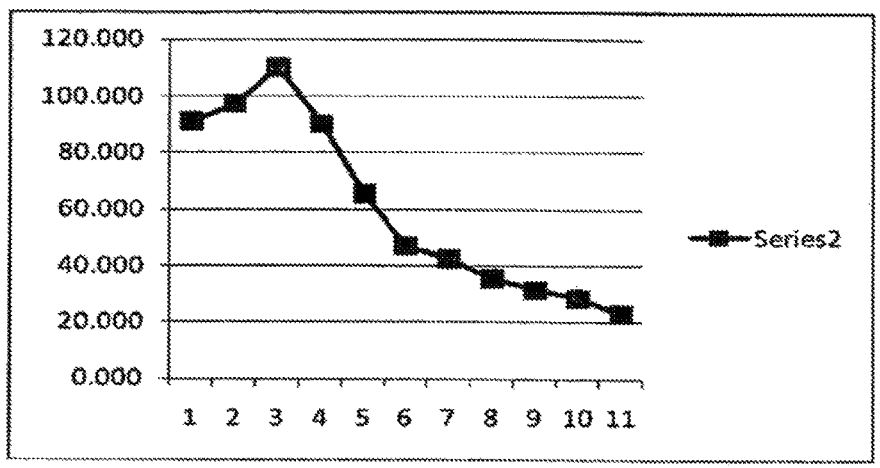
Figure 7:
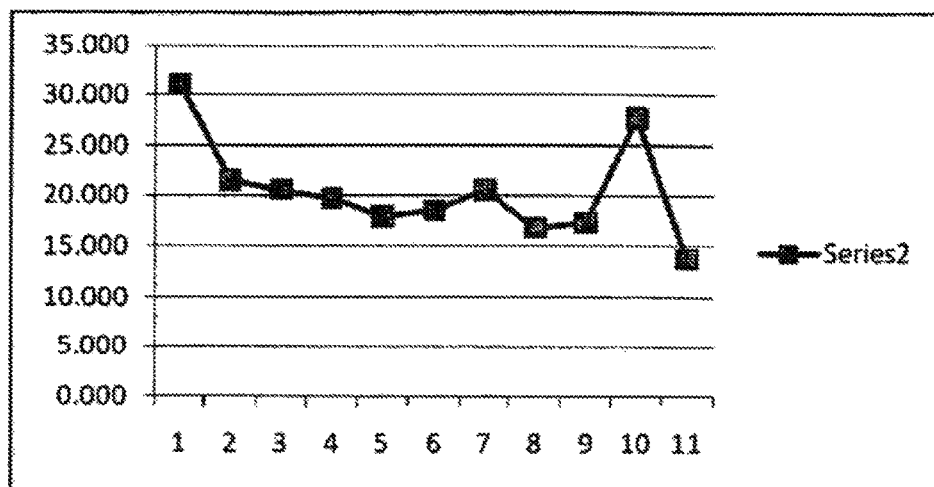
Figure 9:
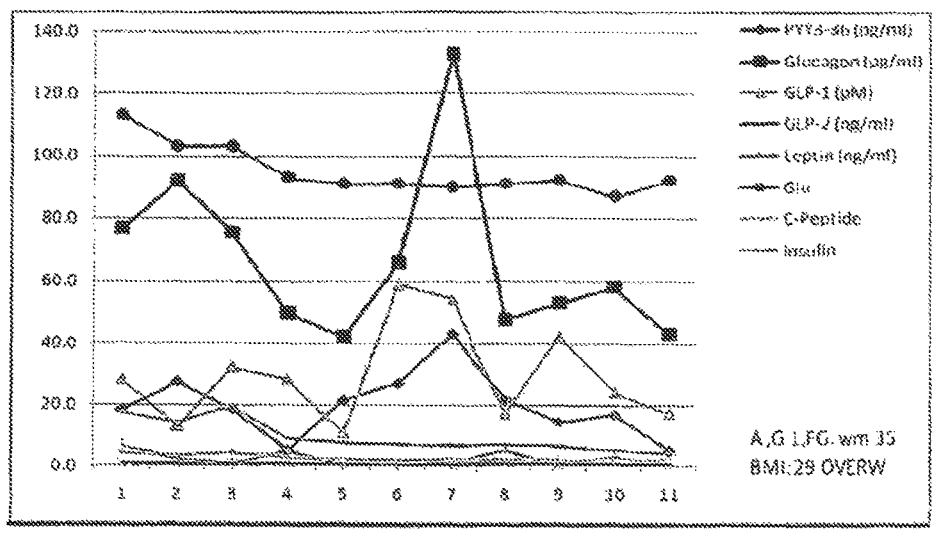
FIG. 9 is a chart showing the change in levels of various blood components during testing, with Table 1 showing the data, for the following subject: white male, 35 years old with a BMI of 29 (overweight). Note that the following is applicable, where relevant for FIGS. 9-28: GLP-1 (pM, ria), GLP-2 (ng/ml), Glucose (mg/dl), c-peptide (ng/ml), Insulin (μIu/ml), GLP-1 (total) (ria), PYY (3-36, pg/ml), Leptin (ng/ml), Glucogon (pg/ml), IGF-I (ng/ml) and IGF-II (ng/ml).
Figure 10:
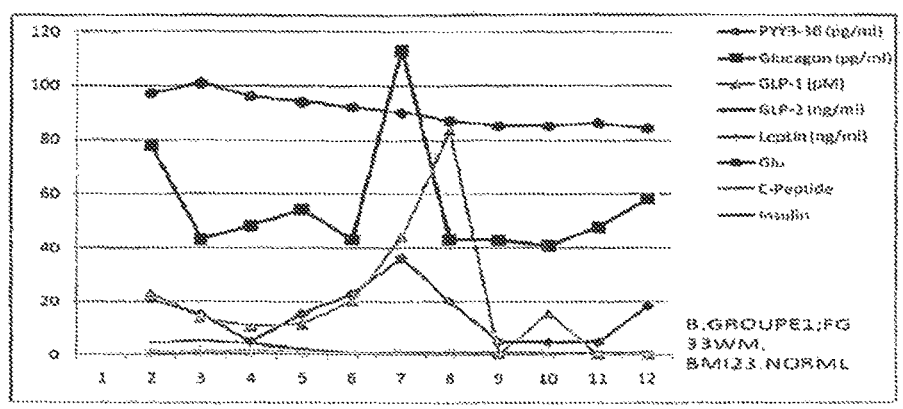
FIG. 10 is a chart showing the change in levels of various blood components during testing, with Table 2 showing the data, for the following subject: white male, 33 years old with a BMI of 23 (normal)

FIG. 2 illustrates four-month weight loss and blood sugar levels of a subject who took a single capsule according to formulation 1 once-daily in the fasted state at bedtime (about six to about nine hours prior to the subject's next intended meal) for a period of about four months. As illustrated in FIG. 2, the subject achieved a significant decrease in weight (about 24 pounds) at the end of about four months. The subject's blood sugar levels also improved significantly over the course of formulation 1 administration. Over the course of the four month period, the subject experienced periods of satiety that lasted as long as 12 hours or longer, and enjoyed a substantial overall caloric intake reduction. By the end of the four month period, the subject would no longer be diagnosed as obese and had blood sugar levels that were well within acceptable ranges.

Example 3

Formulation II

| Blend: | Amount | Range |
| --- | --- | --- |
| Alfalfa Leaf | 3.00 | 1-10+ |
| *Chlorella* Algae | 3.00 | 1-10+ |
| Chlorophyllin | 3.00 | 1-10+ |
| Barley Grass Juice Concentrate | 3.00 | 1-10+ |
| Dextrose | 1429.00 | 500-3000+ |

Other Tablet Ingredients:

| | | |
| --- | --- | --- |
| Coating * | 388.40 | 125-750+ |
| Corn Starch NF | 80.00 | 25-160+ |

| | | |
|---|---|---|
| Hypromellose USP | 32.40 | 10-65+ |
| Stearic Acid NF (Vegetable Grade) | 19.50 | 6.5-35+ |
| Triacetin FCC/USP | 19.30 | 6.5-40+ |
| Magnesium Stearate NF/FCC | 7.00 | 2.5-15+ |
| Silicon Dioxide FCC | 2.50 | 0.75-5.0+ |

* Depending upon the composition used, 10% by weight Aqueous Nutrateric Enteric Coating (from Colorcon, Inc., Aphoeline-0)/Livea-0 in the examples) as described below (for formulation III), 10% by weight Aqueous Shellac (Mantrose Haeuser, Inc. Aphoeline-1/Livea-1), 8% by weight Aqueous Indian Shellac (Aphoeline-2/Livea-2) was used to coat the formulations.

Formulation II was provided by mixing the actives with corn starch, stearic acid, magnesium stearate and silicon dioxide and pressing into a tablet, and coating the tablet with shellac (either 10% or 8% shellac), triacetin and the hypromellose. A eudragit coating could alternatively be used, similar to that which coats formulation I, as described above.

Based upon the results in examples 1 and 2, the inventors embarked upon a project to create a vehicle which can be given orally and deliver the nutritional substance to the ileum to stimulate the ileal break. The following data (appearing in attached FIGS. 3-8) reports the results of the experiment conducted on the formulation II composition. A number of formulations of pills with different coatings and structures and at times sub coatings were also used and tested and analyzed such that formulation II resulted. With the initial results, it was apparent that the pill composition and content indicate a logical pattern consistent with the hypothesis of stimulating the ileal hormonal break to induce satiety. The experiments were also performed to answer the issue of consistency of effect and the results obtained suggested that the approach was amenable for standardization and usage as a therapeutic composition, as well as a diagnostic tool in the future, the extra results showed improvement of the blood sugar and on subsequent testing of insulin and C-peptide showed that stimulation of insulin and C-peptide did not full explain the theory involved in decreasing insulin resistance. Leptin, IGF1 and IGF2 were measured and our results evidence that the stimulation of those factors contribute to the stabilization of blood sugar and reduction in insulin resistance observed.

The experiment was performed on volunteers as part of the testing of the different compositions, and structure of the pill in order to determine the best stimulation. The present example reports the results of the five patients that took formulation II as well as the graphs associated with it (FIGS. 3-8). Informed consent was obtained prior to administering the composition to five fasting volunteers, allowing them water only ad libidum throughout the day. They were given the recommended daily dose of formulation II after being examined by a physician and their vitals deemed appropriate for the test. A base line level blood level was obtained at hour 0 then hourly thereafter till hour 10. The blood was collected by a registered nurse, labeled accordingly and coded by a professional national lab, prepared according to the instruction of another out of state specialized national lab including cold centrifuge immediately upon receipt of the sample. The labeled coded samples were stored in dry ice refrigerated and shipped to 3 different specialty national labs for analysis and measurement of the metabolic and hormonal levels. The data was forwarded as per code numbers to the local national lab and encoded appropriately to match the volunteers for analysis. Analysis was performed and graphs were drawn accordingly. No unusual event occurred; Applicants were surprise with the results of one individual for the extremely high level of gpl1 that did not follow the same pattern as the others. Even though it was advantageous to maintain that individual within the data to enhance the statistics, Applicants removed that data from the data presented.

Applicants note that the other pill compositions tested showed similar but less significant stimulation and a slight modification in pattern, in accordance with the expected formulation release and stimulation of the pills. The subjects were monitored at all times by a registered nurses and a physician. The results appear in FIGS. 3-8. Those figures clearly evidence that the compositions of the present invention had a favorable impact on blood glucose, reduced insulin resistance, and had favorable impact on glucagon, GLP1, blood glucose, C-peptide, insulin, PYY, Leptin, IGF-1 and IGF-2. Note that the IGF1 and IGF-2 parameters may help explain some of the significant difference in muscle mass preservation observed and reduced fat mass using the present compositions. The results for GLP1 (FIG. 6) suggest satiety as well as favorable body composition (reduce fat/increased muscle), which matches to a certain extent the levels achieved with bypass surgery without the attendant complications and side effects of such surgery. The results for PYY (FIGS. 7A-E) follow a similar stimulation pattern with earlier stimulation coupled with sustained stimulation at the level of about 3-8 hours and maximum intensity of 4 to 10 hours after the ingestion of the present composition. The patterns are predictable and amenable to standardization and are indicative of ileal peptide stimulation which contributes to appetite suppression.

Regarding the response of glucose, c-peptide and insulin to the composition of the present invention, that data is summarized in FIG. 8A-J. Given the wide variation and the response of glucose/insulin interaction, the inventor divided the patients into categories with different starting points to determine if there is any difference in the action of the present compositions on the different groups (normal glucose/mild elevation insulin; elevated glucose/normal to low insulin levels; elevated glucose and elevated insulin; normal glucose/elevated fasting insulin and normal glucose/mild insulin increase). The principal effect of the present compositions is homeostasis; regulation of blood sugar and insulin is in a manner consistent with the suppression/reduction of insulin resistance and an increase in glucose tolerance (by upregulating ileal hormones, IGF-1, IGF-2 and leptin). In the first group (normal glucose/mild elevation insulin, FIG. 8A-B), the insulin levels are suppressed with a slight decrease in glucose levels, consistent with suppression of insulin resistance. The second group (elevated blood sugar/normal to low insulin levels, FIG. 8C-D) demonstrated that in the absence of insulin stimulation is similar to a typical stimulation of insulin in type 2 diabetes, with the peak of stimulation of insulin stimulation occurring early in the process, but with insulin declining later in the process, evidencing homeostasis and a reduction in insulin resistance and enhanced glucose tolerance over time. The third group (elevated blood sugar and insulin, FIG. 8E-F) demonstrates the continual seesaw between insulin stimulation and suppression as it relates to suppression of insulin resistance as insulin trended down over time with insulin evidencing bouts of stimulation within a cycle. The fourth group (normal glucose/elevated fasting insulin) evidenced decline in glucose and insulin consistently over time (significant insulin decline with 3-4 hours after administration of composition). In the fourth group (normal glucose/mild insulin increase, FIG. 8I-J), insulin reduction with decrease in blood glucose further evidenced suppression of insulin resistance.

In this set of experiments, the inventor was able to stimulate hormones of the ileal break using a safe, effective oral formulation comprising nutritional supplements with enteric release (delayed/controlled release) to generate a feeling of satiety that occurs naturally after meals, while helping to curb appetite in a natural way without the side effects of prior art methods. The experiments evidenced a coherent pattern of hormone release that can serve as a diagnostic tool for testing the ileal break hormones for insufficiencies, excesses or other abnormalities. Also shown is the fact that the present invention stimulates IGF1 and IGF2 and leptin as well as decreasing/suppressing insulin resistance and enhancing glucose tolerance, giving it excellent prospects for treating NIDDM (type II diabetes mellitus), prediabetes, metabolic syndrome and insulin resistance. By stimulating the ileal hormones pursuant to the present invention, the present invention represents an enhancer of well being, muscle mass preservation or production. Further, the present invention also is able to stimulate glucagon, glucagon-like (enteroglucagon, etc.).

Example 4

An experiment was undertaken using two different formulas (including formula II, above, in order to determine the maximum yield of the pills given to subjects volunteers. The volunteers were divided in groups of 7, and different pills compositions were given to each.

The object was to investigate and measure multiple parameters besides blood sugar, such as glucose homeostasis to include insulin, c-peptide, glucose, igf1, igf2, glucagon, as well as leptin. The composition of the pills was developed in such a way so as to decrease the number of pills from an initial 16 to 7. The pills were given orally while fasting, and the blood work was drawn hourly for all parameters and each tube was coded for both time and patient. The blood product was handled by a professional staff prepared as required by the different tests, and the samples sent to two different national labs that provided results in coded numbers.

Once decoded and analysed for each patient, the results were taken as the average response to the different parameters for the different patients, that is those that started with either an abnormal insulin level, abnormal glucose level or both.

The two pills composition used during this testing were as follows (ingredients per tablet, in mg), Formula II (as above) in Example 3:

| Proprietary Blend: | Amount | Range |
| --- | --- | --- |
| Alfalfa Leaf | 3.00 | 1-10+ |
| *Chlorella* Algae | 3.00 | 1-10+ |
| Chlorophyllin | 3.00 | 1-10+ |
| Barley Grass Juice Concentrate | 3.00 | 1-10+ |
| Dextrose | 1429.00 | 500-3000+ |

Other Tablet Ingredients:

| | | |
| --- | --- | --- |
| Aqueous Shellac | 388.40 | 125-750+ |
| Corn Starch NF | 80.00 | 25-160+ |
| Hypromellose USP | 32.40 | 10-65+ |
| Stearic Acid NF (Vegetable Grade) | 19.50 | 6.5-35+ |
| Triacetin FCC/USP | 19.30 | 6.5-40+ |
| Magnesium Stearate NF/FCC | 7.00 | 2.5-15+ |
| Silicon Dioxide FCC | 2.50 | 0.75-5.0+ |

Formulation II was provided by mixing the actives with corn starch, stearic acid, magnesium stearate and silicon dioxide into a tablet, and coating the tablet with the shellac, triacetin and the hypromellose. The shellac was either a European shellac (Aphoeline-1/Livea-1) or an Indian shellac (Aphoeline 2/Livea-2), as described above.

Formula III used a coating composed of 2% clear polyvinyl alcohol (PVA) coating plus 14% of a nutrateric coating (Aphoeline-0/Livea-0). The clear coating was made up of polyvinyl alcohol, talc, polyethylene glycol, polysorbate 80; the nutrateric coating was made up of ethyl cellulose, ammonium hydroxide, medium chain triglycerides, oleic acid, stearic acid. The proprietary blend of active ingredients comprised sodium alginate and dextrose, 1150 gm (85% by weight of Formula III).

Protocol Testing.

All subjects were volunteers that signed an informed consent in regard to the GRAS compliant supplement which was to be administered. Each subject presented fasting, with the last oral intake having occurred the night prior. Baseline lab work was completed, including blood sugar, insulin and, c-peptide, as well as other hormones. Samples were collected by licensed professionals, and handled by professional lab technicians. The sample tubes were labeled according to a preset protocol, for anonymity and shipped in frozen containers as specified by the contracted, licensed labs for testing.

Sampling was done on an hourly basis, before and after the oral ingestion of the supplement. Vitals were taken before each draw. No food or drink was allowed prior or during the test, though water was allowed adlib. The results were compiled in the enclosed Tables, illustrated by the enclosed charts comprising FIGS. 9-28 and Tables 1-21.

The subjects selected were part of a much larger group, with only those that were found to have abnormal insulin or abnormal blood sugar or both included. There were no significant changes in levels of insulin, glucose or c-peptide for the rest of the group.

As evidenced by the figures and the corresponding tables, generally, blood sugar as well as insulin decreased and/or stabilized, in response to administering the nutritional supplement, which apparently results in a hormonal stimulation. This response appears to be greater the higher the starting value, indicating a significant decrease in insulin resistance. Also it can be noted that the more normal the value of insulin and glucose, the less significant are the changes to their values, indicating that the effect of the pill is self limiting, that is, surprisingly, the nutritional supplement acts favourably to correct abnormal levels but does not pose a danger of decreasing blood sugar below normal, so there is no risk for hypoglycaemia. This makes the nutritional supplement particularly useful in persons who are only exhibit pre-diabetic symptoms, where drug therapy has not yet been indicated or is not preferred given the risk of side effects.

Established safe and effective dose ranges in humans for the nutritional supplement of the invention ranges from 500 to 12500 mg/day, preferably within the range of about 7,500 mg/day to about 12,000 mg/day, preferably about 10,000 mg/day. While not being limited by way of theory, the product therefore negates/reduces insulin resistance, thereby allowing blood sugar to enter the cells, with insulin at normal levels, as opposed to the abnormally high levels of insulin generated in the test subjects, and therefore decreasing insulin levels to base line. This allows the body to use more energy while decreasing the noxious effect of high insulin that promote obesity as well as the vicious cycle associated with high insulin levels, such as per metabolic syndrome, polycystic ovaries, arteriosclerosis, hypertension, fatty liver, etc.

The insulin production modulation achieved by administering the inventive formulating containing GRAS ingredients is believed to occur through the action of a stimulated hormone within the lower gut, which either acts through igf like receptors or through a different receptor than the receptor for igf or insulin, possibly like receptor IRR. Since the nutritional supplement composition is not absorbed and appears to work through hormone stimulation, a new hormone from the same area could be stimulated as well that acts on a receptor, either its own or through IGF stimulation.

Accordingly, pursuant to the present invention, it was discovered that a nutritional supplement composed of GRAS compliant ingredients is effective in treating noninsulin dependent diabetes mellitus, pre-diabetic symptoms, and insulin resistance, with no side effects, by acting to suppress insulin resistance, lower/stabilize blood sugar, and therefore could be used in treating all form of insulin resistance as per NIDDM, polycystic ovary as well as type b insulin resistance.

Further Discussion

GLP-1, an insulinotropic hormone released from the intestinal L cells in response to nutrient ingestion, has been extensively reviewed with respect to beta-cell function. GLP-1 is both a gut-derived hormone and a neurotransmitter synthesized in the brain. Early reports suggested that GLP-1 acts in the periphery to promote insulin secretion and affect glucose homeostasis, whereas central GLP-1 reduces food intake and body weight. However, current research indicates that in fact, GLP-1 in each location plays a role in these functions. There is substantial evidence for involvement of peripheral and brain GLP-1 in food intake regulation and glucose homeostasis and proposes a model for the coordinated actions of GLP-1 at multiple sites.(19) However, GLP-1 receptors are abundant in many other tissues. Thus, the function of GLP-1 is not limited to the islet cells, and it has regulatory actions on many other organs. For example, it has been suggested that GLP-1 may have benefit in Congestive Heart Failure (20). GLP-1 has the ability to modulate myocardial glucose uptake and thereby make an impact on cardio protection. (this is for improving muscle function and heart) Glucose-insulin-potassium (GIK) infusions have been studied for decades, with conflicting results regarding benefit in acute myocardial infarction. Based on the same concepts, GLP-1 has recently been demonstrated to be a more effective alternative in left ventricular (LV) systolic dysfunction (20).

A review of published, peer-reviewed medical literature (1987 to September 2008) on the extra pancreatic actions of GLP-1 was performed (21). The extra pancreatic actions of GLP-1 include inhibition of gastric emptying and gastric acid secretion, (this is to help in decreasing acid secretion and prevention of cancer of the esophagus) thereby fulfilling the definition of GLP-1 as an enterogastrone. Other important extra pancreatic actions of GLP-1 include a regulatory role in hepatic glucose production, the inhibition of pancreatic exocrine secretion, cardio protective and cardio tropic effects, the regulation of appetite and satiety, and stimulation of afferent sensory nerves. The primary metabolite of GLP-1, GLP-1 (9-36) amide, or GLP-1m, is the truncated product of degradation by dipeptidyl peptidase-4. GLP-1m has insulinomimetic effects on hepatic glucose production and cardiac function. Exendin-4 present in the salivary gland of the reptile, Gila monster (Heloderma suspectum), is a high-affinity agonist for the mammalian GLP-1 receptor. It is resistant to degradation by dipeptidyl peptidase-4, and therefore has a prolonged half-life. In conclusion, GLP-1 and its metabolite have important extra pancreatic effects particularly with regard to the cardiovascular system and insulinomimetic effects with respect to glucose homeostasis. These effects may be particularly important in the obese state. (21).

Given the above importance of glp1 and the effect of increasing its levels even higher the use of ddp4 inhibitor in conjunction with an increase in stimulation with Livea should be thought in maximizing Livea effect to a pharmacological level that should work much better than the peripherally injectable medication that are exending like compound that lack the primary portal concentration that control blood sugar and hepatic glucose release as well as insulin secretion and mesenteric fat use, acting in a physiological way will prevent complications and side effect and improve outcome. therefore the use of Livea with dpp4 inhibitor available on the market can target type 2 diabetes and prediabetes and serve as a pharmaceutical drug more powerful and natural with less side effect in all diseases mentioned By contrast, food-related stimulation of GLP-1 is hyporesponsive or even absent in obese patients. Marks et al. also showed a remarkable absence of GLP-1 response to oral glucose in obese patients (22), indicating a down-regulation of the ileal brake pathway in the pathogenesis of obesity. On the other hand, obese patients who undergo bariatric surgery lose weight gradually by suppression of appetite. They also experience very positive impact on glucose levels in the blood and improvement in insulin resistance. One possible explanation for all of these effects is an activation of the ileal brake pathway by bariatric surgery, just as would be expected from the experiments delivering high amounts of nutrition to the ileum via an enteric tube (23, 24). Thus, the present invention also relates to its use as an alternative therapy or concomitant therapy or pretherapy or post therapy to bariatric surgery)

In 1996 it was postulated that this stimulation happens via neurotransmission (25), and to some extent involves GIP indirectly via neuron-stimulation of the ileal brake hormones. The effect could be inhibited by lowering neuron stimulation using blockers. Others have challenged these findings, and alternatively proposed that the ileal brake effects are mediated directly by the L-Cells that are found throughout the intestinal tract. In fact they argue that the effect on L-Cells coexists with the GIP hormones in the upper jejunum and with PYY in the lower gut.

Fractionation experiments with enteroglucagon resulted in isolation of GLP-1 and GLP-2. Because of its insulin activity GLP-1 is used to treat diabetics, and was noted to have significant weight loss properties. Analogues to GLP-1 made available for treatment of diabetes such as Exenatide (Byetta) are associated with favorable glucose control and appetite suppression associated weight loss. Other hormones in the ileal brake pathway, such as PYY analogues, were also made available and trials were also designed to use these in the treatment of human obesity.

Hoist and colleagues (2006) published a detailed review on the action of GLP-1 on different parts of the body to include the muscles, nervous system, the heart as well as the pancreas the liver intestine and brain (26). GLP-1 was shown to be a powerful regulator of food intake in humans at physiological levels (27, 28). GLP-2 targets growth and regeneration of the enteric organs, therefore acting as a growth factor hormone which serves in the recovery of the body from injury (32-37). This helps the (this will help the body to recover from injury related to event such as chemotherapy, radiation, mechanical injuries such as surgeries or trauma, or infectious). PYY was shown to induce satiety as well as to suppress acid secretion combined with GLP-1, and act on motility significantly (38, 39). PYY was also tested by both injection and nasal administration, but was itself unsuccessful for prevention and treatment of obesity. Some studies suggest that stimulation of all the hormones of the ileum simultaneously worked synergistically to suppress appetite and regulate both glucose and insulin, and the result of this synergy was notable by its actions at lower doses and mainly on the portal system.

Beside the above we noted that triglyceride levels decreased even more significantly tan above liver enzymes indicating that the present invention can be used to target steatohepatitis as well as hyper triglyceride. On another subject Livea in one patient on treatment for hep c genotype 1a, reversed the increase of virus count during a conventional therapy with interferon and ribavirin therapy that usually is interpreted as resistance of the virus to treatment back to a normal responsive trend, indicating a change in the patient immune response to the therapy.

On another subject a patient on treatment for autoimmune hepatitis worsening liver enzymes and meld score on steroids and cellcept, turned the corner with the liver enzymes once on Livea and improved her liver enzymes again indicating an improvement and change in the patient immune system indicating a more generalized indication for liver disease beyond the metabolic condition. or another explanation that all liver diseases have a common important factor in response to any injury that relate to the way the liver respond to injury and seems that Livea is affecting it Discussion Injection of analogue of GLP-1 peripherally is a familiar approach in the treatment of diabetes, and produces appetite suppression in a manner similar to Livea treatment. However, the properties of peripheral GLP-1 include a different distribution pattern and a short half life of approximately 3 minutes. The majority of the dose does not enter the portal system as it would if GLP-1 was induced by GI tract stimulation and with peripheral administration less than 15% will go through the liver to the periphery. While exogenous use of enteric ileal brake hormones is demonstrated to have an effect on appetite suppression, the idea of resetting the endogenous ileal brake in the lumen of the GI tract has not been tried before, other than by bariatric surgery. The ileal brake pathway is optimally activated LOCALLY in the distal small bowel, and when stimulated properly these ileal brake hormones act synergistically and in a highly complementary manner, which both avoids side effects associated with only one of them administered parenterally. The drawback to the peripheral injection approach of GLP-1, although proven to have appetite suppression, is partly a delivery site problem. For example, subcutaneous injection of GLP-1 mimetic, at supra-physiological levels, does not allow the advantages of portal application of lowered amounts. Thus the liver and pancreas effects are not beneficial; only the brain appetite suppression axis is activated. Furthermore there are GLP-1 receptors in non-target organs like the heart and kidney, and these may explain some of the recently noted side effects of Exenatide. Thus the portal system is where most of the action is taking place, and activation of the local ileal brake pathways lead to the full complement of benefits beyond appetite suppression. With oral administration of Livea, there is appetite suppression, but also beneficial effects on glucose control, insulin pathways, re-set pancreatic glucose sensors, hepatic glycogen storage and glucose release, and mobilization of adipose tissue.

The actions controlled by Alphoeline/Livea are in the GI tract itself all the way from the esophagus to the rectum. Another problem with peripheral GLP-1 is the development of antibodies to the peptide within one year and up to 40% of the treated patients with Exenatide. The other side effects of Exenatide include pancreatitis and renal failure associated with the treatment.

On reviewing the literature in regard to appetite control and obesity the mainstream approach has been caloric counting and exercise. Excessive caloric intake has been linked to a psychological problem. As a consequence, from the patient viewpoint they are either addicted to food without will power or the patient is not sufficiently active to compensate for the intake of calories (49). Though valid, these statements do not give an accurate picture of the problem afflicting the large proportion of patients that appear to be very balanced psychologically and despite their best efforts are not capable of losing weight. Some reviews suggest that people under stress tend to lose less weight than people under less stressful situations, ascribing cortisol as the etiological factor. Other studies using a rat model (48) suggest that obesity is predetermined and one will tend to go back to the genetic curve with age.

We do know that certain conditions, including diabetes, hypertension, insulin resistance, commonly used antidepressants and anti-psychotics are associated with weight gain. The effect of bariatric surgery on patients with obesity and concomitant diabetes also seem to be mediated thru the suppression of appetite centrally after local GI activation of the ileal brake pathway. The mechanism of action is not psychological as oral caloric intake and energy expenditure, since patients with a bypass surgery for obesity have improved appetite control compared to people that undergo a lap band surgery. The effectiveness of bariatric surgery is also related to the connection site of the bypass. Make it too short and severe malabsorption results, while if the loop is too long the patient does not lose weight. Another consistent observation is the favorable weight loss action of LIRA-GLUTIDE in spite of no major changes in patient behavior or lifestyle (29).

The other approach to the treatment of obesity is to try to bypass different systems like providing medications that work directly on the satiety center by different medications that are available on the market. The different side effects that will have to be dealt with include hypertension, stroke, addiction, seizures, cardiac arrhythmias and coronary events, pulmonary hypertension, severe depression, suicide, and insomnia. Even when the patient looses weight, there is a rebound off medications associated with binge eating and the patient ends up being either recycled in the system for another course of therapy in weight control centers, or gaining more weight than he started with, putting him at risk that could be higher than the baseline due to the severe weight fluctuations over short periods of time. Vildagliptin is a selective dipeptidyl peptidase IV inhibitor that augments meal-stimulated levels of biologically active glucagon-like peptide-1. Chronic Vildagliptin treatment decreases postprandial glucose levels and reduces hemoglobin A1C in type 2 diabetic patients. However, little is known about the mechanism(s) by which Vildagliptin promotes reduction in plasma glucose concentration. METHODS: Sixteen patients with type 2 diabetes (age, 48+/−3 yr; body mass index, 34.4+/−1.7 kg/m2; hemoglobin A1c, 9.0+/−0.3%) participated in a randomized, double-blind, placebo-controlled trial. On separate days patients received 100 mg Vildagliptin or placebo at 1730 h followed 30 min later by a meal tolerance test (MTT) performed with double tracer technique (3-(3)H-glucose iv and 1-(14)C-glucose orally). RESULTS: After Vildagliptin, suppression of endogenous glucose production (EGP) during 6-h MTT was greater than with placebo (1.02+/−0.06 vs. 0.74+/−0.06 mg·kg-1·min-1; P=0.004), and insulin secretion rate increased by 21% (P=0.003) despite significant reduction in mean plasma glucose (213+/−4 vs. 230+/−4 mg/dl; P=0.006). Consequently, insulin secretion rate (area under the curve) divided by plasma glucose (area under the curve) increased by 29% (P=0.01). Suppression of plasma glucagon during MTT was 5-fold greater with Vildagliptin (P<0.02). The decline in EGP was positively correlated (r=0.55; P<0.03) with the decrease in fasting plasma glucose (change=−14 mg/dl). CONCLUSIONS: During MTT, Vildagliptin augments insulin secretion and inhibits glucagon release, leading to enhanced suppression of EGP. During the postprandial period, a single dose of Vildagliptin reduced plasma glucose levels by enhancing suppression of EGP.(40)

Other approaches to weight loss target absorption, create states of malabsorption, produce stool incontinence, and may result in fatty liver and other undesirable effects (51).

Based on these premises leaders in the field started to emphasize a more natural GI tract based approach to weight loss that would involve all the endogenous mechanisms that regulate caloric intake and body weight. The goal was to lose more weight with fewer side effects, and the standard is Bariatric Surgery. A recent review of approaches to this problem eloquently summarizes the field (17, 41-44). The focus is shifting to the ileal brake pathways that are using the body natural signals: the gut hormones for future research of obesity pharmacotherapy (45, 46).

Based on our clinical observations, there is a component of hunger and obesity that is visceral and unconscious. To a certain extent, these effects are unknown to the patient, making it very difficult for the person to control appetite. The person at the time will be trying to replace the lack of visceral perception with an alternative voluntary conscious awareness resulting in continuous monitoring of the calories and input output as well as calories used and activity at all time to control the weight. This is difficult, and often causes frustration to those attempting to lose weight in this manner.

Going back to the literature trying to figure out the different responses of the body to food between normal and overweight or obese patients, the only significant abnormality that was reported, is the response of the ileal break to the intake of the mixed meal (17, 22), and more specific to carbohydrates. Therefore it seems the natural satiety pathways become tolerant to the intake of carbohydrates. This partially explains the success of the Adkins diet, even though in this case there are no demonstrable differences in the anatomy or histology of those two groups, except in rare cases of severe morbid long term obesity associated with atrophy of the ileum. Given the fact that food delivered to that part of the intestine is capable of stimulating those hormones independently of oral intake and the fact that the ileal stimulation during a mixed meal can be inhibited by suppressing the neurotransmission raise the possibility that the problem seems to be about the transmission of the signal from gut to brain. It is possible that a reset of a carbohydrate tolerant ileal brake pathway will re-set the appetite center and renew the feedback loop that interrupts eating, all without progression to a metabolic syndrome. Therefore if we are able to directly stimulate the ileum we should be able to restore the ileal brake signal and at least give the patient some help in restoring visceral signals that measures the food intake.

These visceral signals are not only important to signal satiety but as per reported reviews (34, 44) these hormones are extremely beneficial to the patient. Their absence during down-regulation could be what the patient's are seeking unconsciously when they overeat, energy improve muscle, liver, intestine stomach, nerve and heart. Since these hormones are also very important in the homeostasis of the insulin and glucose levels they will help tremendously in the use is of the reserves that are already present.

By stimulating the hormones naturally with Aphoeline/Livea we are delivering the majority of the hormones where they belong in the portal system, where they have the most powerful impact on satiety. We were also encouraged by the fact that the bypass surgery for obesity is capable of stimulating those hormones in all patients, indicating that the innate ability of these hormones to respond is still present.

We set a goal to stimulate the ileal hormones with an oral natural agent consistent of a nutritional substance. The data are compelling and the stimulation of the ileal brake pathway seems independent of age or weight or diabetes. This establishes the intestine still functions despite obesity, and the problem seems to be in the down-regulation of the signaling from the ileum. (Another confirmation to that statement comes from the surgical bypass that in appropriate individual triggers the same process).

What we discovered from these stimulation that it have a very powerful effect on the glucose and insulin homeostasis not consistent with the assumption that these peptides work only by stimulation of the insulin but mainly through reducing insulin resistance as well long before they achieve weight loss. This is also consistent with the data from bypass surgery.

The more powerful effect on steato-hepatitis seen by decrease of the enzymes level to normal within 3-4 weeks need to be studied on a much longer duration to confirm the trend and the gains, but it seems from the energy, satiety and the trend to normalize triglyceride and cholesterol as well as to the satiety factors and surprising improvement of all parameters including platelets that the trend is true. Similar platelets trend is seen in cirrhotic patients (non-published data).

Based on the recent publication of Lirutaglide and weight loss(29), the GLP-1 family of gut hormones will induce weight loss but in a different way than expected, the weight loss is slow and happens after other parameters start to improve. Weight loss is insidious, just like weight gain, and occurs on a rather unconscious level. The pathway is re-activated after being dormant and the distal caloric signals are now once again responded to in the ileum.

The advantage of having an oral stimulation of all the ileal hormones is the synergistic effect of the hormones that were meant to be stimulated together in a broad pathway beyond any individual component. The fact that these hormones are released in the portal system that seems to be the center of all metabolism except the muscles and the brain, the fact that the highest concentration of these hormones is in the portal system make our stimulation much less intrusive and more efficient than the peripheral administration of such hormones.

The suppression of insulin resistance need further investigation even though we showed that the IGF system is stimulated, we do not feel this is the only answer to the question; other peptides as well as other cellular receptors such as the RR receptors need to be investigated as part of the equation. In the next section, we prioritize our future work in this direction.

Further Examples (Figures for Further Examples Labeled with E)

Project Description

Given that the most natural way to stimulate those hormones is the gut stimulation of the ileal brake pathways, we devised a project and a product to reset the ileal brake in patients. The major goals were:
1. To establish proof of concept with oral activation of the ileal brake pathways, whereby an oral pill containing food content that is protected with an enteric-coating mechanism, could deliver this food content to the distal ileum, and thereby stimulate ileal brake hormones.
2. To demonstrate that stimulation of the ileal brake with this formulation is reproducible and can cause the released ileal hormones to reach significant levels physiologically in humans.
3. To determine a time related pattern of response to stimulation of the ileal brake and to use the local enteric stimulation as means of re-setting the ileal brake of obese patients.
4. To demonstrate stimulation of the ileal brake in overweight and obese patients.
5. To demonstrate that the increase in the hormones of the ileal brake cause weight loss in obese patients by regulating gut-brain satiety signals and therefore appetite.
6. To study the interactions between ileal brake hormones and systemic effects, such as control of blood sugar, insulin homeostasis, and appetite control.
7. To establish doses, administration times and optimal schedules for Aphoeline/Livea in treated patients with obesity.

This project was designed to reset a biological process regulating satiety and appetite. It tests an endogenous pathway that appears to be hypo-responsive in obese patients. It is believed that a reset of the so called ileal break mimics the effect of bariatric surgery in the obese patient, without exposing the obese patients to the risks of surgery. If successful, the product will use an existing pathway, associated controls and feedback loops, avoiding complications and side effects. We will help the body regain control of the intestinal factors that regulate ingested nutrients and weight. Furthermore, giving patients control of an unconscious part of satiety, a pathway that is very difficult to deal with at the conscious level, will make it easier for them to follow a diet and lose weight. There is no evidence that the hypo-responsive ileal brake in obese patients is an organic defect that cannot be subject to external regulation, although it is theoretically possible since some patients do not respond to bariatric surgery.

Methodology:

As a starting point we needed to calculate the amount of food needed to deliver to the ileum. For that purpose we decided to use carbohydrate as a starting solution. Carbohydrate is a significant stimulus to the ileal brake mechanism (12), and it was easy to monitor for any absorption or failure of the pill by checking the blood sugar level. Finally, absorption of carbohydrate stops much sooner than fat and gives us more room for the initial testing of the pill.

Based on the above we have to calculate the right amount of calories to be delivered to the ileum. We decided to proceed with testing the minimal amount of carbohydrate needed to stimulate insulin and be visible in the blood stream; we termed this a minimal metabolic unit. The thought behind it was that if the upper gut was able to perceive it as food, the lower gut that is supposed to monitor malabsorption should be able to react to it as a signal of malabsorption. It was determined that the unit should be between 8 to 15 gm of carbohydrate. The amount used in the direct ileal stimulation experiments was around 15 gm (12).

The second task was to have the coating for the pill to deliver the carbohydrate to the ileum without proximal small bowel absorption. This required a slow release formulation to avoid an osmotic side effect.

Because of the amount of carbohydrate involved in re-setting the ileal brake, the goal was to decrease the number of the pills, starting at 18 and decreasing the number to a manageable level of 7 per day. The formulation and dose finding experiments started in 2003, and by 2008 we had arrived at 4-5 different formulations that withstood these in-vitro challenges and were ready for testing.

Three trials were conducted with pilot formulations to arrive at the components of Aphoeline/LIVEA (pursuant to the formulations, provided above). After informed consent from healthy volunteers, monitored at all times medically the pills were given after an overnight fasting state and blood work was drawn on an hourly basis for 10 to 12 hours testing. Measured were the peptide ileal brake associated hormones and their associated biomarkers: blood sugar, insulin, c-peptide, and in the last tests IGF-1, IGF-2. Patients were allowed to drink water ad libitum. The samples were drawn according to the recommendations of the various specialized labs by professional registered nurses, and the blood was handled on the premises by a reference lab (which one) immediately on withdrawal, each tube coded accordingly packaged on dry ice and shipped overnight to the specialty labs.

Patients were separated in different groups. The groups were handled sequentially. Each subject in the group was handled simultaneously with the other elements of his group at a separate drawing station with a registered nurse, according to the time schedule. Therefore group 1 was done all at one time at the different stations from one to seven, the time frame was kept by an independent monitor to try to assure punctuality.

Initially the groups were processed and paper were filled out with a short history and physical, consent were signed, and a heparin lock was placed by the nurse at the station, then a draw at zero time was done, time was marked then the pills was given to all individual of group at the same time. The same was done to the other groups sequentially. Blood was drawn thereafter as per protocol on an hourly basis on the clock for all members of the group simultaneously, at every draw the person and vitals were assessed and blood drawn from the heparin lock, after saline flush and after discarding the first cc s to avoid high heparin concentration. For testing the GLP-1, GLP-2, and PYY was as follows: EDTA (purple top) tubes with addition of 500 micro liters of Aprotinin and 10 micro liters of DPP IV per tube. Collect blood, centrifuge within 10 minutes in a 4 degree C. centrifuge. Pour off supernatant (plasma) and immediately freeze. 2.5 ml plasma to a container or combine two plasmas from the same subject at "same time point" into a 6 ml container. Labeled and code each tube separately according to a pre organized labeling system. The tubes were Stored and ship these specimens at −70 C. The Insulin, C-peptide and glucose were collected in SST tubes, spun and sent to the local national lab.

Results were reported from the reference lab and decoded back in standard excel format, and forwarded to us for analysis.

The results were studied by statistical analysis: the results are as follows:

Heparin lock, after saline flush and after discarding the first cc s to avoid high heparin concentration. The blood was placed in 2 separate tubes from the same draw to assure redundancy and control, in Vacutainer tubes containing protease inhibitors (EDTA, Aprotinin, and DPP IV inhibitor) cocktails. After blood collection and centrifuged in refrigerated centrifuge, in those tubes, then transfer the 2.5 ml plasma to a container or combine two plasmas from the same subject at "same time point" into a 6 ml container. To freeze, labeled and code each tube separately according to a pre organized labeling system then ship in dry ice as soon as possible to the peptide labs measurement preferably over night.

The hormone data set was statistically analyzed; the results are described in the next section.

Results of Statistical Analyses

Alpholine/Livea has been developed after testing a sequence of formulations and careful statistical analyses of the blood test results. Testing was done at three different times with three different formulations, as shown in Table 1:

TABLE 1

Time of testing and formulation

| Time | Formulation | SUBJECTS* |
|---|---|---|
| August 2008 | Aphoeline-1 | A, F, G, H, I, J, K, P, U |
| September 2008 | Aphoeline-1 | E, K, N |
| Oct. 26, 2008 | Aphoeline-1 | A, B, C, D, E |
| Oct. 26, 2008 | Aphoeline-1 | F, G, H, I, J |

*There were different subjects at different testing times [e.g., Subject A in August testing is not same as Subject A in October testing] Formulations described above.

Results of Statistical Analysis:

The R software package for statistical computing was used for all statistical analyses and data visualization.

1) Measurements of GLP1, GLP2, and IGF-I, IGF-II, Glucose, Insulin, C-Peptide and pyy for each of the 10 subjects were plotted against time (FIGS. 29, 30, 31, and 32).

2) It can be seen from FIG. 31 (Further Examples) that [i] all 5 Aphoeline subjects [F, G, H, I, J] have elevated Glucose levels at time 0, [ii] except for subject G, the Glucose level monotonically decreases to normal levels; in the case of Subject G, Glucose level starts at 113, goes down to 98, goes up to 112 and then goes down to 108.

3) It is also apparent from FIG. 31 that two of the subjects [G and I] in the Aphoeline Group had slightly elevated insulin levels at time 0; in both of these cases, the insulin levels decreased by time 10.

4) FIG. 33 (Further Examples) shows the average concentrations of GLP1, GLP2, IGF-I, IGF-II, Glucose, Insulin, C-Peptide and pyy plotted against time of measurement for the Aphoeline-0 Group (concentrations at each time averaged over the subjects A-E), and FIG. 34 shows these averages for the Aphoeline Group (concentrations at each time averaged over the subjects F-J). We can see from FIGS. 33 and 34 that the average concentrations of Glucose and insulin decrease with time.

5) Mann-Kendall nonparametric test for trend was used to determine if both insulin and glucose levels decrease over time for Aphoeline-0 and Aphoeline Groups. These results are shown in Table 2, below. Apheoline

TABLE 2

Results of Mann - Kendall nonparametric test for trend

| Product | Subject | Mann - Kendall Statistic τ for Glucose | P - value for the alternative hypothesis of decreasing trend | Mann-Kendall Statistic τ for Insulin | P - value for the alternative hypothesis of decreasing trend |
|---|---|---|---|---|---|
| Apheoline -0 | A | -.5 | .02* | -.299 | .12 |
| Apheoline -0 | B | -.64 | .005* | -.441 | .055** |
| Apheoline -0 | B | -.524 | .015* | -.554 | .015* |
| Apheoline -0 | D | .82 | .0003* | .04 | .94 |
| Apheoline -0 | E | -.496 | .025* | -.93 | .00005* |
| Apheoline | F | -.774 | .0007* | .0556 | .44 |
| Apheoline | G | -.112 | .35 | -.33 | .09** |
| Apheoline | H | -.389 | .06** | .11 | .35 |
| Apheoline | I | -.624 | .005* | -.352 | .08** |
| Apheoline | J | -.61 | .007* | — | — |

*Downward trend significant at test size 0.05,
**downward trend significant at test size 0.1

TABLE 3

Results of Mann - Kendall nonparametric test for trend

| Product | Subject | Mann - Kendall Statistic τ for | | | | | |
|---|---|---|---|---|---|---|---|
| | | Glucose | | C-Peptide | | Insulin | |
| Product | Subject | τ | P - value | τ | P - | τ | P - value |
| Apheoline -0 | A | -.66 | .003* | -.673 | .003 | -.636 | .004* |
| Apheoline -0 | F | -.86 | .0002* | -.722 | .002 | -.807 | .0004* |
| Apheoline -0 | G | -.697 | .002* | -.66 | .003 | -.236 | .35 |
| Apheoline -0 | H | -.648 | .004* | -.74 | .002 | -.6 | .006* |
| Apheoline -0 | I | -.611 | .006* | -.785 | .000 | -.455 | .03* |
| Apheoline | J | -.623 | .005* | -.648 | .004 | -.309 | .10** |
| Apheoline | K | -.597 | .01 | -.472 | .03 | -.236 | .17 |
| Apheoline | P | -.908 | .0001* | -.785 | .000 | -.382 | .06** |
| Apheoline | U | -.572 | .01* | -.86 | .000 | -.855 | .0002* |
| Apheoline | E | -.785 | .006* | -.927 | .000 | -.527 | .015* |
| Apheoline | K | -.917 | .00006 | -.85 | .000 | -.341 | .10** |
| Apheoline | N | -.774 | .0007* | -.88 | .000 | -.782 | .0005* |
| Apheoline | F | -.774 | .0007* | -.812 | .000 | .06 | .88 |
| Apheoline | G | -.112 | .35 | -.587 | .007 | -.33 | .09** |

*Downward trend significant at test size 0.05,
**downward trend significant at test size 0.1

Results for Subjects with Elevated Glucose and/or Insulin Levels

The levels of Glucose, C-Peptide and Insulin were plotted against time for a subset of the data set generated during testing, for which initial Glucose and/or Insulin levels are elevated. The levels of Glucose, C-Peptide and Insulin all return to normal for subjects taking any of the three Alpholine/Livea formulations [Alpholine/Livea-2, Alpholine/Livea-2, and Alpholine/Livea].

Weight Loss Associated with Positive Side Effects

FIG. 38 shows the total weight loss observed for a subject on Livea (50 year old female) as a function of days between measurements, and FIG. 39 shows levels of liver enzymes in the same patient at the times of measurements. For this subject, Livea clearly has a positive and significant effect on liver enzymes.

Discussion

Injection of analogue of GLP-1 peripherally is a familiar approach in the treatment of diabetes, and produces appetite suppression in a manner similar to Livea treatment. However, the properties of peripheral GLP-1 include a different distribution pattern and a short half life of approximately 3 minutes. The majority of the dose does not enter the portal system as it would if GLP-1 was induced by GI tract stimulation and with peripheral administration less than 15% will go through the liver to the periphery. While exogenous use of enteric ileal brake hormones is demonstrated to have an effect on appetite suppression, the idea of resetting the endogenous ileal brake in the lumen of the GI tract has not been tried before, other than by bariatric surgery. The ileal brake pathway is optimally activated LOCALLY in the distal small bowel, and when stimulated properly these ileal brake hormones act synergistically and in a highly complementary manner, which both avoids side effects associated with only one of them administered parenterally. The drawback to the peripheral injection approach of GLP-1, although proven to have appetite suppression, is partly a delivery site problem. For example, subcutaneous injection of GLP-1 mimetic, at supra-physiological levels, does not allow the advantages of portal application of lowered amounts. Thus the liver and pancreas effects are not beneficial; only the brain appetite suppression axis is activated. Furthermore there are GLP-1 receptors in non-target organs like the heart and kidney, and these may explain some of the recently noted side effects of Exenatide. Thus the portal system is where most of the action is taking place, and activation of the local ileal brake pathways lead to the full complement of benefits beyond appetite suppression. With oral administration of Aphoeline/Livea, there is appetite suppression, but also beneficial effects on glucose control, insulin pathways, re-set pancreatic glucose sensors, hepatic glycogen storage and glucose release, and mobilization of adipose tissue.

The actions controlled by Alphoeline/Livea are in the GI tract itself all the way from the esophagus to the rectum. Another problem with peripheral GLP-1 is the development of antibodies to the peptide within one year and up to 40% of the treated patients with Exenatide. The other side effects of Exenatide include pancreatitis and renal failure associated with the treatment.

On reviewing the literature in regard to appetite control and obesity the mainstream approach has been caloric counting and exercise. Excessive caloric intake has been linked to a psychological problem. As a consequence, from the patient viewpoint they are either addicted to food without will power or the patient is not sufficiently active to compensate for the intake of calories (49). Though valid, these statements do not give an accurate picture of the problem afflicting the large proportion of patients that appear to be very balanced psychologically and despite their best efforts are not capable of losing weight. Some reviews suggest that people under stress tend to lose less weight than people under less stressful situations, ascribing cortisol as the etiological factor. Other studies using a rat model (48) suggest that obesity is predetermined and one will tend to go back to the genetic curve with age.

We do know that certain conditions, including diabetes, hypertension, insulin resistance, commonly used antidepressants and anti-psychotics are associated with weight gain. The effect of bariatric surgery on patients with obesity and concomitant diabetes also seem to be mediated thru the suppression of appetite centrally after local GI activation of the ileal brake pathway. The mechanism of action is not psychological as oral caloric intake and energy expenditure, since patients with a bypass surgery for obesity have improved appetite control compared to people that undergo a lap band surgery. The effectiveness of bariatric surgery is also related to the connection site of the bypass. Make it too short and severe malabsorption results, while if the loop is too long the patient does not lose weight. Another consistent observation is the favorable weight loss action of LIRAGLUTIDE in spite of no major changes in patient behavior or lifestyle (29).

The other approach to the treatment of obesity is to try to bypass different systems like providing medications that work directly on the satiety center by different medications that are available on the market. The different side effects that will have to be dealt with include hypertension, stroke, addiction, seizures, cardiac arrhythmias and coronary events, pulmonary hypertension, severe depression, suicide, and insomnia. Even when the patient looses weight, there is a rebound off medications associated with binge eating and the patient ends up being either recycled in the system for another course of therapy in weight control centers, or gaining more weight than he started with, putting him at risk that could be higher than the baseline due to the severe weight fluctuations over short periods of time. Vildagliptin is a selective dipeptidyl peptidase IV inhibitor that augments meal-stimulated levels of biologically active glucagon-like peptide-1. Chronic Vildagliptin treatment decreases postprandial glucose levels and reduces hemoglobin A1C in type 2 diabetic patients. However, little is known about the mechanism(s) by which Vildagliptin promotes reduction in plasma glucose concentration. METHODS: Sixteen patients with type 2 diabetes (age, 48+/−3 yr; body mass index, 34.4+/−1.7 kg/m2; hemoglobin A1c, 9.0+/−0.3%) participated in a randomized, double-blind, placebo-controlled trial. On separate days patients received 100 mg Vildagliptin or placebo at 1730 h followed 30 min later by a meal tolerance test (MTT) performed with double tracer technique (3-(3)H-glucose iv and 1-(14)C-glucose orally). RESULTS: After Vildagliptin, suppression of endogenous glucose production (EGP) during 6-h MTT was greater than with placebo (1.02+/−0.06 vs. 0.74+/−0.06 mg·kg-1·min-1; P=0.004), and insulin secretion rate increased by 21% (P=0.003) despite significant reduction in mean plasma glucose (213+/−4 vs. 230+/−4 mg/dl; P=0.006). Consequently, insulin secretion rate (area under the curve) divided by plasma glucose (area under the curve) increased by 29% (P=0.01). Suppression of plasma glucagon during MTT was 5-fold greater with Vildagliptin (P<0.02). The decline in EGP was positively correlated (r=0.55; P<0.03) with the decrease in fasting plasma glucose (change=−14 mg/dl). CONCLUSIONS: During MTT, Vildagliptin augments insulin secretion and inhibits glucagon release, leading to enhanced suppression of EGP. During the postprandial period, a single dose of Vildagliptin reduced plasma glucose levels by enhancing suppression of EGP.(40)

Other approaches to weight loss target absorption, create states of malabsorption, produce stool incontinence, and may result in fatty liver and other undesirable effects (51).

Based on these premises leaders in the field started to emphasize a more natural GI tract based approach to weight loss that would involve all the endogenous mechanisms that regulate caloric intake and body weight. The goal was to lose more weight with fewer side effects, and the standard is Bariatric Surgery. A recent review of approaches to this problem eloquently summarizes the field (17, 41-44). The focus is shifting to the ileal brake pathways that are using the body natural signals: the gut hormones for future research of obesity pharmacotherapy (45, 46).

Based on our clinical observations, there is a component of hunger and obesity that is visceral and unconscious. To a certain extent, these effects are unknown to the patient, making it very difficult for the person to control appetite. The person at the time will be trying to replace the lack of visceral perception with an alternative voluntary conscious awareness resulting in continuous monitoring of the calories and input output as well as calories used and activity at all time to control the weight. This is difficult, and often causes frustration to those attempting to lose weight in this manner.

Low-glycemic index (GI) foods and foods rich in whole grain are associated with reduced risk of type 2 diabetes and cardiovascular disease. Nilsson and Holst examined the effect of cereal-based bread evening meals (50 g available starch) that varied in content of indigestible carbohydrates, on glucose tolerance and related variables after a subsequent standardized breakfast in healthy subjects (n=15). At breakfast, blood was sampled for 3 h for analysis of blood glucose, serum insulin, serum FFA, serum triacylglycerides, plasma glucagon, plasma gastric-inhibitory peptide, plasma glucagon-like peptide-1 (GLP-1), serum interleukin (IL)-6, serum IL-8, and plasma adiponectin. Satiety was subjectively rated after breakfast and the gastric emptying rate (GER) was determined using paracetamol as a marker. Breath hydrogen was measured as an indicator of colonic fermentation. Evening meals with barley kernel based bread (ordinary, high-amylose- or beta-glucan-rich genotypes) or an evening meal with white wheat flour bread (WWB) enriched with a mixture of barley fiber and resistant starch improved glucose tolerance at the subsequent breakfast compared with unsupplemented WWB (P<0.05). At breakfast, the glucose response was inversely correlated with colonic fermentation (r=−0.25; P<0.05) and GLP-1 (r=−0.26; P<0.05) and positively correlated with FFA (r=0.37; P<0.001). IL-6 was lower (P<0.01) and adiponectin was higher (P<0.05) at breakfast following an evening meal with barley-kernel bread compared with WWB. Breath hydrogen correlated positively with satiety (r=0.27; P<0.01) and inversely with GER (r=−0.23; P<0.05). The authors concluded from these experiments that composition of indigestible carbohydrates of the evening meal may affect glycemic excursions and related metabolic risk variables at breakfast through a mechanism involving colonic fermentation. The results provide evidence for a link between gut microbial metabolism and key factors associated with insulin resistance.(47)

Going back to the literature trying to figure out the different responses of the body to food between normal and overweight or obese patients, the only significant abnormality that was reported, is the response of the ileal break to the intake of the mixed meal (17, 22), and more specific to carbohydrates. Therefore it seems the natural satiety pathways become tolerant to the intake of carbohydrates. This partially explains the success of the Adkins diet, even though in this case there are no demonstrable differences in the anatomy or histology of those two groups, except in rare cases of severe morbid long term obesity associated with atrophy of the ileum. Given the fact that food delivered to that part of the intestine is capable of stimulating those hormones independently of oral intake and the fact that the ileal stimulation during a mixed meal can be inhibited by suppressing the neurotransmission raise the possibility that the problem seems to be about the transmission of the signal from gut to brain. It is possible that a reset of a carbohydrate tolerant ileal brake pathway will re-set the appetite center and renew the feedback loop that interrupts eating, all without progression to a metabolic syndrome. Therefore if we are able to directly stimulate the ileum we should be able to restore the ileal brake signal and at least give the patient some help in restoring visceral signals that measures the food intake.

These visceral signals are not only important to signal satiety but as per reported reviews (34, 44) these hormones are extremely beneficial to the patient. Their absence during down-regulation could be what the patient's are seeking unconsciously when they overeat, energy improve muscle, liver, intestine stomach, nerve and heart. Since these hormones are also very important in the homeostasis of the insulin and glucose levels they will help tremendously in the use is of the reserves that are already present.

By stimulating the hormones naturally with Alphoeline/Livea we are delivering the majority of the hormones where they belong in the portal system, where they have the most powerful impact on satiety. We were also encouraged by the fact that the bypass surgery for obesity is capable of stimulating those hormones in all patients, indicating that the innate ability of these hormones to respond is still present.

We set a goal to stimulate the ileal hormones with an oral natural agent consistent of a nutritional substance. The data are compelling and the stimulation of the ileal brake pathway seems independent of age or weight or diabetes. This establishes the intestine still functions despite obesity, and the problem seems to be in the down-regulation of the signaling from the ileum. (Another confirmation to that statement comes from the surgical bypass that in appropriate individual triggers the same process).

What we discovered from these stimulation that it have a very powerful effect on the glucose and insulin homeostasis not consistent with the assumption that these peptides work only by stimulation of the insulin but mainly through reducing insulin resistance as well long before they achieve weight loss. This is also consistent with the data from bypass surgery.

The more powerful effect on steato-hepatitis seen by decrease of the enzymes level to normal within 3-4 weeks need to be studied on a much longer duration to confirm the trend and the gains, but it seems from the energy, satiety and the trend to normalize triglyceride and cholesterol as well as to the satiety factors and surprising improvement of all parameters including platelets that the trend is true. Similar platelets trend is seen in cirrhotic patients (non-published data).

Based on the recent publication of Lirutaglide and weight loss(29), the GLP-1 family of gut hormones will induce weight loss but in a different way than expected, the weight loss is slow and happens after other parameters start to improve. Weight loss is insidious, just like weight gain, and occurs on a rather unconscious level. The pathway is re-activated after being dormant and the distal caloric signals are now once again responded to in the ileum.

The advantage of having an oral stimulation of all the ileal hormones is the synergistic effect of the hormones that were meant to be stimulated together in a broad pathway beyond any individual component. The fact that these hormones are released in the portal system that seems to be the center of all metabolism except the muscles and the brain, the fact that the highest concentration of these hormones is in the portal system make our stimulation much less intrusive and more efficient than the peripheral administration of such hormones.

The suppression of insulin resistance need further investigation even though we showed that the IGF system is stimulated, we do not feel this is the only answer to the question; other peptides as well as other cellular receptors such as the RR receptors need to be investigated as part of the equation. In the next section, we prioritize our future work in this direction.

The Stimulation of the Ileal Hormones with Livea: Present Opportunities and Challenges.

1. A continuing priority is to improve the ileal brake stimulation potency with further adjustments of the formulation content and the ileal delivery system.
2. Another priority is to develop more practical tests to document the anticipated down-regulation of the ileal brake pathway in the obese, and to demonstrate the impact of Aphoeline in the resetting of this pathway. This testing should be applied to study of a variety of GI diseases such as irritable bowel, and to examine the relationships between hormones and intestinal permeability, immune system and bacterial flora.
3. Third priority is to check on the long term effects of the oral stimulation on improving muscles, pancreas, suppression of acid of the stomach as reported, and determine if the epidemic of reflux and adenocarcinoma increase could be explained on the basis of these hormones deficiency or abnormal responses as reported PYY and GLP1 inhibit together gastric acid secretion 100%.
4. It is necessary to examine the effects of Aphoeline on GI motility including the esophagus and achalasia since these hormones were reported to be neurotrophic. The effect on the lung has not been studied yet, but since it improves the function of other muscles it should have a beneficial impact on the costal muscles, as well as those of the bronchi and the diaphragm.
5. Diabetes is a major target and its innocuous profile should be considered as a first line of treatment, large study and long term effect should be targeted including HbA1c, all indications that the ileal brake pathway does improve diabetes. Because of its effect on insulin resistance, other circumstances of insulin resistance should be checked as well including but not limited to polycystic ovaries.
6. We also would study the effect on the liver. Even though it helps fatty liver it seems that it effect should be checked in different conditions as well including different hepatitis as a co-adjuvant therapy.
7. We would also investigate the use of Aphoeline as a co-adjuvant therapy in bypass surgery. Assessment of action prior to surgery to study the ileal response or to stabilize the patient and improve their gut or post op as a salvage therapy, or co-adjuvant, should be considered.

The to-do list and the excitement are limitless, especially considering that these effects were produced by a benign orally administered natural product. Reactivation of a dormant gut peptide mechanism is a means of examining the gut as well as obesity from a new perspective.

Summary

We have demonstrated the feasibility of a benign food substance delivered orally to stimulate the ileal hormones. The response appears to be sufficient to standardize the stimulation of the ileal brake hormones. Some unusual effects of that stimulation included suppression of insulin resistance, improvement in blood glucose levels, and significant early improvement in liver enzymes and lipid levels. While these beneficial effects were sustained in short term experiments, further large scale clinical testing and longer term clinical studies will be needed to confirm the persistence of these effects.

Based on our open trials, the long term effect of the Aphoeline formulation is an increase in energy levels. There was an unconscious awareness of the calorie intake and a resetting of appetite which then resulted in significant weight loss. Long term double-blind placebo controlled trials, similar to the one conducted with Liraglutide, are being planned.

Longer Term Studies

A number of patients above were followed for six months to a year period following the initial studies described above (therapy continued at 7 pills—about 10 g. glucose per day via Aphoeline-2 with blood work performed weekly) to determine what effects would be present or manifest during that time period. The following results and general trends were obtained and/or observed:

1. Insulin resistance continued to be suppressed;
2. Insulin, pro-insulin and c-peptide were brought back to normal levels;
3. Patient's weight decreased substantially;
4. Decreased triglyceride levels to normal (from 400 mg/dl to about 100-120 mg/dl);
5. Decrease liver enzymes from about 300 IU/L down to a normal level (0-85 IU/L);
6. Decreased hepatitis C-virus titers.
7. Substantially decreased $\alpha$-fetal protein (from 30 ng/ml to less than 6 ng/m.).

The effects of the present invention are long-lasting and therapy may be continued for extended periods of time, resulting in favorable responses in all patients tested.

The terms and expressions that have been employed in this application are used as terms of description and not of limitation, and there is no intent in the use of such terms and expressions to exclude any equivalent of the features shown and described or portions thereof, but it is recognized that various modifications are possible within the scope of the invention as claimed.

Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

REFERENCES

1. Polak J M, Bloom S, Coulling I, Pearse A G. Immunofluorescent localization of enteroglucagon cells in the gastrointestinal tract of the dog. *Gut.* 1971; 12(4):311-8.
2. Polak J M, Coulling I, Bloom S, Pearse A G. Immunofluorescent localization of secretin and enteroglucagon in human intestinal mucosa. *Scand J Gastroenterol.* 1971; 6(8):739-44.
3. Maljaars P W, Peters H P, Mela D J, Masclee A A. Ileal brake: a sensible food target for appetite control. A review. *Physiol Behav.* 2008; 95(3):271-81.
4. Van Citters G W, Lin H C. Ileal brake: neuropeptidergic control of intestinal transit. *Curr Gastroenterol Rep.* 2006; 8(5):367-73.
5. Schirra J, Goke B. The physiological role of GLP-1 in human: incretin, ileal brake or more? *Regul Pept.* 2005; 128(2):109-15.
6. Dobson C L, Davis S S, Chauhan S, Sparrow R A, Wilding I R. The effect of ileal brake activators on the oral bioavailability of atenolol in man. *Int J Pharm.* 2002; 248(1-2):61-70.
7. Van Citters G W, Lin H C. The ileal brake: a fifteen-year progress report. *Curr Gastroenterol Rep.* 1999; 1(5):404-9.
8. Vu M K, Nouwens M A, Biemond I, Lamers C B, Masclee A A. The osmotic laxative magnesium sulphate activates the ileal brake. *Aliment Pharmacol Ther.* 2000; 14(5):587-95.
9. Dobson C L, Davis S S, Chauhan S, Sparrow R A, Wilding I R. The effect of oleic acid on the human ileal brake and its implications for small intestinal transit of tablet formulations. *Pharm Res.* 1999; 16(1):92-6.
10. Pironi L, Stanghellini V, Miglioli M, et al. Fat-induced ileal brake in humans: a dose-dependent phenomenon correlated to the plasma levels of peptide YY. *Gastroenterology.* 1993; 105(3):733-9.
11. Soper N J, Chapman N J, Kelly K A, Brown M L, Phillips S F, Go V L. The 'ileal brake' after ileal pouch-anal anastomosis. *Gastroenterology.* 1990; 98(1):111-6.
12. Spiller R C, Trotman I F, Adrian T E, Bloom S R, Misiewicz J J, Silk D B. Further characterisation of the 'ileal brake' reflex in man—effect of ileal infusion of partial digests of fat, protein, and starch on jejunal motility and release of neurotensin, enteroglucagon, and peptide YY. *Gut.* 1988; 29(8):1042-51.
13. Milk fat, diarrhoea, and the ileal brake. *Lancet.* 1986; 1(8482):658.
14. Spiller R C, Trotman I F, Higgins B E, et al. The ileal brake—inhibition of jejunal motility after ileal fat perfusion in man. *Gut.* 1984; 25(4):365-74.
15. Tamburrano G, Mauceri M, Lala A, Tonelli F, Leonetti F, Andreani D. Plasma levels of glucagon-like polypeptides in gastrectomized patients transformed from Billroth II into Billroth I. *Horm Metab Res.* 1982; 14(12):642-5.
16. Tamburrano G, F. Tonelli, A. Lala, M. Mauceri, J. Fayad and D. Andreani, Plasma Levels of Extrapancreatic Glucagon (GLI) and Nesidioglucagon (IRG) in Patients with Esophagoplasty *International Symposium on Hypoglycemia*, p. 493, *Serono*publi., Rome, 1980.
17. Hoist J J. Glucagonlike peptide 1: a newly discovered gastrointestinal hormone. *Gastroenterology.* 1994; 107(6):1848-55.
18. Hoist J J, Bersani M, Johnsen A H, Kofod H, Hartmann B, Orskov C. Proglucagon processing in porcine and human pancreas. *J Biol Chem.* 1994; 269(29):18827-33.
19. Williams D L. Minireview: finding the sweet spot: peripheral versus central glucagon-like peptide 1 action in feeding and glucose homeostasis. *Endocrinology.* 2009; 150(7):2997-3001.
20. Fields A V, Patterson B, Karnik A A, Shannon R P. Glucagon-like peptide-1 and myocardial protection: more than glycemic control. *Clin Cardiol.* 2009; 32(5):236-43.
21. Abu-Hamdah R, Rabiee A, Meneilly G S, Shannon R P, Andersen D K, Elahi D. Clinical review: The extrapancreatic effects of glucagon-like peptide-1 and related peptides. *J Clin Endocrinol Metab.* 2009; 94(6):1843-52.
22. Ranganath L R, Beety J M, Morgan L M, Wright J W, Howland R, Marks V. Attenuated GLP-1 secretion in obesity: cause or consequence? *Gut.* 1996; 38(6):916-9.
23. Field B C, Wren A M, Cooke D, Bloom S R. Gut hormones as potential new targets for appetite regulation and the treatment of obesity. *Drugs.* 2008; 68(2):147-63.
24. Jayasena C N, Bloom S R. Role of gut hormones in obesity. *Endocrinol Metab Clin North Am.* 2008; 37(3): 769-87, xi.
25. Damholt A B, Buchan A M, Kofod H. Glucagon-like-peptide-1 secretion from canine L-cells is increased by glucose-dependent-insulinotropic peptide but unaffected by glucose. *Endocrinology.* 1998; 139(4):2085-91.
26. Hoist J J. The physiology of glucagon-like peptide 1. *Physiol Rev.* 2007; 87(4):1409-39.
27. Gutzwiller J P, Drewe J, Goke B, et al. Glucagon-like peptide-1 promotes satiety and reduces food intake in patients with diabetes mellitus type 2. *Am J. Physiol.* 1999; 276(5 Pt 2):R1541-4.
28. Gutzwiller J P, Goke B, Drewe J, et al. Glucagon-like peptide-1: a potent regulator of food intake in humans. *Gut.* 1999; 44(1):81-6.
29. Astrup A, Rossner S, Van Gaal L, et al. Effects of liraglutide in the treatment of obesity: a randomised, double-blind, placebo-controlled study. *Lancet.* 2009; 374 (9701):1606-16.
30. Peters C T, Choi Y H, Brubaker P L, Anderson G H. A glucagon-like peptide-1 receptor agonist and an antagonist modify macronutrient selection by rats. *J Nutr.* 2001; 131(8):2164-70.
31. Choi Y H, Anderson G H. An interaction between hypothalamic glucagon-like peptide-1 and macronutrient composition determines food intake in rats. *J. Nutr.* 2001; 131(6):1819-25.
32. Burcelin R, Da Costa A, Drucker D, Thorens B. Glucose competence of the hepatoportal vein sensor requires the presence of an activated glucagon-like peptide-1 receptor. *Diabetes.* 2001; 50(8):1720-8.
33. Drucker D J. Development of glucagon-like peptide-1-based pharmaceuticals as therapeutic agents for the treatment of diabetes. *Curr Pharm Des.* 2001; 7(14):1399-412.
34. Drucker D J. Glucagon-like peptide 2. *J Clin Endocrinol Metab.* 2001; 86(4):1759-64.
35. Lovshin J, Estall J, Yusta B, Brown T J, Drucker D J. Glucagon-like peptide (GLP)-2 action in the murine central nervous system is enhanced by elimination of GLP-1 receptor signaling. *J Biol Chem.* 2001; 276(24):21489-99.
36. Boushey R P, Yusta B, Drucker D J. Glucagon-like peptide (GLP)-2 reduces chemotherapy-associated mortality and enhances cell survival in cells expressing a transfected GLP-2 receptor. *Cancer Res.* 2001; 61(2):687-93.
37. Drucker D J. Minireview: the glucagon-like peptides. *Endocrinology.* 2001; 142(2):521-7.

38. Adrian T E, Savage A P, Fuessl H S, Wolfe K, Besterman H S, Bloom S R. Release of peptide YY (PYY) after resection of small bowel, colon, or pancreas in man. *Surgery.* 1987; 101(6):715-9.
39. Savage A P, Adrian T E, Carolan G, Chatterjee V K, Bloom S R. Effects of peptide YY (PYY) on mouth to caecum intestinal transit time and on the rate of gastric emptying in healthy volunteers. *Gut.* 1987; 28(2):166-70.
40. Balas B, Baig M R, Watson C, et al. The dipeptidyl peptidase IV inhibitor vildagliptin suppresses endogenous glucose production and enhances islet function after single-dose administration in type 2 diabetic patients. *J Clin Endocrinol Metab.* 2007; 92(4):1249-55.
41. Qualmann C, Nauck M A, Holst J J, Orskov C, Creutzfeldt W. Insulinotropic actions of intravenous glucagon-like peptide-1 (GLP-1) [7-36 amide] in the fasting state in healthy subjects. *Acta Diabetol.* 1995; 32(1):13-6.
42. Hoist J J. Glucagon-like peptide-1, a gastrointestinal hormone with a pharmaceutical potential. *Curr Med Chem.* 1999; 6(11):1005-17.
43. Meier J J, Gallwitz B, Salmen S, et al. Normalization of glucose concentrations and deceleration of gastric emptying after solid meals during intravenous glucagon-like peptide 1 in patients with type 2 diabetes. *J Clin Endocrinol Metab.* 2003; 88(6):2719-25.
44. Baynes K C, Dhillo W S, Bloom S R. Regulation of food intake by gastrointestinal hormones. *Curr Opin Gastroenterol.* 2006; 22(6):626-31.
45. Chaudhri O B, Wynne K, Bloom S R. Can gut hormones control appetite and prevent obesity? *Diabetes Care.* 2008; 31 Suppl 2:S284-9.
46. Chaudhri O, Small C, Bloom S. Gastrointestinal hormones regulating appetite. *Philos Trans R Soc Lond B Biol Sci.* 2006; 361(1471):1187-209.
47. Nilsson A C, Ostman E M, Holst J J, Bjorck I M. Including indigestible carbohydrates in the evening meal of healthy subjects improves glucose tolerance, lowers inflammatory markers, and increases satiety after a subsequent standardized breakfast. *J Nutr.* 2008; 138(4):732-9.
48. Maclean P S, Energy balance with weight loss and relapse Am. J. Physiology, 2004.
49. Thomas A. Warden, et al. One year weight losses in the look ahead study: Factors associated with success. Obesity (2009) 17, 713-722.
50. *FDA COMMUNICATION* Aug. 24, 2009 *Early Communication about an Ongoing Safety Review Orlistat (marketed as Alli and Xenical).*
51. Hipel, K W. & McLeod, A. I. (2005). *Time Series Modeling of Water Resources and Environmental Systems.*
52. Computing, Vienna, Austria. R Development Core Team (2009).
   R: A language and environment for statistical computing. R Foundation for Statistica ISBN 3-900051-07-0, URL http://www.R-project.org.

The invention claimed is:
1. A method of treating insulin resistance including insulin resistance associated with noninsulin dependent diabetes mellitus (type II diabetes) in a human patient or subject in need thereof comprising administering to said patient or subject D-glucose in oral dosage form, said oral dosage form releasing an ileal hormone stimulating effective amount of said glucose in the ileum of said patient or subject after oral administration, said glucose released in said ileum causing a release of ileal hormones effective to reduce insulin resistance in said patient or subject within about 3 to 10 hours after administration.

2. The method according to claim 1 wherein said oral dosage form is in sustained/controlled release form which releases a majority of said D-glucose upon reaching the ileum of said patient or subject to stimulate said ileal hormones.

3. The method according to claim 1 wherein said oral dosage form further comprises one or more further component selected from the group consisting of alfalfa leaf, chlorella algae, chlorophyllin and barley grass juice concentrate, and said oral dosage form is a delayed or controlled release form adapted to release at least 50% by weight of said D-glucose and said further component upon reaching the ileum.

4. The method according to claim 1 wherein said oral dosage form is enteric coated.

5. The method according to claim 1 wherein said oral dosage form releases an effective amount of D-glucose in the ileum of said patient or subject of at least about 5 grams.

6. The method according to claim 1 wherein said oral dosage form releases an effective amount of D-glucose in the ileum of said patient or subject ranging from about 7.5 grams to about 20 grams.

7. The method according to claim 1 wherein said oral dosage form releases an effective amount of D-glucose in the ileum of said patient or subject ranging from about 7.5 grams to about 12.5 grams.

8. The method according to claim 1 wherein said oral dosage form releases an effective amount of D-glucose in the ileum of said patient or subject in an amount of about 7.5 to about 10 grams.

9. The method according to claim 1, wherein said oral dosage form comprises a substance core comprising D-glucose and an enterically-coated tablet or a hard or soft capsule.

10. The method according to claim 1, wherein said oral dosage form is made by coating the D-glucose with a material which has a pH dissolution or time delayed profile that delays the release of the majority of the D-glucose until the dosage form reaches the patient's or subject's ileum.

11. The method according to claim 5, wherein said oral dosage form is made by coating the D-glucose with a material which has a pH dissolution or time delayed profile that delays the release of the majority of the D-glucose until the dosage form reaches the patient's or subject's ileum.

12. The method according to claim 7, wherein said oral dosage form is made by coating the D-glucose with a material which has a pH dissolution or time delayed profile that delays the release of the majority of the D-glucose until the dosage form reaches the patient's or subject's ileum.

13. The method according claim 10, wherein said material having a pH dissolution profile that delays release is selected from the group consisting of cellulose acetate trimellitate (CAT), hydroxypropylmethyl cellulose phthalate (HPMCP), hydroxypropylmethyl cellulose, ethyl cellulose, color con, food glaze and mixtures of hydroxypropylmethyl cellulose and ethyl cellulose each of which contains a subcoating, polyvinyl acetate phthalate (PVAP), cellulose acetate phthalate (CAP), shellac, copolymers of methacrylic acid and ethyl acrylate, and copolymers of methacrylic acid and ethyl acrylate to which a monomer of methylacrylate has been added during polymerization.

14. The method according claim 11, wherein said material having a pH dissolution profile that delays release is selected from the group consisting of cellulose acetate trimellitate (CAT), hydroxypropylmethyl cellulose phthalate (HPMCP), hydroxypropylmethyl cellulose, ethyl cellulose, color con, food glaze and mixtures of hydroxypropylmethyl cellulose and ethyl cellulose each of which contains a subcoating, polyvinyl acetate phthalate (PVAP), cellulose acetate phthalate (CAP), shellac, copolymers of methacrylic acid and ethyl acrylate, and copolymers of methacrylic acid and ethyl acrylate to which a monomer of methylacrylate has been added during polymerization.

15. The method according claim 12, wherein said material having a pH dissolution profile that delays release is selected from the group consisting of cellulose acetate trimellitate (CAT), hydroxypropylmethyl cellulose phthalate (HPMCP), hydroxypropylmethyl cellulose, ethyl cellulose, color con, food glaze and mixtures of hydroxypropylmethyl cellulose and ethyl cellulose each of which contains a subcoating, polyvinyl acetate phthalate (PVAP), cellulose acetate phthalate (CAP), shellac, copolymers of methacrylic acid and ethyl acrylate, and copolymers of methacrylic acid and ethyl acrylate to which a monomer of methylacrylate has been added during polymerization.

16. The method according to claim 10, wherein the D-glucose is coated with shellac.

17. The method according to claim 11, wherein the D-glucose is coated with shellac.

18. The method according to claim 12, wherein the D-glucose is coated with shellac.

19. The method according to claim 16 wherein said shellac is about 4-8% by weight of said composition.

20. The method according to claim 16 wherein said shellac is about 4-8% by weight of said composition.

21. The method according to claim 16 wherein said shellac is about 4-8% by weight of said composition.

22. The method according to claim 1 wherein said oral dosage form comprises individual oral doses of 1429 mg. of D-glucose, each of said oral doses further comprising 3.00 mg. Alfalfa leaf, 3.00 mg. Chlorella Algae, 3.00 mg. Chlorophyllin and 3.00 mg. Barley Grass Juice Concentrate, 3.00 mg.

23. The method according to claim 1, wherein the oral dosage form comprises a substance core comprising D-glucose.

24. The method according to claim 23, wherein the substance core of D-glucose is enterically coated.

25. The method of claim 1, wherein said oral dosage form is a delayed and/or controlled release dosage form formed by coating the D-glucose with a shellac coating, optionally including an emulsifier.

26. The method according to claim 1, wherein the amount of said D-glucose administered to said patient or subject is adjusted after measuring the patient's or subject's ileal hormone release to said administration.

27. The method according to claim 5, wherein the amount of said D-glucose administered to said patient or subject is adjusted after measuring the patient's ileal hormone release to said administration.

28. The method according to claim 7, wherein the amount of said D-glucose administered to said patient or subject is adjusted after measuring the patient's ileal hormone release to said administration.

29. The method according to claim 26 wherein measuring said ileal hormone release comprises monitoring the patient's or subject's blood levels of one or more of the following: GLP-1, GLP-2, PYY, C-peptide, blood sugar, insulin, and glucagon after a period of fasting.

30. The method according to claim 27 wherein measuring said ileal hormone release comprises monitoring the patient's or subject's blood levels of one or more of the following: GLP-1, GLP-2, PYY, C-peptide, blood sugar, insulin, and glucagon after a period of fasting.

31. The method according to claim 28 wherein measuring said ileal hormone release comprises monitoring the patient's or subject's blood levels of one or more of the following: GLP-1, GLP-2, PYY, C-peptide, blood sugar, insulin, and glucagon after a period of fasting.

32. The method according to claim 1 comprising measuring one or more of the patient's or subject's levels of at least GLP-1, PYY and insulin.

33. The method according to claim 7 further comprising measuring one or more of the patient's or subject's levels of GLP-1, PYY and insulin.

34. The method according to claim 27 further comprising measuring one or more of the patient's or subject's levels of GLP-1, PPY, insulin, IGF-1 and IGF-2.

35. The method according to claim 28 further comprising measuring one or more of the patient's or subject's levels of IGF-1, IGF-2 or mixtures thereof.

36. The method according to claim 1 wherein said release of hormones effects a change in insulin resistance and insulin concentration which is proportional to said patient's or subject's insulin and/or blood sugar levels.

37. The method according to claim 1 wherein said ileal hormones are released about 4 hours to 10 hours after administration.

38. The method according to claim 5 wherein said release of hormones effects a change in insulin resistance and insulin concentration which is proportional to said patient's or subject's insulin and/or blood sugar levels.

39. The method according to claim 5 wherein said ileal hormones are released about 4 hours to 10 hours after administration.

40. The method according to claim 7 wherein said release of hormones effects a change in insulin resistance and insulin concentration which is proportional to said patient's or subject's insulin and/or blood sugar levels.

41. The method according to claim 7 wherein said ileal hormones are released about 4 hours to 10 hours after administration.

42. The method according to claim 1 wherein plasma glucose levels of said patient or subject are reduced and/or stabilized about 4 hours to 10 hours after administration of said D-glucose.

43. The method according to claim 5 wherein plasma glucose levels of said patient or subject are reduced and/or stabilized about 4 hours to 10 hours after administration of said D-glucose.

44. The method according to claim 7 wherein plasma glucose levels of said patient or subject are reduced and/or stabilized about 4 hours to 10 hours after administration of said D-glucose.

45. The method according to claim 1, wherein said oral dosage form further comprises a plant or animal oil, an animal or vegetable fat, caffeine, an herb, tea or a mixture thereof.

46. The method according to claim 3, wherein said oral dosage form further comprises a plant or animal oil, an animal or vegetable fat, caffeine, an herb, tea or a mixture thereof.

47. The method according to claim 5, wherein said oral dosage form further comprises a plant or animal oil, an animal or vegetable fat, caffeine, an herb, tea or a mixture thereof.

48. The method according to claim 7, wherein said oral dosage form further comprises a plant or animal oil, an animal or vegetable fat, caffeine, an herb, tea or a mixture thereof.

49. A method of treating insulin resistance in a human patient or subject in need thereof, comprising administering to said patient or subject D-glucose in oral dosage form, said oral dosage form releasing an ileal hormone stimulating effective amount of said glucose in the ileum of said patient or subject after oral administration, said glucose released in said ileum causing a release of ileal hormones effective to reduce insulin resistance by lowering the elevated blood glucose and blood insulin levels in said patient or subject to normal or close to normal levels.

50. A method of treating insulin resistance in a human patient or subject including a patient or subject with non-insulin dependent diabetes mellitus (type II diabetes) in need thereof, comprising administering to said patient or subject D-glucose in oral dosage form, said oral dosage form releasing an ileal hormone stimulating effective amount of said glucose in the ileum of said patient or subject after oral administration, whereby said glucose released in said ileum stimulates a dormant ileal brake pathway thereby causing a release of ileal hormones into the portal system of said patient or subject effective to reduce insulin resistance by stabilizing said patient's or subject's blood sugar and insulin levels within normal or close to normal ranges (normalizing) within a period ranging from about 3 hours to about 10 hours after administration of said glucose, wherein said ileal hormones comprise effective amounts of PYY and GLP-1.

51. A method of treating insulin resistance in a human patient or subject in need thereof because said patient exhibits elevated blood levels of glucose and insulin compared to normal levels, comprising administering to said patient or subject D-glucose in oral dosage form, said oral dosage form releasing an ileal hormone stimulating effective amount of said glucose in the ileum of said patient or subject after oral administration, whereby said glucose released in said ileum stimulates a dormant ileal brake pathway thereby causing a release of ileal hormones into the portal system of said patient or subject effective to simultaneously reduce insulin resistance by reducing and/or stabilizing said patient's or subject's elevated blood sugar and blood insulin levels to normal or close to normal ranges within a period ranging from about 3 hours to about 10 hours after administration of said glucose.

52. A method of treating insulin resistance in a human patient or subject exhibiting elevated levels of blood glucose and blood insulin compared to normal levels, comprising administering to said patient or subject D-glucose in oral dosage form, said oral dosage form releasing an ileal hormone stimulating effective amount of said glucose in the ileum of said patient or subject after oral administration, whereby said glucose released in said ileum causes a release of ileal hormones into the portal system of said patient or subject effective to reduce insulin resistance by simultaneously reducing and/or stabilizing said patient's or subject's elevated blood sugar and blood insulin levels to normal or close to normal ranges within a period ranging from about 3 hours to about 10 hours after administration of said glucose, wherein said ileal hormones comprise effective amounts of PYY and GLP-1.

53. A method of treating insulin resistance in a human patient or subject including a patient or subject with non-insulin dependent diabetes mellitus (type II diabetes) in need thereof, comprising administering to said patient or subject D-glucose in oral dosage form, said oral dosage form releasing an ileal hormone stimulating effective amount of said glucose in the ileum of said patient or subject after oral administration, whereby said glucose released in said ileum causes a release of ileal hormones within the portal system of said patient or subject effective to treat insulin resistance by reducing and/or stabilizing said patient's or subject's elevated (compared to normal) blood sugar and blood insulin levels within normal or close to normal ranges within a period ranging from about 3 hours to about 10 hours after administration of said glucose.

54. The method according to claim 49 wherein said oral dosage form is in sustained/controlled release form which releases a majority of said D-glucose upon reaching the ileum of said patient or subject to stimulate said ileal hormones.

55. The method according to claim 54 wherein said oral dosage form is enteric coated.

56. The method according to claim 49 wherein said oral dosage form releases an effective amount of D-glucose in the ileum of said patient or subject ranging from about 7.5 grams to about 20 grams.

57. The method according to claim 49 wherein said oral dosage form releases an effective amount of D-glucose in the ileum of said patient or subject ranging from about 7.5 grams to about 12.5 grams.

58. The method according to claim 49, wherein said oral dosage form is made by coating the D-glucose with a material which has a pH dissolution or time delayed profile that delays the release of the majority of the D-glucose until the dosage form reaches the patient's or subject's ileum.

59. The method according claim 58, wherein said material having a pH dissolution profile that delays release is selected from the group consisting of cellulose acetate trimellitate (CAT), hydroxypropylmethyl cellulose phthalate (HPMCP), hydroxypropylmethyl cellulose, ethyl cellulose, color con, food glaze and mixtures of hydroxypropylmethyl cellulose and ethyl cellulose each of which contains a subcoating, polyvinyl acetate phthalate (PVAP), cellulose acetate phthalate (CAP), shellac, copolymers of methacrylic acid and ethyl acrylate, and copolymers of methacrylic acid and ethyl acrylate to which a monomer of methylacrylate has been added during polymerization.

60. The method according to claim 58, wherein the D-glucose is coated with shellac.

61. The method according to claim 60 wherein said shellac is about 4-8% by weight of said composition.

62. The method according to claim 49 wherein said oral dosage form comprises individual oral doses of 1429 mg. of D-glucose, each of said oral doses further comprising 3.00 mg. Alfalfa leaf, 3.00 mg. Chlorella Algae, 3.00 mg. Chlorophyllin and 3.00 mg. Barley Grass Juice Concentrate, 3.00 mg.

63. The method according to claim 49, wherein the oral dosage form comprises an enterically coated substance core comprising D-glucose.

64. The method according to claim 49, wherein the amount of said D-glucose administered to said patient or subject is adjusted after measuring the patient's or subject's ileal hormone release to said administration.

65. The method according to claim 64 wherein said measuring said ileal hormone release comprises monitoring the patient's or subject's blood levels of one or more of the following: GLP-1, GLP-2, PYY, C-peptide, blood sugar, insulin, and glucagon after a period of fasting.

66. The method according to claim 65 comprising measuring one or more of the patient's or subject's levels of at least GLP-1, PYY and insulin.

67. The method according to claim 49 wherein said release of hormones effects a reduction in insulin resistance by lowering and/or stabilizing blood glucose and blood insulin concentrations proportional to said patient's or subject's insulin and/or blood sugar levels.

68. The method according to claim 67 wherein said reduction in insulin resistance occurs within a period of about 3 hours to 10 hours after administration of said glucose.

69. The method according to claim 49, wherein said oral dosage form further comprises a plant or animal oil, an animal or vegetable fat, caffeine, an herb, tea or a mixture thereof.

70. The method according to claim 67, wherein said oral dosage form further comprises a plant or animal oil, an animal or vegetable fat, caffeine, an herb, tea or a mixture thereof.

71. The method according to claim 50 wherein said oral dosage form is in sustained/controlled release form which releases a majority of said D-glucose upon reaching the ileum of said patient or subject to stimulate said ileal hormones.

72. The method according to claim 71 wherein said oral dosage form is enteric coated.

73. The method according to claim 50 wherein said oral dosage form releases an effective amount of D-glucose in the ileum of said patient or subject ranging from about 7.5 grams to about 20 grams.

74. The method according to claim 50 wherein said oral dosage form releases an effective amount of D-glucose in the ileum of said patient or subject ranging from about 7.5 grams to about 12.5 grams.

75. The method according to claim 50, wherein said oral dosage form is made by coating the D-glucose with a material which has a pH dissolution or time delayed profile that delays the release of the majority of the D-glucose until the dosage form reaches the patient's or subject's ileum.

76. The method according claim 75, wherein said material having a pH dissolution profile that delays release is selected from the group consisting of cellulose acetate trimellitate (CAT), hydroxypropylmethyl cellulose phthalate (HPMCP), hydroxypropylmethyl cellulose, ethyl cellulose, color con, food glaze and mixtures of hydroxypropylmethyl cellulose and ethyl cellulose each of which contains a subcoating, polyvinyl acetate phthalate (PVAP), cellulose acetate phthalate (CAP), shellac, copolymers of methacrylic acid and ethyl acrylate, and copolymers of methacrylic acid and ethyl acrylate to which a monomer of methylacrylate has been added during polymerization.

77. The method according to claim 75, wherein the D-glucose is coated with shellac.

78. The method according to claim 77 wherein said shellac is about 4-8% by weight of said composition.

79. The method according to claim 50 wherein said oral dosage form comprises individual oral doses of 1429 mg. of D-glucose, each of said oral doses further comprising 3.00 mg. Alfalfa leaf, 3.00 mg. Chlorella Algae, 3.00 mg. Chlorophyllin and 3.00 mg. Barley Grass Juice Concentrate, 3.00 mg.

80. The method according to claim 50, wherein the oral dosage form comprises an enterically coated substance core comprising D-glucose.

81. The method according to claim 50, wherein the amount of said D-glucose administered to said patient or subject is adjusted after measuring the patient's or subject's ileal hormone release to said administration.

82. The method according to claim 81 wherein said measuring said ileal hormone release comprises monitoring the patient's or subject's blood levels of one or more of the following: GLP-1, GLP-2, PYY, C-peptide, blood sugar, insulin, and glucagon after a period of fasting.

83. The method according to claim 82 comprising measuring one or more of the patient's or subject's levels of at least GLP-1, PYY and insulin.

84. The method according to claim 50, wherein said oral dosage form further comprises a plant or animal oil, an animal or vegetable fat, caffeine, an herb, tea or a mixture thereof.

85. The method according to claim 72, wherein said oral dosage form further comprises a plant or animal oil, an animal or vegetable fat, caffeine, an herb, tea or a mixture thereof.

86. The method according to claim 51 wherein said oral dosage form is in sustained/controlled release form which releases a majority of said D-glucose upon reaching the ileum of said patient or subject to stimulate said ileal hormones.

87. The method according to claim 86 wherein said oral dosage form is enteric coated.

88. The method according to claim 51 wherein said oral dosage form releases an effective amount of D-glucose in the ileum of said patient or subject ranging from about 7.5 grams to about 20 grams.

89. The method according to claim 51 wherein said oral dosage form releases an effective amount of D-glucose in the ileum of said patient or subject ranging from about 7.5 grams to about 12.5 grams.

90. The method according to claim 51, wherein said oral dosage form is made by coating the D-glucose with a material which has a pH1 dissolution or time delayed profile that delays the release of the majority of the D-glucose until the dosage form reaches the patient's or subject's ileum and the material is shellac.

91. The method according to claim 51, wherein said oral dosage form further comprises a plant or animal oil, an animal or vegetable fat, caffeine, an herb, tea or a mixture thereof.

92. The method according to claim 52 wherein said oral dosage form is in sustained/controlled release form which releases a majority of said D-glucose upon reaching the ileum of said patient or subject to stimulate said ileal hormones.

93. The method according to claim 92 wherein said oral dosage form is enteric coated.

94. The method according to claim 52 wherein said oral dosage form releases an effective amount of D-glucose in the ileum of said patient or subject ranging from about 7.5 grams to about 20 grams.

95. The method according to claim 52, wherein said oral dosage form is made by coating the D-glucose with a material which has a pH dissolution or time delayed profile that delays the release of the majority of the D-glucose until the dosage form reaches the patient's or subject's ileum and the material is shellac.

96. The method according to claim 52, wherein said oral dosage form further comprises a plant or animal oil, an animal or vegetable fat, caffeine, an herb, tea or a mixture thereof.

97. The method according to claim 53 wherein said oral dosage form is in sustained/controlled release form which releases a majority of said D-glucose upon reaching the ileum of said patient or subject to stimulate said ileal hormones.

98. The method according to claim 92 wherein said oral dosage form is enteric coated.

99. The method according to claim 53 wherein said oral dosage form releases an effective amount of D-glucose in the ileum of said patient or subject ranging from about 7.5 grams to about 20 grams.

100. The method according to claim 53, wherein said oral dosage form is made by coating the D-glucose with a material which has a pH dissolution or time delayed profile that delays the release of the majority of the D-glucose until the dosage form reaches the patient's or subject's ileum and the material is shellac.

101. The method according to claim 53, wherein said oral dosage form further comprises a plant or animal oil, an animal or vegetable fat, caffeine, an herb, tea or a mixture thereof.

* * * * *